US006054637A

United States Patent [19]
Boller et al.

[11] Patent Number: 6,054,637
[45] Date of Patent: Apr. 25, 2000

[54] SIGNAL SEQUENCES FOR VACUOLAR SORTING

[75] Inventors: Thomas Boller, Oberwil; Jean-Marc Neuhaus, Basel, both of Switzerland; John Ryals, Durham, N.C.

[73] Assignee: Novartis Finance Corporation, New York, N.Y.

[21] Appl. No.: 08/329,799

[22] Filed: Oct. 26, 1994

Related U.S. Application Data

[63] Continuation of application No. 07/715,521, Jun. 14, 1991, abandoned.

[30] Foreign Application Priority Data

Jun. 15, 1990 [CH] Switzerland .............................. 2007/90

[51] Int. Cl.[7] .............................. A01H 5/00; A01H 5/10; C12N 1/21; C12N 5/14; C12N 15/29; C12N 15/52; C12N 15/82

[52] U.S. Cl. .................. 800/298; 435/252.2; 435/252.3; 435/252.33; 435/320.1; 435/419; 435/440; 536/23.2; 536/23.6; 800/278

[58] Field of Search .................................. 435/69.1, 69.8, 435/70.1, 252.2, 252.3, 252.33, 320.1, 419, 440; 536/23.6, 23.2; 935/48; 800/278, 298

[56] References Cited

U.S. PATENT DOCUMENTS 5,360,726 11/1994 Raikhel ................................ 435/172.3

FOREIGN PATENT DOCUMENTS

| | | |
|---|---|---|
| 0 351 924 | 1/1990 | European Pat. Off. . |
| 0 353 191 | 1/1990 | European Pat. Off. . |
| 0351924 | 1/1990 | European Pat. Off. . |
| 0353191 | 1/1990 | European Pat. Off. . |
| 0 392 225 | 10/1990 | European Pat. Off. . |
| 0392225 | 10/1990 | European Pat. Off. . |
| 0 418 695 | 3/1991 | European Pat. Off. . |
| 0418695 | 3/1991 | European Pat. Off. . |
| 0 440 304 | 8/1991 | European Pat. Off. . |
| 0 442 592 | 8/1991 | European Pat. Off. . |
| 0442592 | 8/1991 | European Pat. Off. . |
| 0 448 511 | 9/1991 | European Pat. Off. . |
| 0448511 | 9/1991 | European Pat. Off. . |
| 0 460 753 | 12/1991 | European Pat. Off. . |
| 0460753 | 12/1991 | European Pat. Off. . |
| 90/07001 | 6/1990 | WIPO . |
| WO9007001 | 6/1990 | WIPO . |

OTHER PUBLICATIONS

Linthorst et al., "Analysis of Acidic and Basic Chitinases from Tobacco and Petunia and Their Constitutive Expression in Transgenic Tobacco", *Molecular Plant–Microbe Interactions*, 3(4): 252–258 (1990).

Neuhaus et al., "A short C–terminal sequence is necessary and sufficient for the targeting of chitinases to the plant vacuole", *Proc. Natl. Acad. Sci., USA* 88: 10362–10366 (1991).

Shinshi et al., "Structure of a tobacco endochitinase gene: evidence that different chitinase genes can arise by transposition of sequences encoding a cysteine–rich domain", *Plant Molecular Biology*, 14: 357–368 (1990).

Van Den Bulcke et al., "Characterization of vacuolar and extracellular β(1,3)–glucanases of tobacco: Evidence for a strictly compartmentalized plant defense system", *Proc. Natl. Acad. Sci. USA*, 86: 2673–2677 (1989).

Denecke et al., "Protein Secretion in Plant Cell Can Occur via a Default Pathway", *The Palnt Cell*, 2: 51–59 (1990).

Bednarek et al., "Sorting mechanisms of barley lectin to the vacuoles of plant cells", *J. Cell. Biol.*, 111(5, Part 2) Thirtieth Annual Meeting, San Diego, Dec. 9–13, 1990, Abstract 358: 67a (1990).

Bednarket et al., "A Carboxyl–Terminal Propeptide Is Necessary for Proper Sorting of Barley Lectin to Vacuoles of Tobacco", *The Plant Cell*, 2: 1145–1155 (1990).

Farrell et al., "Development of a System for Seed Specific Hyperexpression and Vacuolar Targeting of Foreign Proteins in Plants", *J. Cell Biochem.*, Supplement 14E, 1990, UCLA Symposia on Molecular & Cellular Biology, abstract R412: 333 (1990).

Matsuoka et al., "Propeptide of a precursor to a plant vacuolar protein required for vacuolar targeting", *Proc. Natl. Acad. Sci. USA*, 88:834–838 (1991).

Shinshi et al., "Regulation of a plant pathogenesis–related enzyme: Inhibition of chitinase and chitinase mRNA accumulation in cultured tobacco tissues by auxin and cytokinin", *Proc. Natl. Acad. Sci. USA*, 84: 89–93 (1987).

Shinshi et al., "Evidence of N– and C–terminal processing of a plant defense–related enzyme: Primary structure of tobacco prepro–β–1,3–glucanase", *Proc. Natl. Acad. Sci. USA*, 85: 5541–5545 (1988).

Tague et al., "The Plant Vacuolar Protein, Phytohemagglutinin, Is Transported to the Vacuole of Transgenic Yeast", *J. Cell Biology*, 105: 1971–1979 (1987).

(List continued on next page.)

*Primary Examiner*—Amy J. Nelson
*Attorney, Agent, or Firm*—Bruce Vrana; Gary M. Pace

[57] ABSTRACT

The present invention relates to novel peptide fragments [targeting signal] that are obtainable from the C-terminal region [C-terminal extension] of plant vacuole proteins and that, in operable linkage with any desired protein molecule, ensure that the proteins associated with those peptide fragments are directed specifically into the plant vacuole, and to DNA molecules coding for the said peptide fragments.

The present invention relates also to recombinant DNA molecules that comprise the DNA sequence according to the invention in operable linkage with an expressible DNA, and to the vectors derived therefrom. Also included are host cells and/or host organisms, including transgenic plants, that comprise the said recombinant DNA or the vectors derived therefrom. The present invention also relates to recombinant DNA molecules and vectors derived therefrom that comprise DNA sequences naturally coding for vacuolar proteins, but which are devoid of vacuole signal sequences and targeted for extracellular secretion.

18 Claims, 1 Drawing Sheet

OTHER PUBLICATIONS

Tague et al., "A Short Domain of the Plant Vacuolar Protein Phytohemagglutinin Targets Invertase to the Yeast Vacuole", *The Plant Cell*, 2: 533–546 (1990).

Wilkins et al., "Role of Propeptide Glycan in Post–Translational Processing and Transport of Barley Lectin to Vacuoles in Transgenic Tobacco", *The Plant Cell*, 2: 301–313 (1990).

Wilkins et al., *The Plant Cell*, 2:301–313 (1990).

Linthorst et al., *Molecular Plant–Microbe Interactions*, 3:252–258 (1990).

Shinshi et al., Plant Mol. Biol., 14:357–368 (1990).

Van Den Bulcke et al., *PNAS USA*, 86:2673–2677 (1989).

Bednarek et al., *The Plant Cell*, 2:1145–1155 (1990).

Vitale et al (Mar.) 1992 Biossays 14 (3): 151–160.

Neuhaus et al (Nov.) 1991 Proc Natl Acad Sci USA 88:10362–10366.

Denecke et al (Jan.) 1990 The Plant Cell 2 :51–59.

Dorel et al 1989 The Journal of Cell Biol. 108: 327–337.

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (iii) HYPOTHETICAL: YES (iv) ANTI-SENSE: NO (vi) ORIGINAL SOURCE:
      (A) ORGANISM: DNA sequence encoding a vacuolar signal
          peptide (ix) FEATURE:
      (A) NAME/KEY: CDS
      (B) LOCATION: 1..36

(xi) SEQUENCE DESCRIPTION: SEQ ID NO:1:

CGNTCNTTYG GNAAYGGNCT NTTRGTNGAY ACNATGTAA      39

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: DNA (iii) HYPOTHETICAL: YES (iv) ANTI-SENSE: NO (vi) ORIGINAL SOURCE:
      (A) ORGANISM: DNA sequence encoding a vacuolar signal
          peptide (ix) FEATURE:
      (A) NAME/KEY: CDS
      (B) LOCATION: 1..36

(xi) SEQUENCE DESCRIPTION: SEQ ID NO:2:

CGNTCNTTYG GNAAYGGNCT NCTNGTNGAY ACNATGTAA      39

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide (ix) FEATURE:
        (A) NAME/KEY: CDS
        (B) LOCATION: 1..36

(xi) SEQUENCE DESCRIPTION: SEQ ID NO:3:

CGNAGWTTYG GNAAYGGNCT NTTRGTNGAY ACNATGTAA                        39

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide (ix) FEATURE:
        (A) NAME/KEY: CDS
        (B) LOCATION: 1..36

(xi) SEQUENCE DESCRIPTION: SEQ ID NO:4:

CGNAGWTTYG GNAAYGGNCT NCTNGTNGAY ACNATGTAA                        39

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide (ix) FEATURE:
        (A) NAME/KEY: CDS
        (B) LOCATION: 1..36

(xi) SEQUENCE DESCRIPTION: SEQ ID NO:5:

AGRTCNTTYG GNAAYGGNCT NTTRGTNGAY ACNATGTAA                              39

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide (ix) FEATURE:
        (A) NAME/KEY: CDS
        (B) LOCATION: 1..36

(xi) SEQUENCE DESCRIPTION: SEQ ID NO:6:

AGRTCNTTYG GNAAYGGNCT NCTNGTNGAY ACNATGTAA                              39

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide (ix) FEATURE:
        (A) NAME/KEY: CDS
        (B) LOCATION: 1..36

(xi) SEQUENCE DESCRIPTION: SEQ ID NO:7:

AGRAGWTTYG GNAAYGGNCT NTTRGTNGAY ACNATGTAA                              39

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: YES (iv) ANTI-SENSE: NO (vi) ORIGINAL SOURCE:
        (A) ORGANISM: DNA sequence encoding a vacuolar signal
            peptide

```
    (ix) FEATURE:
         (A) NAME/KEY: CDS
         (B) LOCATION: 1..36

(xi) SEQUENCE DESCRIPTION: SEQ ID NO:8:

AGRAGWTTYG GNAAYGGNCT NCTNGTNGAY ACNATGTAA                              39

(2) INFORMATION FOR SEQ ID NO:9:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (iii) HYPOTHETICAL: YES (iv) ANTI-SENSE: NO (vi) ORIGINAL SOURCE:
         (A) ORGANISM: DNA sequence encoding a vacuolar signal
             peptide (ix) FEATURE:
         (A) NAME/KEY: CDS
         (B) LOCATION: 1..36

(xi) SEQUENCE DESCRIPTION: SEQ ID NO:9:

CGNTCNTTYG GNAAYGGNTT RTTRGTNGAY ACNATGTAA                              39

(2) INFORMATION FOR SEQ ID NO:10:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (iii) HYPOTHETICAL: YES (iv) ANTI-SENSE: NO (vi) ORIGINAL SOURCE:
         (A) ORGANISM: DNA sequence encoding a vacuolar signal
             peptide (ix) FEATURE:
         (A) NAME/KEY: CDS
         (B) LOCATION: 1..36

(xi) SEQUENCE DESCRIPTION: SEQ ID NO:10:

CGNTCNTTYG GNAAYGGNTT RCTNGTNGAY ACNATGTAA                              39

(2) INFORMATION FOR SEQ ID NO:11:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (iii) HYPOTHETICAL: YES (iv) ANTI-SENSE: NO
```

(vi) ORIGINAL SOURCE:
            (A) ORGANISM: DNA sequence encoding a vacuolar signal
                peptide (ix) FEATURE:
            (A) NAME/KEY: CDS
            (B) LOCATION: 1..36

(xi) SEQUENCE DESCRIPTION: SEQ ID NO:11:

CGNAGWTTYG GNAAYGGNTT RTTRGTNGAY ACNATGTAA                                   39

(2) INFORMATION FOR SEQ ID NO:12:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: YES (iv) ANTI-SENSE: NO (vi) ORIGINAL SOURCE:
            (A) ORGANISM: DNA sequence encoding a vacuolar signal
                peptide (ix) FEATURE:
            (A) NAME/KEY: CDS
            (B) LOCATION: 1..36

(xi) SEQUENCE DESCRIPTION: SEQ ID NO:12:

CGNAGWTTYG GNAAYGGNTT RCTNGTNGAY ACNATGTAA                                   39

(2) INFORMATION FOR SEQ ID NO:13:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: YES (iv) ANTI-SENSE: NO (vi) ORIGINAL SOURCE:
            (A) ORGANISM: DNA sequence encoding a vacuolar signal
                peptide (ix) FEATURE:
            (A) NAME/KEY: CDS
            (B) LOCATION: 1..36

(xi) SEQUENCE DESCRIPTION: SEQ ID NO:13:

AGRTCNTTYG GNAAYGGNTT RTTRGTNGAY ACNATGTAA                                   39

(2) INFORMATION FOR SEQ ID NO:14:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: YES

```
        (iv) ANTI-SENSE: NO (vi) ORIGINAL SOURCE:
             (A) ORGANISM: DNA sequence encoding a vacuolar signal
                 peptide (ix) FEATURE:
             (A) NAME/KEY: CDS
             (B) LOCATION: 1..36

(xi) SEQUENCE DESCRIPTION: SEQ ID NO:14:

AGRAGWTTYG GNAAYGGNTT RTTRGTNGAY ACNATGTAA                                39

(2) INFORMATION FOR SEQ ID NO:15:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: YES (iv) ANTI-SENSE: NO (vi) ORIGINAL SOURCE:
             (A) ORGANISM: DNA sequence encoding a vacuolar signal
                 peptide (ix) FEATURE:
             (A) NAME/KEY: CDS
             (B) LOCATION: 1..36

(xi) SEQUENCE DESCRIPTION: SEQ ID NO:15:

AGRTCNTTYG GNAAYGGNTT RCTNGTNGAY ACNATGTAA                                39

(2) INFORMATION FOR SEQ ID NO:16:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: YES (iv) ANTI-SENSE: NO (vi) ORIGINAL SOURCE:
             (A) ORGANISM: DNA sequence encoding a vacuolar signal
                 peptide (ix) FEATURE:
             (A) NAME/KEY: CDS
             (B) LOCATION: 1..36

(xi) SEQUENCE DESCRIPTION: SEQ ID NO:16:

AGRAGWTTYG GNAAYGGNTT RCTNGTNGAY ACNATGTAA                                39

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein
```

```
        (iii) HYPOTHETICAL: YES (iv) ANTI-SENSE: NO (vi) ORIGINAL SOURCE:
             (A) ORGANISM: Vacuolar signal peptide coded for by Seq ID
                 Nos. 1-16

(xi) SEQUENCE DESCRIPTION: SEQ ID NO:17:

Arg Ser Phe Gly Asn Gly Leu Leu Val Asp Thr Met
1               5                   10

(2) INFORMATION FOR SEQ ID NO:18:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM: Nicotiana tabacum
             (B) STRAIN: Havana 425
             (C) INDIVIDUAL ISOLATE: C-terminal extension of basic
                 chitinase gene (vii) IMMEDIATE SOURCE:
             (B) CLONE: pCHN48

(ix) FEATURE:
             (A) NAME/KEY: CDS
             (B) LOCATION: 1..36

(xi) SEQUENCE DESCRIPTION: SEQ ID NO:18:

AGG TCT TTT GGA AAT GGA CTT TTA GTC GAT ACT ATG TAA            39
Arg Ser Phe Gly Asn Gly Leu Leu Val Asp Thr Met
1               5                   10

(2) INFORMATION FOR SEQ ID NO:19:

(i) SEQUENCE CHARACTERISTICS:
             (A) LENGTH: 12 amino acids
             (B) TYPE: amino acid
             (D) TOPOLOGY: linear (ii) MOLECULE TYPE: protein (xi) SEQUENCE DESCRIPTION: SEQ ID NO:19:

Arg Ser Phe Gly Asn Gly Leu Leu Val Asp Thr Met
1               5                   10

(2) INFORMATION FOR SEQ ID NO:20:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO
```

(vi) ORIGINAL SOURCE:
              (A) ORGANISM: Nicotiana tabacum
              (C) INDIVIDUAL ISOLATE: Mutated DNA sequence encoding
                  vacuolar signal peptide (vii) IMMEDIATE SOURCE:
              (B) CLONE: Isolated from mutated pCHN48

(ix) FEATURE:
              (A) NAME/KEY: CDS
              (B) LOCATION: 1..36

(xi) SEQUENCE DESCRIPTION: SEQ ID NO:20:

```
AGG TCT TTT GGA AAA GAT CTT TTA GTC GAT ACT ATG TAA           39
Arg Ser Phe Gly Lys Asp Leu Leu Val Asp Thr Met
 1               5                  10
```

(2) INFORMATION FOR SEQ ID NO:21:

(i) SEQUENCE CHARACTERISTICS:
              (A) LENGTH: 12 amino acids
              (B) TYPE: amino acid
              (D) TOPOLOGY: linear (ii) MOLECULE TYPE: protein (xi) SEQUENCE DESCRIPTION: SEQ ID NO:21:

```
Arg Ser Phe Gly Lys Asp Leu Leu Val Asp Thr Met
 1               5                  10
```

(2) INFORMATION FOR SEQ ID NO:22:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (A) ORGANISM: Nicotiana tabacum
              (C) INDIVIDUAL ISOLATE: Mutated DNA sequence encoding
                  vacuolar signal peptide (vii) IMMEDIATE SOURCE:
              (B) CLONE: Isolated from mutated pCHN48

(ix) FEATURE:
              (A) NAME/KEY: CDS
              (B) LOCATION: 1..36

(xi) SEQUENCE DESCRIPTION: SEQ ID NO:22:

```
AGG TCT TTT GGA AAT GGA CTT TTA GTC AAT ACT ATG TAA           39
Arg Ser Phe Gly Asn Gly Leu Leu Val Asn Thr Met
 1               5                  10
```

(2) INFORMATION FOR SEQ ID NO:23:

(i) SEQUENCE CHARACTERISTICS:
              (A) LENGTH: 12 amino acids
              (B) TYPE: amino acid
              (D) TOPOLOGY: linear (ii) MOLECULE TYPE: protein (xi) SEQUENCE DESCRIPTION: SEQ ID NO:23:

Arg Ser Phe Gly Asn Gly Leu Leu Val Asn Thr Met
 1               5                  10

(2) INFORMATION FOR SEQ ID NO:24:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (A) ORGANISM: Nicotiana tabacum
            (C) INDIVIDUAL ISOLATE: Mutated DNA sequence encoding
                vacuolar signal peptide (vii) IMMEDIATE SOURCE:
            (B) CLONE: Isolated from mutated pCHN48

(ix) FEATURE:
            (A) NAME/KEY: CDS
            (B) LOCATION: 1..36

(xi) SEQUENCE DESCRIPTION: SEQ ID NO:24:

AGG TCT TTT GGA AAT GGA CTT TTA GTC CGT ACT ATG TAA                39
Arg Ser Phe Gly Asn Gly Leu Leu Val Arg Thr Met
 1               5                  10

(2) INFORMATION FOR SEQ ID NO:25:

(i) SEQUENCE CHARACTERISTICS:
            (A) LENGTH: 12 amino acids
            (B) TYPE: amino acid
            (D) TOPOLOGY: linear (ii) MOLECULE TYPE: protein (xi) SEQUENCE DESCRIPTION: SEQ ID NO:25:

Arg Ser Phe Gly Asn Gly Leu Leu Val Arg Thr Met
 1               5                  10

(2) INFORMATION FOR SEQ ID NO:26:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (A) ORGANISM: Nicotiana tabacum
            (C) INDIVIDUAL ISOLATE: Mutated DNA sequence encoding
                vacuolar signal peptide (vii) IMMEDIATE SOURCE:
            (B) CLONE: Isolated from mutated pCHN48

(ix) FEATURE:
              (A) NAME/KEY: CDS
              (B) LOCATION: 2..37

(xi) SEQUENCE DESCRIPTION: SEQ ID NO:26:

WGATCTTTTG GGAAATGGAC TTTTAGTCGA TACTATGTAA                              40

(2) INFORMATION FOR SEQ ID NO:27:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (vi) ORIGINAL SOURCE:
              (A) ORGANISM: Vacuolar signal peptide coded for by Seq. ID.
                  No. 6

(xi) SEQUENCE DESCRIPTION: SEQ ID NO:27:

Asp Leu Leu Gly Asn Gly Leu Leu Val Asp Thr Met
1               5                   10

(2) INFORMATION FOR SEQ ID NO:28:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (A) ORGANISM: Nicotiana tabacum
              (C) INDIVIDUAL ISOLATE: Mutated DNA sequence encoding
                  vacuolar signal peptide (vii) IMMEDIATE SOURCE:
              (B) CLONE: Isolated from mutated pCHN48

(ix) FEATURE:
              (A) NAME/KEY: CDS
              (B) LOCATION: 1..27

(xi) SEQUENCE DESCRIPTION: SEQ ID NO:28:

ATC GGT GAT CTT TTA GTC GAT ACT ATG TAA                                 30
Ile Gly Asp Leu Leu Val Asp Thr Met
  1               5

(2) INFORMATION FOR SEQ ID NO:29:

(i) SEQUENCE CHARACTERISTICS:
              (A) LENGTH: 9 amino acids
              (B) TYPE: amino acid
              (D) TOPOLOGY: linear (ii) MOLECULE TYPE: protein

```
    (xi) SEQUENCE DESCRIPTION: SEQ ID NO:29:

Ile Gly Asp Leu Leu Val Asp Thr Met
 1               5

(2) INFORMATION FOR SEQ ID NO:30:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (A) ORGANISM: Nicotiana tabacum
          (C) INDIVIDUAL ISOLATE: Shorter fragment encoding vacuolar
               signal peptide (vii) IMMEDIATE SOURCE:
          (B) CLONE: Isolated from pCHN48

(ix) FEATURE:
          (A) NAME/KEY: CDS
          (B) LOCATION: 1..18

(xi) SEQUENCE DESCRIPTION: SEQ ID NO:30:

CTT TTA GTC GAT ACT ATG TAA                                              21
Leu Leu Val Asp Thr Met
 1               5

(2) INFORMATION FOR SEQ ID NO:31:

(i) SEQUENCE CHARACTERISTICS:
          (A) LENGTH: 6 amino acids
          (B) TYPE: amino acid
          (D) TOPOLOGY: linear (ii) MOLECULE TYPE: protein (xi) SEQUENCE DESCRIPTION: SEQ ID NO:31:

Leu Leu Val Asp Thr Met
 1               5

(2) INFORMATION FOR SEQ ID NO:32:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: protein (iii) HYPOTHETICAL: NO (iv) ANTI-SENSE: NO (vi) ORIGINAL SOURCE:
          (A) ORGANISM: Nicotiana tabacum
          (C) INDIVIDUAL ISOLATE: Shorter fragment encoding vacuolar
               signal peptide (vii) IMMEDIATE SOURCE:
          (B) CLONE: Isolated from pCHN48
```

```
    (ix) FEATURE:
        (A) NAME/KEY: CDS
        (B) LOCATION: 1..21

(xi) SEQUENCE DESCRIPTION: SEQ ID NO:32:

GGA CTT TTA GTC GAT ACT ATG TAA                                24
Gly Leu Leu Val Asp Thr Met
 1               5

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:33:

Gly Leu Leu Val Asp Thr Met
 1               5

(2) INFORMATION FOR SEQ ID NO:34:

(i) SEQUENCE CHARACTERISTICS:
        (A) LENGTH: 3850 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Nicotiana tabacum L. cv. Havana 425
        (C) INDIVIDUAL ISOLATE: Basic chitinase gene (vii) IMMEDIATE SOURCE:
        (B) CLONE: 1CHN17 (1 phage)

(ix) FEATURE:
        (A) NAME/KEY: CDS
        (B) LOCATION: join(1980..2423, 2698..2849, 3119..3509)

(xi) SEQUENCE DESCRIPTION: SEQ ID NO:34:

GAATTCAATC AAAATGTGTT TTGTATATAG GGTGTCAACT ACTAATATAT TGTTATTTTC     60

TAAAGACATA CATGTATACA TGTAAAATTT ACCGAACTTT ACGGATGTCG ATAACCCCTC    120

TCGATATAGC ATAGGTCCGC CTCTGATTTA CGAAGGGACA CGAGGAAATT CCTCTATGTA    180

ATTAGTTTTA GCAGTTACAC GTTAAAGTAT AAATACATAT TACTTTACCA TAGTTAAGAC    240

CAAACATGTG TATGATTGAC ATACATCTTG CATTCATTAA TTAATTTGAT TTGATGCGAT    300

TAAATTTTTT AAGGATAGAG TTTTTAGTCC AAGTTGAGCT AGTGTAACTC TTATAGTCAA    360

TTGGACTCTC TATTACTAGA TACTATATCA GTTCAAAAGA CACCAATATT GTATTTTAAC    420

AGAAGGAGGC AAATAAGAAA TTGCAAATTC TCAATTCTTT TTAATTATAT CTAATGAACC    480

AAAAGGAGGA AGAGGAGCTA CATATTGGAT TTATAAATAT AAAGCTAGCT GAGGCTCAAA    540

TAATTGTGGA TGCAATACAA GCAATTTACT TAAAACACGA AACAGAAGAG GATTTCGGTC    600

AAATATCGAC ACCTAAGTTT TGAAATACAT TACTGAACAA ATTATGAGAT CATAGACTAG    660

TAATTTAGGA TATTATTCTG TGATTGACTT GATTTTGCAC ATGAAGAAAC GTGAACGGCT    720

TTCTTTTTAG GGCTGCCGTA GAATTGATCA AAACATATCT CAACATATTA AAATAGGGTC    780
```

```
                                           -continued
TCAACTAAAC CGGATTCATG CGGAATGAGA CCCATTTAAA AGGAGCAGTG GTTCCTATTC     840

AAAGAATTAG ATACATTTCT ACATATTTTT AATTATGAAA ATTACTCCTA TACTAATTTG     900

TGTGGTTTTA ATCGAATATG TAAATTTTAT TTGAAAATAA AATAAAAAAT CACAGTCCAA     960

CTTTAATCAT AACACTCAAA TTAAATTCAG CTATCTTTCT AGGACATAGG AAACATTATC    1020

AGTGGAAATA TTATATTATA TCCATAAGAC TTTAGCAAAT CCTATAAGAA GTCTAAACAT    1080

GTAATTGACT ACTTTTAGAA GACGCACTTA TCTAACCCAA GAAACACCTG GCGTAACTCG    1140

AATTTGCTTT TGCCAAAACC AAAAGTCTAG GAATTAAGCT CCAAATTAAA GACATAGATT    1200

TTGGCTTACT TTTTTCAAA AAAAAATAA AATTAAAAAT TAAAATATTT TTTGTTCATG      1260

TAATTTAATC AGTTTTTGGG TGAAATTTTT CTTCCACAC ACAAGATTTT AACTTTTTTC     1320

CAAATAAAAT ACACGTCGAA ACATAAATTC AAATTTCAGA ACTATTTTTC AACGTAATTT    1380

TAAAATTTTT ATTTTCTAGT TTTAACTAAA TCTATGTCCT GATTAAGTCT CCAGTCTTAA    1440

CTCTTAAAGT ATTGAAAATA CATGTTCGAG AATTGTCTGG GATGAAGCTA AGAGCCGCCA    1500

CTAAGAAAAA AAATCTAAAA ATATATAAAA AGGTAAGAGC CGCCACATAA TATATGTAAC    1560

CTGTCGGCGT AATCTACTGA ATTAATTTTC TGGATAAGAA AGATATGACT GAGCTCCGGT    1620

TTGCTCATAG ATTTTGACTT TACTTTTTTA ATTTCTTTTT GAAATATTG TTTGTTTAAT     1680

AAAATATGAT CATGTTTTAG AAAAACAAAT TTCAAAAAAC TTCAAGTTCC CAAAAGTTGT    1740

ATGTCCAAAC ACAACTTTCA AAAATTATTT TTTAAAACAA CTTTAAAAAC TTTTTTTTTA    1800

AATTTTAATT AAATCTATGT CCAAACTAGC CGAAATTCGA GCCTTGGTTA TTCAACCAAT    1860

TGATTTGGTC AGAAAGTCAG TCCTCTCAAC AACTAAAATA GACATTAATT AAGCCATGTC    1920

TCCAGCATCT TCCTTAGCAA TAAATACCTT GCATTTCACC AGTTACTAC TACATTAAA     1979

ATG AGG CTT TGT AAA TTC ACA GCT CTC TCT TCT CTA TTT TCT CTC         2027
Met Arg Leu Cys Lys Phe Thr Ala Leu Ser Ser Leu Phe Ser Leu
  1               5                  10                  15

CTA CTG CTT TCT GCC TCG GCA GAA CAA TGT GGT TCC CAG GCC GGA GGT     2075
Leu Leu Leu Ser Ala Ser Ala Glu Gln Cys Gly Ser Gln Ala Gly Gly
             20                  25                  30

GCG CGT TGT CCC TCG GGT CTC TGC TGC AGC AAA TTT GGT TGG TGT GGT     2123
Ala Arg Cys Pro Ser Gly Leu Cys Cys Ser Lys Phe Gly Trp Cys Gly
         35                  40                  45

AAC ACC AAT GAC TAC TGT GGC CCT GGC AAT TGC CAG AGC CAG TGC CCT     2171
Asn Thr Asn Asp Tyr Cys Gly Pro Gly Asn Cys Gln Ser Gln Cys Pro
 50                  55                  60

GGT GGT CCC ACA CCT ACA CCC CCC ACC CCA CCC GGT GGT GGG GAC CTC     2219
Gly Gly Pro Thr Pro Thr Pro Pro Thr Pro Pro Gly Gly Gly Asp Leu
 65                  70                  75                  80

GGC AGT ATC ATC TCA AGT TCC ATG TTT GAT CAG ATG CTT AAG CAT CGC     2267
Gly Ser Ile Ile Ser Ser Ser Met Phe Asp Gln Met Leu Lys His Arg
             85                  90                  95

AAC GAT AAT GCA TGC CAA GGA AAG GGA TTC TAC AGT TAC AAT GCC TTT     2315
Asn Asp Asn Ala Cys Gln Gly Lys Gly Phe Tyr Ser Tyr Asn Ala Phe
            100                 105                 110

ATC AAT GCT GCT CGG TCT TTT CCT GGC TTT GGT ACC AGT GGC GAT ACC     2363
Ile Asn Ala Ala Arg Ser Phe Pro Gly Phe Gly Thr Ser Gly Asp Thr
        115                 120                 125

ACT GCC CGT AAA AGA GAA ATC GCG GCT TTC TTT GCT CAA ACC TCC CAT     2411
Thr Ala Arg Lys Arg Glu Ile Ala Ala Phe Phe Ala Gln Thr Ser His
            130                 135                 140
```

-continued

```
GAA ACT ACT GGT AAGTCTAGTT ACGTTGAACT ATATGATCGT CTTATTCAAA          2463
Glu Thr Thr Gly
145

AGTTTAATCA ATTAGAGAGA TCATACTTTT ATTTAATCAT ACTGGTCTAT TCTGATTTCA    2523

TGAGACAAAC ACATAGAACT TCCTTTTAAA ATGATTGCGC TGAGACTTGA ATTCAGGACC    2583

TCTATCTGCT CATCACTGGA GTATCCAATT TTGAGATATC ACAATGCTTC TTAAATTTCG    2643

AAGTTTTTTA TAAGCTGACG CGTTCAATAA TTGACCATGT AACCGTTGAC AGGA GGA      2700
                                                              Gly

TGG GCA ACA GCA CCA GAT GGT CCA TAT GCA TGG GGT TAT TGC TGG CTT     2748
Trp Ala Thr Ala Pro Asp Gly Pro Tyr Ala Trp Gly Tyr Cys Trp Leu
150                 155                 160                 165

AGA GAA CAA GGT AGC CCC GGC GAC TAC TGT ACC CCA AGT GGT CAG TGG     2796
Arg Glu Gln Gly Ser Pro Gly Asp Tyr Cys Thr Pro Ser Gly Gln Trp
                170                 175                 180

CCT TGT GCT CCT GGT CGA AAA TAT TTC GGA CGA GGC CCC ATC CAA ATT     2844
Pro Cys Ala Pro Gly Arg Lys Tyr Phe Gly Arg Gly Pro Ile Gln Ile
            185                 190                 195

TCA  CA GTAAGTTCCT TCTTACCCAC ACGGAGTGTT TACACCAAAG TCGTGGGACG       2899
Ser His

GAATGCTTAC TACCTACTAT ATATTTCATT GTGAGAGTAG GTACACAATA TCATGATATT    2959

TCTATGATTA TAAGAGTATG TGATTAATTT CTATGAGAAG TGTAAAGTTA AATAGTTTCC    3019

ACAACACAAA AAAAATGTCA TTTTTTTAAC AGATTAAAAA AGAAAAAGTA TATGATGAAC    3079

TTGTAGGATC TAATTAAGTG TATTTTGACA TAAATACAG C AAC TAT AAC TAC GGG    3134
                                            Asn Tyr Asn Tyr Gly
                                                        200

CCT TGT GGA AGA GCC ATA GGA GTG GAC CTG CTA AAC AAT CCT GAT TTA     3182
Pro Cys Gly Arg Ala Ile Gly Val Asp Leu Leu Asn Asn Pro Asp Leu
205                 210                 215                 220

GTG GCC ACA GAT CCA GTC ATC TCA TTT AAG TCA GCT CTC TGG TTC TGG     3230
Val Ala Thr Asp Pro Val Ile Ser Phe Lys Ser Ala Leu Trp Phe Trp
                225                 230                 235

ATG ACT CCT CAA TCA CCA AAA CCT TCT TGC CAC GAT GTC ATC ATC GGA     3278
Met Thr Pro Gln Ser Pro Lys Pro Ser Cys His Asp Val Ile Ile Gly
            240                 245                 250

AGA TGG CAG CCA TCA GCT GGT GAT CGC GCA GCC AAT CGC CTC CCT GGA     3326
Arg Trp Gln Pro Ser Ala Gly Asp Arg Ala Ala Asn Arg Leu Pro Gly
        255                 260                 265

TTT GGC GTC ATC ACA AAC ATC ATC AAT GGT GGC TTG GAA TGT GGT CGT     3374
Phe Gly Val Ile Thr Asn Ile Ile Asn Gly Gly Leu Glu Cys Gly Arg
    270                 275                 280

GGC ACT GAC TCA AGG GTC CAG GAT CGC ATT GGG TTT TAC AGG AGG TAT     3422
Gly Thr Asp Ser Arg Val Gln Asp Arg Ile Gly Phe Tyr Arg Arg Tyr
285                 290                 295                 300

TGC AGT ATT CTT GGA GTT AGT CCT GGT GAC AAT CTG GAT TGC GGC AAC     3470
Cys Ser Ile Leu Gly Val Ser Pro Gly Asp Asn Leu Asp Cys Gly Asn
                305                 310                 315

CAG AGG TCT TTT GGA AAT GGA CTT TTA GTC GAT ACT ATG TAATTTCATG      3519
Gln Arg Ser Phe Gly Asn Gly Leu Leu Val Asp Thr Met
            320                 325

ATCTGTTTTG TTGTATTCCC TTGCAATGCA GGGCCTAGGG CTATGAATAA AGTTAATGTG    3579

TGAATGTGAA TGTGTGATTG TGACCTGAAG GGATCACGAC TATAATCGTT TATAATAAAC    3639

AAAGACTTTG TCCCAATATA TGTGTTAATG AGCATTACTG TAGTTGGTTT AATTCGGCAC    3699

CAGATAAATA GATAACCACC CGCACTATTA TATTTCATTA TTTAGAAAAC CGAGATCTTT    3759
```

ATTTGAGTGA ATGAAAATCT TCCTAACCAG ATAGTCATAC TAATCAGTCA AAAAAAAATC    3819

TAACCTCAAA ATTTAAGCAT CCGAGCTGCA G                                  3850

(2) INFORMATION FOR SEQ ID NO:35:

(i) SEQUENCE CHARACTERISTICS:
       (A) LENGTH: 148 amino acids
       (B) TYPE: amino acid
       (D) TOPOLOGY: linear (ii) MOLECULE TYPE: protein (xi) SEQUENCE DESCRIPTION: SEQ ID NO:35:

Met Arg Leu Cys Lys Phe Thr Ala Leu Ser Ser Leu Phe Ser Leu
 1               5                  10                  15

Leu Leu Leu Ser Ala Ser Ala Glu Gln Cys Gly Ser Gln Ala Gly Gly
            20                  25                  30

Ala Arg Cys Pro Ser Gly Leu Cys Cys Ser Lys Phe Gly Trp Cys Gly
        35                  40                  45

Asn Thr Asn Asp Tyr Cys Gly Pro Gly Asn Cys Gln Ser Gln Cys Pro
 50                  55                  60

Gly Gly Pro Thr Pro Thr Pro Pro Thr Pro Pro Gly Gly Gly Asp Leu
 65                  70                  75                  80

Gly Ser Ile Ile Ser Ser Ser Met Phe Asp Gln Met Leu Lys His Arg
                85                  90                  95

Asn Asp Asn Ala Cys Gln Gly Lys Gly Phe Tyr Ser Tyr Asn Ala Phe
            100                 105                 110

Ile Asn Ala Ala Arg Ser Phe Pro Gly Phe Gly Thr Ser Gly Asp Thr
        115                 120                 125

Thr Ala Arg Lys Arg Glu Ile Ala Ala Phe Phe Ala Gln Thr Ser His
130                 135                 140

Glu Thr Thr Gly
145

(2) INFORMATION FOR SEQ ID NO:36:

(i) SEQUENCE CHARACTERISTICS:
       (A) LENGTH: 51 amino acids
       (B) TYPE: amino acid
       (D) TOPOLOGY: linear (ii) MOLECULE TYPE: protein (xi) SEQUENCE DESCRIPTION: SEQ ID NO:36:

Gly Trp Ala Thr Ala Pro Asp Gly Pro Tyr Ala Trp Gly Tyr Cys Trp
                 5                  10                  15

Leu Arg Glu Gln Gly Ser Pro Gly Asp Tyr Cys Thr Pro Ser Gly Gln
            20                  25                  30

Trp Pro Cys Ala Pro Gly Arg Lys Tyr Phe Gly Arg Gly Pro Ile Gln
        35                  40                  45

Ile Ser His
 51

(2) INFORMATION FOR SEQ ID NO:37:

(i) SEQUENCE CHARACTERISTICS:
       (A) LENGTH: 130 amino acids
       (B) TYPE: amino acid
       (D) TOPOLOGY: linear -continued (ii) MOLECULE TYPE: protein (xi) SEQUENCE DESCRIPTION: SEQ ID NO:37:

Asn Tyr Asn Tyr Gly Pro Cys Gly Arg Ala Ile Gly Val Asp Leu Leu
            5                  10                 15

Asn Asn Pro Asp Leu Val Ala Thr Asp Pro Val Ile Ser Phe Lys Ser
           20                  25                 30

Ala Leu Trp Phe Trp Met Thr Pro Gln Ser Pro Lys Pro Ser Cys His
        35                  40                 45

Asp Val Ile Ile Gly Arg Trp Gln Pro Ser Ala Gly Asp Arg Ala Ala
    50                  55                 60

Asn Arg Leu Pro Gly Phe Gly Val Ile Thr Asn Ile Ile Asn Gly Gly
65                  70                  75                 80

Leu Glu Cys Gly Arg Gly Thr Asp Ser Arg Val Gln Asp Arg Ile Gly
                85                  90                 95

Phe Tyr Arg Arg Tyr Cys Ser Ile Leu Gly Val Ser Pro Gly Asp Asn
            100                 105                110

Leu Asp Cys Gly Asn Gln Arg Ser Phe Gly Asn Gly Leu Leu Val Asp
        115                 120                125

Thr Met
130

(2) INFORMATION FOR SEQ ID NO:38:

(i) SEQUENCE CHARACTERISTICS:
        (A) LENGTH: 1103 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: TNV-infected cucumber leaves
        (C) INDIVIDUAL ISOLATE: Acidic chitinase gene (vii) IMMEDIATE SOURCE:
        (B) CLONE: pBSCucCht5

(xi) SEQUENCE DESCRIPTION: SEQ ID NO:38:

AAAGAAAGCT CTTTAAGCAA TGGCTGCCCA CAAAATAACT ACAACCCTTT CCATCTTCTT      60

CCTCCTTTCC TCTATTTTCC GCTCTTCCGA CGCGGCTGGA ATCGCCATCT ATTGGGGTCA     120

AAACGGCAAC GAGGGCTCTC TTGCATCCAC CTGCGCAACT GGAAACTACG AGTTCGTCAA     180

CATAGCATTT CTCTCATCCT TTGGCAGCGG TCAAGCTCCA GTTCTCAACC TTGCTGGTCA     240

CTGCAACCCT GACAACAACG GTTGCGCTTT TTTGAGCGAC GAAATAAACT CTTGCAAAAG     300

TCAAAATGTC AAGGTCCTCC TCTCTATCGG TGGTGGCGCG GGGAGTTATT CACTCTCCTC     360

CGCCGACGAT GCGAAACAAG TCGCAAACTT CATTTGGAAC AGCTACCTTG GCGGGCAGTC     420

GGATTCCAGG CCACTTGGCG CTGCGGTTTT GGATGGCGTT GATTTCGATA TCGAGTCTGG     480

CTCGGGCCAG TTCTGGGACG TACTAGCTCA GGAGCTAAAG AATTTTGGAC AAGTCATTTT     540

ATCTGCCGCG CCGCAGTGTC CAATACCAGA CGCTCACCTA GACGCCGCGA TCAAAACTGG     600

ACTGTTCGAT TCCGTTTGGG TTCAATTCTA CAACAACCCG CCATGCATGT TTGCAGATAA     660

CGCGGACAAT CTCCTGAGTT CATGGAATCA GTGGACGGCG TTTCCGACAT CGAAGCTTTA     720

```
CATGGGATTG CCAGCGGCAC GGGAGGCAGC GCCGAGCGGG GGATTTATTC CGGCGGATGT    780

GCTTATTTCT CAAGTTCTTC CAACCATTAA AGCTTCTTCC AACTATGGAG GAGTGATGTT    840

ATGGAGTAAG GCGTTTGACA ATGGCTACAG CGATTCCATT AAAGGCAGCA TCGGCTGAAG    900

GAAGCTCCTA AGTTTAATTT TAATTAAAGC TATGAATAAA CTCCAAAGTA TTATAATAAT    960

TAAAAAGTGA GACTTCATCT TCTCCATTTA GTCTCATATT AAATTAGTGT GATGCAATAA   1020

TTAATATCCT TTTTTTCATT ACTATACTAC CAATGTTTTA GAATTGAAAA GTTGATGTCA   1080

ATAAAAACAT TCCAAGTTTA TTT                                           1103
```

(2) INFORMATION FOR SEQ ID NO:39:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Nicotiana tabacum
        (C) INDIVIDUAL ISOLATE: DNA sequence encoding vacuolar
            signal peptide isolated from (vii) IMMEDIATE SOURCE:
        (B) CLONE: pBS-Gluc39.1

(ix) FEATURE:
        (A) NAME/KEY: CDS
        (B) LOCATION: 1..66

(xi) SEQUENCE DESCRIPTION: SEQ ID NO:39:

```
GTC TCT GGT GGA GTT TGG GAC AGT TCA GTT GAA ACT AAT GCT ACT GCT    48
Val Ser Gly Gly Val Trp Asp Ser Ser Val Glu Thr Asn Ala Thr Ala
 1               5                  10                  15

TCT CTC GTA AGT GAG ATG TGA                                         69
Ser Leu Val Ser Glu Met
            20
```

(2) INFORMATION FOR SEQ ID NO:40:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:40:

```
Val Ser Gly Gly Val Trp Asp Ser Ser Val Glu Thr Asn Ala Thr Ala
 1               5                  10                  15

Ser Leu Val Ser Glu Met
            20
```

(2) INFORMATION FOR SEQ ID NO:41:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:41:

Ala Gly Ile Ala Ile Tyr Trp Gly Gln Asn Gly Asn Glu Gly Ser Leu
 1               5                  10                  15

Ala Ser Thr Cys Ala Thr Gly Asn Tyr Glu Phe Val Asn Ile Ala Phe
                20                  25                  30

Leu
 33

(2) INFORMATION FOR SEQ ID NO:42:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:42:

Lys Asn Phe Gly Gln Val Ile Leu Ser Ala Ala Pro Gln Cys Pro Ile
 1               5                  10                  15

Pro Asp Ala His Leu Asp Ala Ala Ile Lys
                20                  25

(2) INFORMATION FOR SEQ ID NO:43:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:43:

Lys Thr Gly Leu Phe Asp Ser Val Trp Val Gln Phe Tyr Asn Asn Pro
 1               5                  10                  15

Pro Cys Met Phe Ala Asp Asn Ala Asp Asn Leu Leu Ser
                20                  25          29

(2) INFORMATION FOR SEQ ID NO:44:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:44:

Lys Leu Tyr Met Gly Leu Pro Ala Ala Arg Glu Ala Ala Pro Ser Gly
 1               5                  10                  15

Gly Phe Ile Pro Ala Asp
                20

(2) INFORMATION FOR SEQ ID NO:45:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:45:

Lys Ala Ser Ser Asn Tyr Gly Gly Val Met Leu Trp Ser Lys
  1               5                  10

(2) INFORMATION FOR SEQ ID NO:46:

(i) SEQUENCE CHARACTERISTICS:
         (A) LENGTH: 11 amino acids
         (B) TYPE: amino acid
         (D) TOPOLOGY: linear (ii) MOLECULE TYPE: protein (xi) SEQUENCE DESCRIPTION: SEQ ID NO:46:

Met Phe Ala Asp Asn Ala Asp Asn Leu Leu Ser
  1               5                  10

(2) INFORMATION FOR SEQ ID NO:47:

(i) SEQUENCE CHARACTERISTICS:
         (A) LENGTH: 29 amino acids
         (B) TYPE: amino acid
         (D) TOPOLOGY: linear (ii) MOLECULE TYPE: protein (xi) SEQUENCE DESCRIPTION: SEQ ID NO:47:

Met Gly Leu Pro Ala Ala Arg Glu Ala Ala Pro Ser Gly Gly Phe Ile
  1               5                  10                  15

Pro Ala Asp Val Leu Ile Ser Gln Val Leu Pro Thr Ile
                 20                  25

(2) INFORMATION FOR SEQ ID NO:48:

(i) SEQUENCE CHARACTERISTICS:
         (A) LENGTH: 9 amino acids
         (B) TYPE: amino acid
         (D) TOPOLOGY: linear (ii) MOLECULE TYPE: protein (xi) SEQUENCE DESCRIPTION: SEQ ID NO:48:

Val Leu Leu Ser Ile Gly Gly Gly Ala
  1               5

(2) INFORMATION FOR SEQ ID NO:49:

(i) SEQUENCE CHARACTERISTICS:
         (A) LENGTH: 7 amino acids
         (B) TYPE: amino acid
         (D) TOPOLOGY: linear (ii) MOLECULE TYPE: protein (xi) SEQUENCE DESCRIPTION: SEQ ID NO:49:

Thr Gly Leu Phe Asp Xaa Val
  1               5

(2) INFORMATION FOR SEQ ID NO:50:

(i) SEQUENCE CHARACTERISTICS:
         (A) LENGTH: 8 amino acids
         (B) TYPE: amino acid
         (D) TOPOLOGY: linear (ii) MOLECULE TYPE: protein (xi) SEQUENCE DESCRIPTION: SEQ ID NO:50:

Leu Tyr Met Gly Leu Pro Ala Ala
 1               5

(2) INFORMATION FOR SEQ ID NO:51:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:51:

Ala Ser Ser Asn Tyr Gly Gly Val
 1               5

(2) INFORMATION FOR SEQ ID NO:52:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:52:

Ala Phe Asp Asn Gly Tyr
 1               5

(2) INFORMATION FOR SEQ ID NO:53:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:53:

CCRTTYTGNC CCCARTA                                              17

(2) INFORMATION FOR SEQ ID NO:54:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:54:

GGRTTRTTRT ARAAYTGNAC CCA                                       23

(2) INFORMATION FOR SEQ ID NO:55:

(i) SEQUENCE CHARACTERISTICS:
        (A) LENGTH: 22 base pairs
        (B) TYPE: nucleic acid (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:55:

CTGCCTCGGC TGATCAATGT GG                           22

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:56:

TTTGGAAATT GACTCTTAGT CG                           22

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:57:

CCAGAGATCT TTTGGGAAAT GG                           22

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:58:

GACTTTTAGT CAATACTATG TAA                          23

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:59:

GACTTTTAGT CCGTACTATG TAA                23

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:60:

CTTTTGGAAA AGATCTTTTA GTCG               24

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:61:

CCGCTCTTCG GATCCGGCTT G                  21

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:62:

CAGCATCGGT GATCAGGAAG CTC                23

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:63:

CATCTTCTAG ATTTAGTCTC                                                       20

(2) INFORMATION FOR SEQ ID NO:64:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:64:

GGGACACACG TGCACCTT                                                         18

(2) INFORMATION FOR SEQ ID NO:65:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:65:

CTGTCCCAAA CTCCACCAGA TCACCCAAAG TTGATATTAT ATT                             43

(2) INFORMATION FOR SEQ ID NO:66:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:66:

AATATAATAT CAACTTTGGG TGATCTGGTG GAGTTTGGGA CAG                             43

(2) INFORMATION FOR SEQ ID NO:67:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:67:

GCCTCCCCTT CATCGTCC                                                         18

(2) INFORMATION FOR SEQ ID NO:68:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:68:

GGAAATGGAC TTTTAGTCGA TACTAGTTAA                                            30

(2) INFORMATION FOR SEQ ID NO:69:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:69:

GGAAAAGATC TTTTAGTCGA TACTAGTTAA                                            30

(2) INFORMATION FOR SEQ ID NO:70:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:70:

GGAAATGGAC TTTTAGTCAA TACTAGTTAA                                            30

(2) INFORMATION FOR SEQ ID NO:71:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO -continued

```
    (xi) SEQUENCE DESCRIPTION: SEQ ID NO:71:

GGAAATGGAC TTTTAGTCCG TACTAGTTAA                                              30

(2) INFORMATION FOR SEQ ID NO:72:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:72:

ATCGGTGATC TTTTGGGAAA TGGACTTTTA GTCGATACTA TGTAA                             45

(2) INFORMATION FOR SEQ ID NO:73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:73:

ATCGGTGATC TTTTAGTCGA TACTATGTAA                                              30
```

SIGNAL SEQUENCES FOR VACUOLAR SORTING

This application is a continuation, of application Ser. No. 07/715,521, filed Jun. 14, 1991, now abandoned.

BACKGROUND OF THE INVENTION

The present invention relates to novel peptide fragments [targeting signal] that are obtainable from the C-terminal region [C-terminal extension or C-terminal peptide fragment] of plant vacuole proteins and that, in operable linkage with any desired protein molecule, ensure that the proteins associated with those peptide fragments are directed or targeted specifically into the plant vacuole.

The present invention relates also to DNA sequences that code for the peptide fragments characterised in greater detail above and that, in operable linkage with any desired expressible DNA, result in a gene product that is directed specifically into the plant vacuole, and to mutants and variants thereof.

The present invention relates furthermore to recombinant DNA molecules that comprise the DNA sequence according to the invention in operable linkage with an expressible DNA, and to the vectors derived therefrom. Also included are host cells and/or host organisms, including transgenic plants, that comprise the said recombinant DNA or the vectors derived therefrom.

The present invention relates also to processes for the production of the DNA sequences according to the invention and of the recombinant DNA molecules and vectors comprising those DNA sequences, and to the use thereof for the production of transgenic plants.

In genetic engineering, there has recently been an increasing amount of interest in going beyond the pure expression of an inserted foreign gene to identify DNA sequences coding for so-called signal sequences that allow the associated gene product, according to its function, to reach its specific destination, where it can then develop its optimum activity or be stored in suitable manner. With regard to the plant as a whole, this means that attempts are being made, for example, to identify or develop promoters that permit tissue- and/or development-specific expression of an inserted foreign gene.

The target- or destination-oriented placing of inserted foreign genes or their expression products is not only of relevance at the level of the plant, however, but may also be of great importance even at cell level, especially as regards the effectiveness of the transformation.

For example, it is known that, in plant as well as in other eukaryotic cells, although the majority of proteins are synthesised on cytoplasmic ribosomes, a large number of those proteins are required in quite different subcellular compartments. The only exception is formed by some mitochondrial and chloroplast proteins, which are produced at the location in which they are used. The cytoplasmically produced proteins, on the other hand, are either transported along the endomembrane system passing through the cell into the lytic compartment [vacuole, lysosome] of the cell and into the extracellular space, or are taken up directly by their particular compartment [vacuole, chloroplast, peroxisome].

For the maintenance of this compartmentalisation at subcellular level, there must be specific transport and sorting systems inside the cell which ensure that the cytoplasmically produced proteins are distributed according to their function. These proteins must therefore contain one or more additional items of information which enable the said transport and sorting systems of the cell to recognise their own particular substrate and direct it to their specific destination. Thus, for example, in a great many cytoplasmic precursors of mitochondrial and chloroplast proteins it has been possible to detect at the N-terminal end a so-called transit peptide which ensures that the proteins are taken up into their particular compartment. Similarly, the nuclear proteins have a cell-nucleus-specific sequence.

Of particular importance for intracellular protein transport is the cell's endomembrane system. This membrane system, which passes through the cell and is composed of the endoplasmic reticulum and the Golgi apparatus, serves essentially to transport proteins, especially cytoplasmically produced proteins, to the lytic compartment [vacuole, lysosome] and to the extracellular space.

Proteins transported via the endomembrane system first pass into the endoplasmic reticulum. The necessary transport signal for this step is represented by a signal sequence at the N-terminal end of the molecule, the so-called signal peptide. As soon as this signal peptide has fulfilled its function, it is split off proteolytically from the precursor protein. By virtue of its specific function, this type of signal peptide sequence has been conserved to a high degree during evolution in all living cells, irrespective of whether they are bacteria, yeasts, fungi, animals or plants.

A further sorting step then takes place in the Golgi apparatus, where separation of the proteins intended for the lytic compartment [vacuole, lysosome] and of the proteins intended for secretion into the, extracellular space takes place. In experiments on yeasts and animals it has been found that proteins that do not contain an additional signal are apparently secreted automatically into the extraceilular space, while proteins that do contain such an additional sorting signal are discharged into the lytic compartment.

The nature of this sorting signal can vary very widely. In the animals studied hitherto, for example, it is generally a specific modification within the glycan chain of glycoproteins, namely a mannose 6-phosphate group. This group is recognised by a specific mannose 6-phosphate receptor, with the result that the corresponding proteins in specific vesicles are freed from the Golgi apparatus and transported to the lysosomes. However, it has hitherto not been possible to determine which polypeptide sequence gives the impetus for phosphorylation of a mannose group in the glycan side chain.

In yeasts, the corresponding sorting signal for the lytic compartment is not a glycan chain but an amino acid sequence which, after splitting off of the signal peptide, forms the N-terminus of the protein. This N-terminal targeting signal for the vacuole is generally split off in the vacuole itself by means of proteinase A. Often, the protein transported into the vacuole becomes a catalytically active enzyme only as a result of this splitting off of the targeting signal.

In plants, the question of the targeting signal responsible for directing proteins into the vacuole is of particular interest—especially from the point of view of application—because the vacuole not only represents the lytic compartment of the plant cell, but also forms the largest storage compartment for reserve substances, detoxification products and defence substances [Boler and Wiemken (1986)].

It would therefore be very advantageous to be able to direct proteins associated with an improvement in a plant's nutrient content specifically into the vacuole and store them there, since that is by far the largest compartment in the plant cell for dissolved substances. The most important storage proteins of tubers, bulbs, roots and stems, for example, are located in the vacuoles of the cells that compose those organs [Boiler and Wiemke (1986)]. Moreover, the storage proteins of most seeds are located in so-called protein bodies, specialised vacuoles to which the same targeting signals would seem to apply as to the vacuoles of the vegetative organs.

Similar considerations also apply to substances that can be used in the control of pests or diseases, especially when those substances prove to be toxic to the plant itself. It is therefore advantageous to deposit those substances in the plant vacuole too. Finally, in certain cases the vacuole also serves as a detoxification organ by, for example, storing the detoxification products synthesised by the plant [Boller and Wiemke (1986)]. Attempts are therefore being made to direct detoxification enzymes specifically into the vacuole too.

However, precisely the opposite problem arises, for example, in the case of attack of cultivated plants by certain fungal pathogens. These pathogens infect their host plant by spreading their mycelium through the plant's intercellular spaces. Since the chitinases and glucanases that can be used for controlling these pathogens are very often located in the vacuole, their bioavailability in the intercellular space is naturally very limited. In that case, therefore, it would be desirable to be able to discharge those proteins specifically into the extracellular compartment in order to increase the bioavailability of those substances in the intercellular space and thus permit effective control of the fungal pathogen.

Secretion into the extracellular space is also advantageous when specific substances are to be produced using cell cultures. In that case, the directed foreign proteins can very easily be isolated from the surrounding medium since they are secreted into the extracellular space. The breaking up of the cells that is necessary in the case of intracellular production can be omitted.

However, it has hitherto not been possible to identify, let alone isolate such a targeting signal for the plant vacuole.

On the assumption that an N-terminal targeting signal comparable to that in yeasts could be responsible in plants for directing proteins into the vacuole, Tague and Chrispeels (1987) linked various parts of the phytohaemagglutinin molecule from peas with a reporter gene and tested them in yeasts. It was found that in the yeast host, also in the case of phytohaemagglutinin, the N-terminal part of the molecule acts as a targeting signal for the vacuole.

A further vacuole protein, basic β-1,3-glucanase, is synthesised with a C-terminal extension which is lost as the molecule matures. The same also applies to the lectins from rice, barley and wheat (wheatgerm agglutinin). The function of this extension was hitherto unknown.

Since a comparison of the C-termini of various proteins from the vacuole hitherto revealed no apparent homologies in this field, the hypothesis hitherto favoured was that, as with the yeasts, the decisive signal activity in plants originates in the N-terminus of those vacuole proteins.

One of the main problems to be solved within the scope of this invention was, therefore, to identify and isolate a peptide fragment [targeting sequence] responsible for directing an associated protein molecule specifically into the vacuole of the plant cell, and also the DNA sequence coding for the said peptide fragment.

Surprisingly, within the scope of the present invention it has now been possible to solve this problem by the use of procedures of which some are known.

SUMMARY OF THE INVENTION

In detail, the present invention relates to a short peptide fragment that is responsible for directing [targeting] any desired associated protein molecule specifically into the plant vacuole, and to the DNA coding for the said peptide fragment The said associated protein molecule may be a protein of homologous or heterologous origin with respect to the targeting sequence used.

Preference is given to a short peptide fragment that is obtainable from the C-terminal region of a protein molecule present naturally in the vacuole and that, in association with any desired protein molecule, leads to that molecule's being directed in target-oriented manner into the vacuole. Preference is given also to a DNA that codes for the said peptide fragment and is correspondingly obtainable from the 3'-terminal region of the corresponding gene coding for the protein molecule present naturally in the vacuole.

Special preference is given to a short peptide fragment that is obtainable from the C-terminal region of a chitinase molecule present naturally in the vacuole and that, in association with any desired protein molecule, leads to that molecule's being directed in target-oriented manner into the vacuole, and to DNA that codes for the said peptide fragment and is correspondingly obtainable from the 3'-terminal region of a plant chitinase gene.

Very special preference is given to a peptide fragment that acts as the targeting signal for the plant vacuole and that has the following amino acid sequence, which is shown in SEQ ID NOS. 1–17 and 19.

Arg Ser Phe Gly Asn Gly Leu Leu Val Asp Thr Met and to the DNA sequences that code for the said peptide fragment and have the following general formula, which is shown in SEQ ID NOS. 1–16 and 18

```
CGN/AGR TCN/AGW TTY GGN AAY GGN CTN/TTR TTR/CTN GTN GAY
ACN ATG TAA
``` wherein

N is A or G or C or T/U;

R is G or A;

W is A or T/U; and

Y is T/U or C.

Preference is given to those DNA sequences which comprise in the majority the codons preferentially used by the plant.

Special preference is given to a DNA sequence that is in a substantially pure form and that is obtainable, for example, from the 3'-terminal end [C-terminal extension] of a basic chitinase gene of *Nicotiana tabacum* L. c.v. Havana 425 plants and has essentially the following DNA sequence, which is shown in SEQ ID NO: 18:

AGG TCT TTT GGA AAT GGA CTT TTA GTC GAT ACT ATG TAA

Preference is given also to a DNA sequence that is in a substantially pure form and that is obtainable, for example, from the 3'-terminal end [C-terminal extension] of a basic glucanase gene of *Nicotiana tabacun* L. c.v. Havana 425 plants and has essentially the following DNA sequence, which is shown in SEQ ID NO: 39:

```
GTC TCT GGT GGA GTT TGG GAC AGT TCA GTT GAA ACT AAT GCT ACT
GCT TCT CTC GTA AGT GAG ATG TGA
```

The peptide fragment coded for by the said DNA sequence, which peptide fragment acts as the targeting signal for the plant vacuole and has the following amino acid sequence, which is shown in SEQ ID NO: 40, is also included in the present invention:

```
Val Ser Gly Gly Val Trp Asp Ser Ser Val Glu Thr Asn Ala Thr
Ala Ser Leu Val Ser Glu Met
```

Also included are all derivatives of the DNA sequences described in greater detail above that are substantially homologous to those sequences and still have the properties essential to the invention, that is to say that code for a C-terminal peptide that acts as the targeting signal for the plant vacuole.

Within the scope of this invention, a DNA sequence is substantially homologous to a second DNA sequence if at least 60%, preferably at least 80% and very especially preferably at least 90%, of the active sections of the DNA sequences are homologous to one another.

The said derivatives of the DNA sequences according to the invention may be naturally occurring variants or mutants or, especially, they may be variants or mutants that can be produced specifically by means of known mutation methods.

Mutation is to be understood as meaning both the deletion or insertion of one or more bases and the substitution of one or more bases, or a combination of those measures. This is the case especially when the said base substitution is accompanied by a silent mutation which does not result in amino acid substitution.

Examples of such mutants, which are also included in the present invention, are represented by the DNA sequences listed below and shown in SEQ ID NOS. 20–29. These mutants can be produced from the parent sequences shown in SEQ ID NOS. 1–16 and 18 by oligonucleotide-mediated mutagenesis and code for peptide fragments that still have the same targeting properties as the fragments coded for by the said parent sequences:

```
(a)                     GGA AAA GAT CTT TTA GTC GAT ACT ATG TAA
(b)                     GGA AAT GGA CTT TTA GTC AAT ACT ATG TAA
(c)                     GGA AAT GGA CTT TTA GTC CGT ACT ATG TAA
(d) A GAT CTT TTG GGA AAT GGA CTT TTA GTC GAT ACT ATG TAA
(e)                     ATC GGT GAT CTT TTA GTC GAT ACT ATG TAA
```

The empty spaces in sequences (a) to (c) relate to the region of the mutated targeting sequence that has no differences compared with the starting sequence.

Also included in the present invention are peptide fragments that are coded for by the above-mentioned DNA sequences and that still have the same targeting properties as the naturally occurring, unmodified peptide fragments coded for by the said parent sequences according to SEQ ID NOS. 1–16 and 18.

Special preference is given to peptide fragments that act as the targeting signal for the plant vacuole and have the following amino acid sequences, which are shown in SEQ ID NOS. 20–29:

```
(a)                 Gly Lys Asp Leu Leu Val Asp Tht Met End
(b)                 Gly Asn Gly Leu Leu Val Asn Thr Met End
(c)                 Gly Asn Gly Leu Leu Val Arg Thr Met End
(d) Asp Leu Leu Gly Asn Gly Leu Leu Val Asp Thr Met End
(e)                 Ile Gly Asp Leu Leu Val Asp Thr Met End
```

The empty spaces in sequences (a) to (c) relate to the region of the mutated targeting sequence that has no differences compared with the starting sequence.

This list, which is given by way of example, is not intended to be limiting in any way but serves merely to demonstrate that variants of the sequences mentioned above as being preferred can very easily be produced by the person skilled in the art, without the property of those sequences that is essential to the invention being lost.

The present invention also includes fragments or partial sequences that are obtainable from the DNA sequences described in greater detail above or from derivatives of those DNA sequences and that still have the specific properties of the starting sequences.

Special preference is given within the scope of this invention to DNA fragments that are obtainable from the DNA sequence of the invention according to SEQ ID NO: 18 and have essentially the following nucleotide sequences, which are shown in SEQ ID NOS. 30–33:

```
    CTT TTA GTC GAT ACT ATG TAA
GGA CTT TTA GTC GAT ACT ATG TAA
```

The DNA sequences shown above code for peptide fragments that act as the targeting signal for the plant vacuole and have the following amino acid sequence, which is shown in SEQ ID NOS. 30–33:

```
    Leu Leu Val Asp Thr Met End
Gly Leu Leu Val Asp Thr Met End
```

The present invention therefore relates also to the mentioned peptide fragments.

The present invention relates further to recombinant DNA molecules that comprise a chimaeric genetic construction in which any desired expressible DNA is operably linked to one of the DNA sequences according to the invention as well as to expression signals active in plant cells and, optionally, to further coding and/or non-coding sequences of the 3' and/or 5' region, so that, on transformation into a plant host, the expression product is directed specifically into the plant vacuole.

It is advantageous for the expressible DNA in the 5'-terminal region to comprise a sequence that codes for an N-terminal signal peptide capable of functioning in the plant cell, or to be linked to such a sequence. Moreover, the DNA molecule may comprise further sections of sequence that code for peptide fragments which as a whole contribute towards improving the competence for admission into the vacuole, for example the propeptide fragment discovered by Matsuoka K and Nakamura K in the N-terminal extension of sporamine [Matsuoka K and Nakamura K (1991)].

The present invention also includes cloning, transformation and expression vectors that comprise the said recombinant DNA molecule according to the invention, and host organisms transformed with the said vectors.

This invention relates further to so-called shuttle vectors or binary vectors that comprise the said recombinant DNA molecule according to the invention and that are capable of stable replication both in *E. coli* and in *A. tumefaciens*.

Of the host organisms, special preference is given to plant hosts selected from the group consisting of plant protoplasts, cells, calli, tissues, organs, zygotes, embryos, pollen and/or seeds and also, especially, whole, preferably fertile, plants that have been transformed with the said recombinant DNA. Whole plants can either be transformed directly as such with the recombinant DNA molecule according to the invention, or they can be obtained from previously transformed protoplasts, cells and/or tissues by regeneration.

Very especially preferred are transgenic plants, but especially fertile transgenic plants, that comprise one of the constructs according to the invention and in which the expressed gene product, as desired, is located in the vacuole.

The present invention also includes all propagation material of a transgenic plant, the said transgenic plant either having been formed by direct transformation with one of the recombinant DNA molecules according to the invention or being obtained by regeneration from previously transformed protoplasts, cells, calli, tissues, organs, zygotes, embryos, pollen and/or seeds, but without being limited thereto.

Within the scope of this invention, propagation material is to be understood as being any plant material that can be propagated sexually or asexually and in vitro or in vivo, preference being given to protoplasts, cells, calli, tissue, organs, ovules, zygotes, embryos, pollen or seeds that are obtainable from a transgenic plant according to the invention. This invention relates also to the progeny of the said plants and to mutants and variants thereof, including those derived from plants obtained by somatic cell fusion, genetic modification or mutant selection.

The present invention relates furthermore to processes
(a) for the production of one of the DNA sequences according to the invention;
(b) for the production of the recombinant DNA molecules according to the invention that comprise the above DNA sequence according to the invention in operable linkage with any desired expressible DNA sequence, the said DNA sequence preferably being under the regulatory control of plant expression signals;
(c) for the production of cloning, transformation and/or expression vectors that comprise the said recombinant DNA molecule according to the invention;
(d) for the production of transformed host organisms, especially plant hosts selected from the group consisting of plant protoplasts, cells, calli, tissues, organs, zygotes, embryos, pollen and/or seeds and also, especially, whole, preferably fertile, plants;
(e) for the production of propagation material starting from transformed plant material, but especially for the production of sexual and asexual progeny.

Also included in this invention is a process for the target-oriented direction of expression products into the plant vacuole, which process essentially comprises
(a) first of all isolating from a suitable source or synthesising by means of known processes the DNA sequence responsible for specifically directing into the vacuole;
(b) inserting the said DNA sequence in operable manner into the 3'-terminal end of any desired expressible DNA sequence;
(c) cloning the finished construct into a plant expression vector under the control of expression signals active in plants; and
(d) transforming the said expression vector into a plant host and expressing it therein.

It is advantageous for the expressible DNA in the 5'-terminal region to comprise a sequence that codes for an N-terminal signal peptide capable of functioning in the plant cell, or to be linked in operable manner to such a sequence. Moreover, the DNA molecule may comprise further sections of sequence that code for peptide fragments which as a whole contribute towards improving the competence for admission into the vacuole, for example the propeptide fragment discovered by Matsuoka K and Nakamura K in the N-terminal extension of sporamine [Matsuoka K and Nakamura K (1991)].

In the course of the studies carried out within the scope of this invention, it has been found that proteins that naturally comprise one of the targeting sequences according to the invention and that are therefore normally directed into the vacuole are secreted into the extracellular space when they lose the signal sequence according to the invention.

The present invention therefore relates also to a process for discharging into the extracellular space of a plant proteins that naturally comprise a targeting sequence and that are therefore normally directed into one of the cellular compartments, but especially into the vacuole, which process essentially comprises (a) isolating a DNA sequence coding for such a protein, but especially for a vacuole protein;

(b) removing from the open reading frame the targeting sequence at the C-terminal end responsible for directing into the particular cellular compartment, for example by inserting a stop codon directly in front of the C-terminal extension or by removing the C-terminal extension;

(c) splicing the said mutated DNA sequence into a suitable plant expression vector, and (d) transforming the finished construct into a plant host.

DETAILED DESCRIPTION OF THE INVENTION

Definitions

Figure 1:
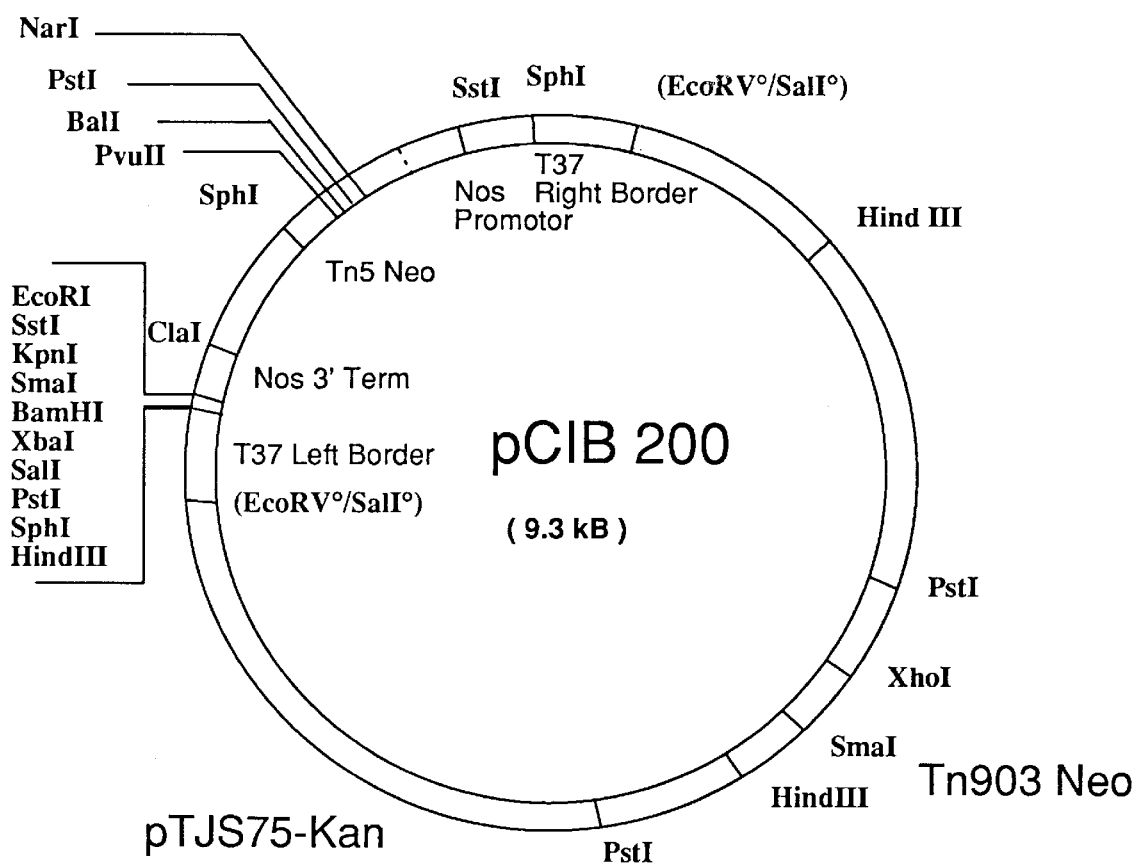
FIG. 1 shows the vector pCIB 200.

In the following description, a number of expressions are used that are customary in recombinant DNA technology and in plant genetics. In order to ensure a clear and uniform understanding of the description and the claims and also of the scope to be accorded to the said expressions, the following definitions are listed.

Plant material: Parts of plants that are viable in culture or that are viable as such, such as protoplasts, cells, callus, tissue, embryos, plant organs, buds, seeds, etc., and also whole plants.

Plant cell: Structural and physiological unit of the plant, comprising a protoplast and a cell wall.

Protoplast: "Naked" plant cell that has no cell wall and has been isolated from plant cells or plant tissues and has the potential to regenerate to a cell clone or a whole plant.

Plant tissue: Group of plant cells organised in the form of a structural and functional unit.

Plant organ: Structural and functional unit comprising several tissues, for example root, stem, leaf or embryo.

Heterologous gene(s) or DNA: A DNA sequence that codes for a specific product or products or fulfills a biological function and that originates from a species other than that into which the said gene is to be inserted; the said DNA sequence is also referred to as a foreign gene or foreign DNA.

Homologous gene(s) or DNA: A DNA sequence that codes for a specific product or products or fulfills a biological function and that originates from the same species as that into which the said gene is to be inserted.

Synthetic gene(s) or DNA: A DNA sequence that codes for a specific product or products or fulfils a biological function and that is produced by synthetic means.

Plant promoter: A control sequence for DNA expression that ensures the transcription of any desired homologous or heterologous DNA gene sequence in a plant, in so far as the said gene sequence is linked in operable manner to such a promoter.

Termination sequence: DNA sequence at the end of a transcription unit that signals the end of the transcription process.

Over-producing plant promoter (OPP): Plant promoter that is capable, in a transgenic plant cell, of bringing about the expression of any operably linked functional gene sequence(s) to a degree (measured in the form of RNA or the amount of polypeptide) that is markedly higher than that observed in the natural state in host cells that have not been transformed with the said OPP.

3'/5' untranslated region: DNA sections located downstream/upstream of the coding region which, although transcribed into mRNA, are not translated into a polypeptide. This region contains regulatory sequences, for example the ribosome binding site (5') or the polyadenylating signal (3').

DNA cloning vector: Cloning vehicle, for example a plasmid or a bacteriophage, containing all the signal sequences necessary for the cloning of an inserted DNA in a suitable host cell.

DNA expression vector: Cloning vehicle, for example a plasmid or a bacteriophage, containing all the signal sequences necessary for the expression of an inserted DNA in a suitable host cell.

DNA transfer vector: Transfer vehicle, for example a Ti-plasmid or a virus, that permits the insertion of genetic material into a suitable host cell.

Mutants, variants of transrenic plants: Derivative of a transgenic plant that has been formed spontaneously or artificially using known procedures, for example UV treatment, treatment with mutagenic agents, etc., and that still has the features and properties of the starting plant that are essential to the invention.

Substantially pure DNA sequence: A DNA sequence isolated in substantially pure form from a natural or non-natural source. Such a sequence may be present in a natural system, for example in bacteria, viruses or in plant or animal cells, or, alternatively, it may be made available in the form of synthetic DNA or of cDNA.

Substantially pure DNA is generally isolated in the form of a vector that comprises the said DNA as an insert. Substantially pure means that other DNA sequences are present in only negligible amounts and make up, for example, less than 5%, preferably less than 1% and very especially preferably less than 0.1%. Such sequences and the vectors comprising those sequences are generally in aqueous solution, namely in a buffer solution or in one of the culture media customarily used.

Within the scope of the present invention it has for the first time been possible to identify and isolate an actual DNA sequence that codes for a short peptide fragment that is responsible for directing any desired associated gene product specifically into the plant vacuole. Especially suitable as the starting material for the isolation of the said DNA sequence according to the invention are cDNA and/or genomic DNA clones of proteins that are present naturally in the vacuole, for example a plant chitinase or glucanase clone.

The present invention therefore relates especially to a novel, substantially pure DNA sequence that is obtainable from the 3'-terminal region of a gene coding for a protein present naturally in the vacuole and that, in operable linkage with any desired expressible DNA, results in a gene product that is directed specifically into the plant vacuole, and to mutants and variants thereof.

Within the scope of this invention, special preference is given to a DNA sequence that is obtainable from the 3'-terminal region of a plant chitinase gene. Preference is likewise given to a DNA sequence that is obtainable from the 3'-terminal region of a plant glucanase gene.

For the isolation of a suitable gene, but especially of a suitable chitinase or glucanase gene, as the source for the DNA sequence according to the invention there are preferably used genomic or cDNA gene libraries that can be produced by customary routine methods very well known to the person skilled in that field. The basic methods of producing genomic or cDNA gene libraries are described in detail, for example, in Maniatis et al (1982), while information relating to the transfer and application of those methods to plant systems will be found, for example, in the Mohnen (1985) reference.

Genomic DNA and cDNA can be obtained in various ways. Genomic DNA, for example, can, using known methods, be extracted from suitable cells and purified.

In a specific embodiment of the present invention, the starting material used for the production of cDNA is generally mRNA, which can be isolated from selected cells or tissues, but especially from cells or tissues that are known to have high concentrations of proteins present naturally in the vacuole, but especially high concentrations of chitinase or glucanase. The isolated mRNA can then be used in a reverse transcription as the matrix for the production of a corresponding cDNA.

Especially preferred according to the invention as starting material for the production of cDNA are plant cells or tissue or other suitable plant material that has previously been stimulated by suitable measures to produce high chitinase or glucanase levels. This can be achieved, for example, by inoculating cultured cells or tissue or other suitable plant material onto a hormone-free medium and culturing it for a period sufficient for the induction of high chitinase or glucanase levels. Within the scope of this invention, special preference is given to a base medium having the salt and thiamine hydrochloride concentration proposed by Linsmaier and Skoog (1965) (LS medium).

The methods of isolating poly ($A^+$) RNA and of producing cDNA are known to the person skilled in the art and are described in detail below in the Examples.

The extracted and purified DNA preparations are then cleaved into fragments for the subsequent cloning. The genomic DNA or cDNA to be cloned may be fragmented to a size suitable for insertion into a cloning vector either by mechanical shearing or, preferably, by cleavage with suitable restriction enzymes. Suitable cloning vectors which are already being used as a matter of routine for the production of genomic and/or cDNA gene libraries include, for example, phage vectors, such as the λ Charon phages, or bacterial vectors, such as the E. coli plasmid pBR322. Further suitable cloning vectors are known to the person skilled in the art.

From the gene libraries produced in that manner, suitable clones comprising the desired gene, for example a chitinase gene or a glucanase gene, or parts thereof can then be identified in a screening programme, for example with the aid of suitable oligonucleotide probes (probe molecule), and then isolated. Various methods are available for identifying suitable clones, for example differential colony hybridisation or plaque hybridisation. Immunological detection methods based on identification of the specific translation products may also be used.

There may be used as probe molecule, for example, a DNA fragment that has already been isolated beforehand from the same gene or from a structurally related gene and that is capable of hybridisation with the corresponding section of sequence within the desired gene that is to be identified.

Provided that the amino acid sequence of the gene to be isolated or at least parts of that sequence are known, a corresponding DNA sequence can be drawn up on the basis of that sequence information. Since the genetic code is known to be degenerate, different codons can in the majority of cases be used for one and the same amino acid. As a result, apart from a few exceptional cases, a particular amino acid sequence can as a rule be coded for by a whole series of oligonucleotides that are similar to one another. However, care must be taken to ensure that only one member of that series of oligonucleotides actually coincides with the corresponding sequence within the gene that is being sought. In order to limit from the outset the number of possible oligonucleotides, the rules on the use of codons laid down by Lathe R et al (1985), which take account of the frequency with which a particular codon is actually used in eukaryotic cells, may, for example, be applied.

On the basis of that information it is thus possible to draw up oligonucleotide molecules that can be used as probe molecules for the identification and isolation of suitable clones by hybridising the said probe molecules with genomic DNA or cDNA in one of the methods described above.

In order to facilitate detection of the desired gene, for example a gene coding for chitinase or glucanase, the above-described DNA probe molecule can be labelled with a suitable readily detectable group. Within the scope of this invention, a detectable group is to be understood as being any material having a particular readily identifiable physical or chemical property.

Such materials are already widely used especially in the field of immunoassays, and the majority of them may also be employed in the present Application. Special mention may be made at this point of enzymatically active groups, for example enzymes, enzyme substrates, coenzymes and enzyme inhibitors, and also of fluorescent and luminescent agents, chromophores and radioisotopes, for example $^3H$, $^{35}S$, $^{32}P$, $^{125}I$ and $^{14}C$. The ready detectability of these labels is based on the one hand on their inherent physical properties (e.g. fluorescent labels, chromophores, radioisotopes) and on the other hand on their reaction and binding properties (e.g. enzymes, substrates, coenzymes, inhibitors).

Also suitable as a probe molecule is a single-stranded cDNA derived from a poly(A)+ RNA, which in turn is isolated from a tissue or a cell induced for the production of high chitinase or glucanase levels.

General methods relating to hybridisation are described, for example, in Maniatis T et al (1982) and in Haymes BT et al (1985).

Those clones within the above-described gene libraries which are capable of hybridisation with a probe molecule and which can be identified by means of one of the above-mentioned detection methods can then be analysed further in order to determine in detail the extent and nature of the coding sequence.

An alternative method of cloning genes, but especially chitinase or glucanase genes, is based on the construction of a gene library composed of expression vectors. In that method, analogously to the methods already described above, genomic DNA, but preferably cDNA, is first isolated from a cell or a tissue capable of expressing a desired gene product—in the present case chitinase or glucanase—and is then spliced into a suitable expression vector. The gene libraries so produced can then be screened using suitable measures, preferably using antibodies, for example anti-chitinase or anti-glucanase antibodies, and those clones selected which comprise the desired gene or at least part of that gene as an insert.

Using the methods described above it is thus possible to isolate a gene that codes for a gene product present naturally in the vacuole, for example a plant chitinase or glucanase gene, but especially a basic chitinase or glucanase gene from tobacco plants, which gene has in its C-terminal extension a DNA sequence that, in operable linkage with any desired structural gene, leads to the gene product's being directed specifically into the vacuole of the transformed plant material.

For further characterisation, the DNA sequences purified and isolated as described above are subjected to sequence analysis. The previously isolated DNA is first cleaved into fragments by means of suitable restriction enzymes and then cloned into suitable cloning vectors, for example the M13 vectors mp18 and mp19. The sequencing is carried out in the 5' H 3' direction, the dideoxynucleotide chain termination method according to Sanger [Sanger et al, 1977] or the method according to Maxam and Gilbert [Maxam and Gilbert, 1980] preferably being used. In order to avoid errors in sequencing, it is advantageous to sequence the two DNA strands in parallel. The analysis of the nucleotide sequence and of the corresponding amino acid sequence is advantageously computer-assisted using suitable commercially available computer software [e.g. GCG software of the University of Wisconsin].

Using generally known procedures, the DNA sequences according to the invention can then be isolated very easily from the DNA clones produced in the above-described manner, but especially from chitinase or glucanase clones.

Within the scope of this invention, special preference is given to a DNA sequence that is in a substantially pure form and that is obtainable, for example, from the 3'-terminal end [C-terminal extension] of a basic chitinase gene of *Nicotiana tabuacum* L. c.v. Havana 425 plants and has essentially the following DNA sequence, which is shown in SEQ ID NO: 18:

AGG TCT TTT GGA AAT GGA CIT TTA GTC GAT ACT ATG TAA

The DNA sequence shown above codes for a peptide fragment that, in operable linkage with a protein molecule, acts as the targeting signal for the plant vacuole and that has the following amino acid sequence, which is shown in SEQ ID NO: 17:

Arg Ser Phe Gly Asn Gly Leu Leu Val Asp Thr Met

The present invention relates also to the mentioned peptide fragment.

Preference is given also to a DNA sequence that is in a substantially pure form and that is obtainable, for example, from the 3'-terminal end [C-terminal extension] of a basic glucanase gene of *Nicotiana tabuacum* L. c.v. Havana 425 plants and has essentially the following DNA sequence, which is shown in SEQ ID NOS. 39–40:

The peptide fragment coded for by the said DNA sequence, which peptide fragment, in operable linkage with an expressible DNA, acts as the targeting signal for the plant vacuole, has the following amino acid sequence, which is shown in SEQ ID NOS. 39 and 40, and is also included in the present invention:

Val Ser Gly Gly Val Trp Asp Ser Ser Val Glu Thr Asn Ala Thr
Ala Ser Leu Val Ser Glu Met

It goes without saying that the DNA sequences according to the invention, the base sequence of which is known, do not have to be newly isolated each time from a suitable chitinase or glucanase gene but can of course be synthesised very easily at any time by means of known chemical processes. Suitable processes for the synthesis of short DNA oligonucleotides, for example the phosphotriester or phosphite method, are known to the person skilled in the art. Today, the majority of oligonucleotide syntheses are mechanised and automated, so that short DNA fragments can be produced in a short period of time.

The same applies also to the amino acid sequences of the corresponding targeting peptides, which sequences can be derived directly from the base sequence.

By deletion, insertion or substitution of one or more base pairs in the above-mentioned DNA sequence according to the invention, therefore, variants or mutants of those sequences can very easily be produced and checked for their suitability as a targeting sequence.

Within the scope of the present invention there are disclosed a large number of sequences which can be produced very easily from a naturally occurring starting sequence by means of mutagenesis.

In detail, the procedure may be that a gene comprising one of the DNA sequences according to the invention is first identified and isolated. After splicing into a suitable cloning vector, that gene, but especially the 3'-terminal targeting sequence, can then be modified by means of known procedures. An especially suitable method of producing specific mutants is so-called oligonucleotide-mediated mutagenesis. In that method, short oligonucleotide fragments are synthesised which, although substantially homologous to the wild-type sequence, differ therefrom in individual nucleotides. The said differences may be insertions, deletions, inversions or a substitution of one or more nucleotides, or they may be a combination of the above-mentioned procedures. These mutated fragments are then substituted for the homologous counterparts on the wild-type gene by generally known methods. The finished construct can then, as described above, be cloned into a suitable plant expression vector and transformed into a plant.

However, the mutation of certain DNA fragments can also preferably be carried out using the polymerase chain reaction [PCR]. In this in vitro process there are used chemically synthesised oligonucleotides which generally originate from the peripheral regions of the DNA fragment to be mutated and are strand-specific. Under suitable conditions, hybridisation of the oligonucleotides with the complementary regions on the DNA single strands produced by denaturing occurs. The double-stranded regions produced in this manner are used as primers for the subsequent polymerase reaction.

GTC TCT GGT GGA GTT TGG GAC AGT TCA GTT GAA ACT AAT GCT ACT
GCT TCT CTC GTA AGT GAG ATG TGA

In this process there may be used in addition to DNA polymerases from *E. coli* especially heat-stable polymerases from thermophilic bacteria, for example *Thermus aquaticus*.

The present invention is therefore not limited to the base sequence described in greater detail above but also includes all mutants and/or variants of those DNA sequences that can be produced by deletion or insertion of one or more bases or, especially, by the substitution of one or more bases, and that still have the specific properties, according to the invention, of the starting sequences.

Within the scope of this invention, special preference is given to the following variants, which can be produced by oligonucleotide-mediated mutagenesis from the starting sequences shown in SEQ ID NOS. 1–16 and 18 and code for peptides that still have the same targeting properties as the peptides coded for by the said starting sequences [SEQ ID NOS. 20–29]:

```
(a)                  GGA AAA GAT CTT TTA GTC GAT ACT ATG TAA
(b)                  GGA AAT GGA CTT TTA GTC AAT ACT ATG TAA
(c)                  GGA AAT GGA CTT TTA GTC CGT ACT ATG TAA
(d) A GAT CTT TTG GGA AAT GGA CTT TTA GTC GAT ACT ATG TAA
(e)                  ATC GGT GAT CTT TTA GTC GAT ACT ATG TAA
```

The empty spaces in sequences (a) to (c) relate to the region of the mutated targeting sequence that has no differences compared with the starting sequence.

The DNA sequences according to the invention that can be isolated or produced in the manner described above can now be used to identify homologous DNA sequences having the same function by, for example, first producing genomic or cDNA gene libraries and investigating them in the manner described above, using the DNA sequences according to the invention as probe molecules, for the presence of homologous DNA sequences that are capable of hybridisation with those probe molecules.

The present invention relates also to those processes for locating homologous DNA sequences having the same function.

The present invention also includes peptide fragments that are coded for by the above-mentioned DNA sequences and that still have the same targeting properties as the naturally occurring, unmodified peptide fragments coded for by the said parent sequences shown in SEQ ID NOS. 1–16 and 18.

Special preference is given to peptide fragments that act as the targeting signal for the plant vacuole and have the following amino acid sequences [SEQ ID NOS. 20–29]:

```
(a)              Gly Lys Asp Leu Leu Val Asp Thr Met End
(b)              Gly Asn Gly Leu Leu Val Asn Thr Met End
(c)              Gly Asn Gly Leu Leu Val Arg Thr Met End
(d) Asp Leu Leu Gly Asn Gly Leu Leu Val Asp Thr Met End
(e)              Ile Gly Asp Leu Leu Val Asp Thr Met End
```

The empty spaces in sequences (a) to (c) relate to the region of the mutated targeting sequence that has no differences compared with the starting sequence.

The present invention also includes fragments or partial sequences that are obtainable from the DNA sequences described in greater detail above or from derivatives of those DNA sequences, and that still have the specific properties of the starting sequences.

Within the scope of this invention, special preference is given to DNA fragments that are obtainable from the DNA sequence according to the invention and have essentially the following nucleotide sequences, which are shown in SEQ ID NOS. 30–33:

```
        CTT TTA GTC GAT ACT ATG TAA
    GGA CTF TFA GTC GAT ACT ATG TAA
```

The DNA sequences shown above code for peptide fragments that act as the targeting signal for the plant vacuole and have the following amino acid sequence, which is shown in SEQ ID NOS. 30–33:

```
        Leu Leu Val Asp Thr Met
    Gly Leu Leu Val Asp Thr Met
```

The present invention therefore relates also to the mentioned peptide fragments.

Within the scope of the present invention, it has now for the first time been possible to show that the DNA sequences according to the invention and characterised in greater detail above, which code for a short, C-terminal peptide fragment that is responsible for specifically directing the structural gene naturally associated therewith, can continue to fulfill their targeting function even when linked to heterologous genes.

In a specific embodiment of the present invention, the DNA sequence according to the invention is, by means of the methods described above, linked in operable manner to a heterologous gene, preferably a heterologous chitinase gene, that does not have a corresponding 3'-terminal sequence, and transformed into a plant host. A gene product that is directed specifically into the plant vacuole is then expressed in that transformed host plant.

In detail, the procedure may be that a cDNA gene library is first produced from suitable plant material and a suitable chitinase cDNA clone that does not have a 3'-terminal extension is isolated from the said gene library with the aid of suitable probe molecules. After that cDNA clone has been spliced into a suitable cloning vector, the said clone can be modified by insertion or deletion of restriction cleavage sites in such a manner that the DNA targeting sequence according to the invention can be linked in operable manner to the heterologous chitinase gene. The finished construct can then be cloned into a suitable plant expression vector, whereby it comes under the regulatory control of expression signals active in plants. There may be mentioned as an example at this point the plant expression vector pGY1, which comprises the 35S promoter of the CaMV virus and also its termination sequences; however, this does not limit the subject of the present invention in any way. Of course, any other suitable vector may also be used at this point.

For example, by linkage with the targeting sequence according to the invention it is possible to direct specifically into the plant vacuole an acidic chitinase from cucumbers that does not have a C-terminal signal peptide and therefore is normally secreted into the extracellular space.

The present invention therefore relates also to the construction of chimaeric recombinant DNA molecules that comprise an expressible DNA, but especially a structural gene, preferably a heterologous structural gene, in operable linkage with the DNA sequence according to the invention and with expression signals active in plant cells, such as promoter and termination sequences, as well as, optionally, with further coding and/or non-coding sequences of the 5' and/or 3' region.

It is often advantageous to incorporate a leader sequence between the promoter sequence and the adjacent coding DNA sequence, the length of the leader sequence being so selected that the distance between the promoter and the DNA sequence according to the invention is the optimum distance for expression of the associated structural gene.

It is also advantageous for the DNA molecule that is to be inserted to comprise a sequence that codes for an N-terminal signal peptide capable of functioning in the plant cell, or to be linked in the 5'-terminal region to such a sequence. Moreover, the DNA molecule may comprise further sections of sequence that code for peptide fragments which as a whole contribute towards improving the competence for admission into the vacuole, for example the propeptide fragment discovered by Matsuoka K and Nakamura K in the N-terminal extension of sporamine [Matsuoka K and Nakamura K (1991)].

There are suitable for use in the process according to the invention especially all those structural genes which lead to a protective effect in the transformed plant cells and also in the tissues developing therefrom and especially in the plants, for example increased resistance to pathogens (for example to phytopathogenic fungi, bacteria, viruses, etc.); resistance to chemicals [for example to herbicides (e.g. triazines, sulfonylureas, imidazolinones, triazole pyrimidines, bialaphos, glyphosate, etc.), insecticides or other biocides]; resistance to adverse environmental factors (for example to heat, cold, wind, adverse soil conditions, moisture, dryness, etc.).

Within the scope of this invention, special mention is to be made of structural genes that are associated with the control of plant pathogens and parasites.

Resistance to insects can be conferred, for example, by a gene coding for a polypeptide that is toxic to insects and/or their larvae, for example the crystalline protein of *Bacillus thuringiensis*.

A second class of proteins mediating resistance to insects comprises the protease inhibitors. Protease inhibitors are a normal constituent of plant storage structures and are therefore normally located in vacuoles or protein bodies. It has been demonstrated that a Bowman-Birk protease inhibitor isolated from soybeans and purified inhibits the intestinal protease of Tenebrio larvae [Birk et al (1963)]. The gene that codes for the trypsin inhibitor from the cowpea is described in Hilder et al (1987).

Within the scope of the present invention, it is now possible to use any desired protease inhibitors irrespective of their origin [for example protease inhibitors from non-plant or purely synthetic sources] by linking them in operable manner to an N-terminal signal peptide capable of functioning in the plant cell and to the C-terminal targeting sequence according to the invention. As a result, the protease inhibitors so modified are directed specifically into the vacuole, where they can be stored in optimum manner.

A gene that codes for a protease inhibitor can, in a suitable vector, be brought under the control of a plant promoter, especially of a constitutive promoter, for example the CaMV 35S promoter. The gene, for example the coding sequence of the Bowman-Birk protease inhibitor from the soybean, can be obtained by the cDNA cloning method. A further possible method of producing a protease inhibitor is synthetic manufacture, provided that the protease inhibitor comprises fewer than 100 amino acids, for example the trypsin inhibitor of the lima bean. The coding sequence can be predicted by reverse translation of the amino acid sequence. In addition, there are incorporated at both ends restriction cleavage sites suitable for the vector desired in each particular case. The synthetic gene is produced by synthesis of overlapping oligonucleotide fragments of from 30 to 60 base pairs, by first subjecting those fragments to a kinase reaction, then linking them to one another [Maniatis et al (1982)] and finally cloning them in a suitable vector. By means of DNA sequencing it is then possible to identify a clone that has the insert in a correct orientation. For insertion into the protoplasts, isolated plasmid DNA can be used.

In this connection, mention should also be made of hydrolytic enzymes, which are capable of bringing about the breakdown of the cell walls of plant pathogens themselves, or at least assist that breakdown in conjunction with other substances in the sense of synergy.

The majority of insects, for example, have a cuticular skeleton in which chitin micelles in lamellar layers are embedded in a base substance. A great many phytopathogenic fungi also contain chitin as an integral part of their hypha and spore structures, for example *Basidiomycetes* (smut and rust fungi), *Ascomycetes* and *Fungi imperfecti* (including Alternaria and Bipolaris, *Exerophilum turcicum*, Colletotricum, Gleocercospora and Cercospora). Chitinase is capable of inhibiting the mycelial growth of certain pathogens in vitro. A plant organ or tissue that is capable of expressing chitinase constitutively or in response to the penetration of a pathogen could therefore protect itself from attack by a large number of different fungi.

The endogenous chitinases that are present naturally in the plant are either extracellular (acidic chitinases) or located inside the vacuole (basic chitinases), so that two alternative procedures may be envisaged within the scope of the present invention.

On the one hand, the acidic chitinase genes, which lack the sequence at the C-terminal end that is responsible for directing into the vacuole, can be modified using the DNA sequence according to the invention in such a manner that the gene products pass specifically into the vacuole, where they are able to assist the endogenous basic chitinases that occur naturally there in their activity against penetrating pathogens.

In the second variant, the C-terminal extension of a basic chitinase gene present naturally in the vacuole is removed from the open reading frame by means of genetic engineering methods or is at least inactivated, for example by inserting a stop codon directly in front of the C-terminal extension. As a result, the gene product is secreted into the intercellular space, where it can come into direct contact with the penetrating pathogen.

A further aspect of the present invention therefore relates to recombinant DNA molecules that comprise a structural gene that is present naturally in the vacuole and is in operable linkage with expression signals active in plant cells, in which structural gene the 3'-terminal targeting sequence, which is naturally present in the gene, has been deleted or otherwise inactivated. On transformation into a plant host, these constructs produce an expression product that does not contain a functional C-terminal signal sequence and is therefore secreted into the extracellular space of the plant.

Special preference is given to a recombinant DNA molecule that comprises a basic chitinase gene that is in operable linkage with expression signals active in plant cells and in which the 3'-terminal targeting sequence, which is naturally present in the gene, has been deleted or otherwise inactivated and that therefore, on transformation into a plant host, produces an expression product that does not contain a functional C-terminal signal sequence and is therefore secreted into the extracellular space of the plant.

A further enzyme which presumably plays a central role in the plant's defence mechanism against pathogens is β-1,3-glucanase, the use of which in combination with the DNA sequence according to the invention is therefore also preferred within the scope of this invention.

Preference is therefore given also to a recombinant DNA molecule that comprises a basic glucanase gene that is in operable linkage with expression signals active in plant cells and in which the 3'-terminal targeting sequence, which is naturally present in the gene, has been deleted or otherwise inactivated and that therefore, on transformation into a plant host, produces an expression product that does not contain a functional C-terminal signal sequence and is therefore secreted into the extracellular space of the plant.

This invention relates further to the linking of the targeting sequence according to the invention to so-called lytic peptides. These are natural or synthetic peptides having anti-pathogenic activity which are capable of penetrating, lysing or otherwise damaging the cell membrane of pathogens. Representatives of such lytic peptides that may be used within the scope of the present invention are known both from animal sources [including insects] and from plant and microbial sources and include, for example, the defensines, cercopines, thionines and mellitines of mammals, and the defensines, magainines, attacines, dipterines, sapecines, caerulines and xenopsines of insects, and hybrids thereof. The amino acid sequences of various lytic peptides are shown in the following publications: WO 89/11291; WO 86/04356; WO 88/05826; U.S. Pat. No. 4,810,777; WO 89/04371, and in Bohlmann et al (1988), Selsted and Hartwig (1987) and Terry et al (1988).

Lytic peptides in the broadest sense of the term are also to be understood as being compounds whose ability to penetrate, lyse or damage cell membranes is based on enzymatic activity, for example lysozymes and phospholipases.

Special preference is given within the scope of this invention to the combined expression of hydrolytic and lytic peptides with subsequent target-oriented direction into the vacuole or, where appropriate, into the extracellular space. Moreover, reciprocal use of expression and exogenous application may also be envisaged, the lytic peptides especially being suitable for the latter purpose, in conjunction with the auxiliaries and/or additives customarily used for this purpose.

The DNA sequence according to the invention can also be used in ideal manner for the production of desirable and useful compounds in the plant cell as such or as part of a unit of higher organisation, for example a tissue, callus, organ, embryo or a whole plant.

Genes that may also be used within the scope of the present invention include, for example, those which lead to increased formation of reserve or stored substances in leaves, seeds, tubers, roots, stems, etc. or in the protein bodies of seeds. The desirable substances that can be produced by transgenic plants include, for example, proteins, carbohydrates, amino acids, vitamins, alkaloids, flavins, perfumes, colourings, fats, etc.

There may also be associated with the DNA sequence according to the invention structural genes that code for pharmaceutically acceptable active substances, for example hormones, immunomodulators and other physiologically active substances.

The genes that can come into consideration within the scope of this invention therefore include, but are not limited to, for example, plant-specific genes, such as the zein gene from maize, the avenin gene from oats, the glutelin gene from rice, etc., mammal-specific genes, such as the insulin gene, the somatostatin gene, the interleulin genes, the t-PA gene, etc., or genes of microbial origin, such as the NPT II gene, etc. and synthetic genes, such as the insulin gene, etc.

Apart from naturally occurring structural genes that code for a useful and desirable property, within the scope of this invention it is also possible to use genes that have been modified previously in a specific manner using chemical or genetic engineering methods.

Furthermore, the broad concept of the present invention also includes genes that are produced entirely by chemical synthesis. Genes or DNA sequences that may be used within the scope of the present invention are therefore both homologous and heterologous gene(s) or DNA and also synthetic gene(s) or DNA according to the definition given within the scope of the present invention. The insulin gene may be mentioned at this point as an example of a synthetic gene.

The DNA sequences that may be used within the scope of the present invention may be constructed exclusively from genomic DNA, from cDNA or from synthetic DNA. Another possibility is the construction of a hybrid DNA sequence comprising cDNA and also genomic DNA and/or synthetic DNA.

In that case, the cDNA may originate from the same gene as the genomic DNA, or both the cDNA and the genomic DNA may originate from different genes. In any case, however, both the genomic DNA and/or the cDNA may each be produced individually from the same gene or from different genes.

If the DNA sequence contains portions of more than one gene, these genes may originate from one and the same organism, from several organisms belonging to different strains or varieties of the same species or different species of the same genus, or from organisms belonging to more than one genus of the same or of a different taxonomic unit (kingdom).

In order to ensure the expression of the said structural genes in the plant cell, it is advantageous for the coding gene sequences first to be linked in operable manner to expression sequences capable of functioning in plant cells.

The hybrid gene constructions within the scope of the present invention therefore comprise, in addition to the DNA sequence according to the invention, one or more structural gene(s) and, in operable linkage therewith, expression signals which include both promoter and terminator sequences and other regulatory sequences of the 3' and 5' untranslated regions.

Any promoter and any terminator capable of bringing about an induction of the expression of a coding DNA sequence (structural gene) may be used as a constituent of the hybrid gene sequence. Especially suitable are expression signals originating from genes of plants or plant viruses. Examples of suitable promoters and terminators are those of the Cauliflower Mosaic Virus genes (CaMV) or homologous DNA sequences that still have the characteristic properties of the mentioned expression signals. Also suitable are bacterial expression signals, especially the expression signals of the nopaline synthase genes (nos) or the octopine synthase genes (ocs) from the Ti-plasmids of *Agrobacterium tumeaciens*.

Within the scope of this invention, preference is given to the 35S and 19S expression signals of the CaMV genome or their homologues which can be isolated from the said genome using molecular biological methods, as described, for example, in Maniatis et al (1982), and linked to the coding DNA sequence.

Within the scope of this invention, homologues of the 35S and 19S expression signals are to be understood as being sequences that, despite slight sequence differences, are substantially homologous to the starting sequences and still fulfil the same function as those starting sequences.

In accordance with the invention there may be used as starting material for the 35S transcription control sequences, for example, the ScaI fragment of the CaMV strain "S", which includes the nucleotides 6808–7632 of the gene map [Frank G et al (1980)].

The 19S promoter and 5' untranslated region is located on a genome fragment between the PstI site (position 5386) and the HindIII site (position 5850) of the CaMV gene map [Hohn et al (1982)]. The corresponding terminator and 3' untranslated region is located on an EcoRV/BglII fragment between positions 7342 and 7643 of the CaMV genome.

Also preferred within the scope of this invention are the expression signals of the CaMV strain CM 1841, the complete nucleotide sequence of which is described in Gardner RC et al (1981).

A further effective representative of a plant promoter that may be used is an over-producing plant promoter. Provided that this type of promoter is operably linked to the gene sequence that codes for a desired gene product, it should be capable of mediating the expression of the said gene sequence.

Over-producing plant promoters that may be used within the scope of the present invention include the promoter of the small subunit (ss) of ribulose-1,5-biphosphate carboxylase from soybeans and also the promoter of the chlorophyll-a/b-binding protein.

These two promoters are known for the fact that they are induced by light in eukaryotic plant cells [see, for example, Genetic Engineering of Plants, An Agricultural Perspective, Cashmore A (1983)].

The present invention therefore relates also to recombinant DNA molecules that comprise a chimaeric genetic construction in which the DNA sequence according to the invention is operably linked to an expressible DNA and to expression signals active in plant cells as well as, optionally, to further transcribed and/or untranscribed sequences of the 5' and/or 3' region, so that, on transformation into a plant host, the expression products are directed specifically into the plant vacuole.

Special preference is given to recombinant DNA molecules that comprise a chimaeric genetic construction in which the DNA sequence according to the invention is operably associated with a structural gene that confers on the transformed plant cells and also on the tissues developing therefrom, and especially on the plants, a protective effect against pathogens, chemicals and also adverse environmental factors.

Very special preference is given within the scope of this invention to recombinant DNA molecules that comprise a chimaeric genetic construction in which the DNA sequence according to the invention is operably associated with a structural gene that expresses chitinase, but especially acidic chitinase, or glucanase, but especially acidic glucanase, in plant cells.

The present invention also includes recombinant DNA molecules that comprise a chimaeric genetic construction in which the DNA sequence according to the invention is operably associated with a structural gene that, on expression in the transformed plant cell as such or as part of a unit of higher organisation selected from the group consisting of a tissue, organ, callus, embryo and a whole plant, leads to the direction of desired and useful compounds into the plant vacuole.

Preference is given furthermore to recombinant DNA molecules that comprise a chimaeric genetic construction in which a gene that codes for a protein molecule present naturally in the vacuole, but preferably a basic chitinase gene, and very especially preferably a basic chitinase gene from tobacco or cucumber plants, has been so modified that it is secreted into the extracellular space. In detail, this may be achieved by removing or inactivating the C-terminal extension that is present naturally in the said genes, but especially in chitinase genes, and comprises the DNA sequences responsible for directing into the vacuole, with the aid of genetic engineering methods, for example by inserting a stop codon directly in front of the C-terminal extension.

Further regulatory DNA sequences that may be used for the construction of chimaeric genes include, for example, sequences that are capable of regulating the transcription of an associated DNA sequence in plant tissues in the sense of induction or repression.

There are, for example, certain plant genes that are known to be induced by various internal and external factors, such as plant hormones, heat shock, chemicals, pathogens, oxygen deficiency, light, stress, etc.

As an example of gene regulation by a plant hormone, mention should here be made of abscisic acid (ABS), which is known to induce the excess of mRNAs which occurs during the late embryonal phase in cotton. A further example is gibberellic acid (GA3) which induces malate synthase transcripts in castor beans and isoenzymes of α-amylase in the aleurone layers of barley.

The activity of glucanase and chitinase in bean leaves can be markedly increased by treatment with the stress hormone ethylene. In the case of chitinase, this induction effect is controlled via the promoter of the chitinase gene, and it was possible to demonstrate this by reporter gene tests using a promoter from the chitinase gene of beans (*Phaseolus vulgaris*).

The regulation of heat-shock-sensitive protein genes of soybeans has been studied in detail. Treating the plants for several hours at a temperature of 40° C. results in the de novo synthesis of so-called heat-shock proteins. A large number of those genes have since been isolated, and their regulation has been analysed in detail. The expression of those genes is controlled primarily at the transcription level. For example, if the promoter of the hps70 gene is fused with the neomycin phosphotransferase II (NPT II) gene, the chimaeric gene so formed can be induced by a heat shock [Spena et al, 1985].

Another class of genes that are inducible in plants comprises the light-regulated genes, especially the nuclear-coded gene of the small subunit of ribulose-1,5-biphosphate carboxylase (RUBISCO). Morelli et al (1985) have shown that the 5'-flanking sequence of a RUBISCO gene from the pea is capable of transferring light-inducibility to a reporter gene, provided the latter is linked in chimaeric form to that sequence. It has also been possible to extend this observation to other light-induced genes, for example the chlorophyll-a/b-binding protein.

The alcohol dehydrogenase genes (adh genes) of maize have been the subject of intensive research. The adh1-s gene from maize was isolated, and it was shown that a part of the 5'-flanking DNA is capable of inducing the expression of a chimaeric reporter gene (e.g. chloramphenicol acetyl transferase; CAT) when the temporarily transformed tissue was subjected to anaerobic conditions [Howard et al (1987)].

A further group of regulatable DNA sequences comprises chemically regulatable sequences that are present, for example, in the PR (pathogenesis-related) protein genes of tobacco and are inducible by means of chemical regulators.

The regulatable DNA sequences mentioned by way of example above may be of both natural and synthetic origin, or they may comprise a mixture of natural and synthetic DNA sequences.

It is also advantageous for the expressible DNA, but especially the structural gene that is to be inserted, to comprise a sequence that codes for an N-terminal signal peptide capable of functioning in the plant cell, or to be linked in the 5'-terminal region to such a sequence. That signal peptide is a transport signal that is found at the N-terminal end of proteins transported via the endomembrane system. This signal sequence ensures that the said proteins first pass into the endoplasmic reticulum, where the signal peptide is split off proteolytically from the precursor protein as soon as it has fulfilled its function. By virtue of its specific function, this type of signal peptide sequence has been conserved to a high degree during evolution in all living cells, irrespective of whether they are bacteria, yeasts, fungi, animals or plants.

Moreover, the DNA molecule may comprise further sections of sequence that code for peptide fragments which as a whole contribute towards improving the competence for admission into the vacuole, for example the propeptide fragment discovered by Matsuoka K and Nakamura K in the N-terminal extension of sporamine [Matsuoka K and Nakamura K (1991)].

The present invention therefore also includes chimaeric genetic constructions that comprise, in addition to the targeting sequence according to the invention present in operable linkage with a structural gene or any other expressible DNA sequences, further regulatory sections of DNA sequence permitting, for example, specifically controlled induction or repression of gene expression.

The various sections of sequence can be linked to one another by methods known per se to form a complete coding DNA sequence. Suitable methods include, for example, the in vivo recombination of DNA sequences having homologous sections and the in vitro linking of restriction fragments.

As cloning vectors there are generally used plasmid or virus (bacteriophage) vectors having replication and control sequences originating from species that are compatible with the host cell.

The cloning vector generally carries an origin of replication, especially an origin of replication that is capable of functioning in *E. coli*, in Agrobacterium or in both, and, in addition, specific genes that lead to phenotypic selection features in the transformed host cell, especially to resistance to antibiotics or to specific herbicides. The transformed vectors can be selected on the basis of those phenotypic markers after transformation in a host cell.

Selectable phenotypic markers that may be used within the scope of this invention include, for example, resistance to ampicillin, tetracycline, hygromycin, kanamycin, methotrexate, G418 and neomycin, but this list, which is given by way of example, is not intended to limit the subject of the invention.

Suitable host cells within the scope of this invention are prokaryotes, including bacterial hosts, for example *A. tumefaciens, E. coli, S. typhimurium* and *Serratia marcescens*, and also cyanobacteria. Eukaryotic hosts, such as yeasts, mycelium-forming fungi and plant cells, may also be used within the scope of this invention.

The splicing of the hybrid gene construction according to the invention into a suitable cloning vector is carried out using standard methods, such as those described, for example, in Maniatis et al (1982).

As a rule, the vector and the DNA sequence to be spliced in are first cleaved with suitable restriction enzymes. Suitable restriction enzymes are, for example, those that yield fragments having blunt ends, for example SmaI, HpaI and EcoRV, or enzymes that form cohesive ends, for example EcoRI, SacI and BamHI.

Both fragments having blunt ends and those having cohesive ends that are complementary to one another can be linked again using suitable DNA ligases to form a continuous uniform DNA molecule.

Blunt ends can also be produced by treatment of DNA fragments that have projecting cohesive ends with the Klenow fragment of the *E. Coli* DNA polymerase to fill up the gaps with the corresponding complementary nucleotides.

On the other hand, cohesive ends can also be produced by artificial means, for example by the addition of complementary homopolymeric tails to the ends of a desired DNA sequence and of the cleaved vector molecule using a terminal deoxynucleotidyl transferase, or by the addition of synthetic oligonucleotide sequences (linkers) that carry a restriction cleavage site, and subsequent cleavage with the appropriate enzyme.

Within the scope of the present invention, in the construction of the chitinase mutants, various parts of the chitinase clones used are linked to one another. In order to be able to achieve this aim, those parts must be compatible, that is to say suitable restriction cleavage sites must be introduced into the various sequences. In a specific embodiment of this invention, therefore, the restriction cleavage sites listed below are preferably used, all of which lead to the same cohesive ends:

BamHI [G/GATCC]
BclI [T/GATCA]
BglII [A/GATCT]

The reading frame is in each case preferably so selected that GAT functions as the codon for aspartate.

The cloning vectors and the host cell transformed with those vectors are generally used to increase the number of copies of the constructs cloned therein. With an increased number of copies it is possible to isolate the vector carrying the hybrid gene construction and prepare it, for example, for insertion of the chimaeric gene sequence into a plant cell.

In a further process step, these plasmids are used to insert the structural genes coding for a desired gene product or non-coding DNA sequences having a regulatory function into a plant cell and, optionally, to integrate them into the plant genome.

The present invention therefore relates also to the production of recipient plant cells that comprise the said structural gene or other desirable genes or gene fragments or other useful DNA sequences incorporated in their genome.

The insertion of the chimaeric genetic construction is preferably carried out into plant protoplasts using known gene transfer processes.

A number of very efficient processes have come into existence for introducing DNA into plant cells, which processes are based on the use of gene transfer vectors or on direct gene transfer processes.

One possible method comprises, for example, bringing plant cells into contact with viruses or with Agrobacterium. This may be achieved by infecting sensitive plant cells or by co-cultivating protoplasts derived from plant cells. Within the scope of this invention, Cauliflower Mosaic Virus (CaMV) may also be used as a vector for the insertion of the chimaeric genetic construction according to the invention into a plant The total viral DNA genome of CaMV is integrated into a bacterial parental plasmid to form a recombinant DNA molecule that can be propagated in bacteria. After cloning has been carried out, the recombinant plasmid is cleaved, using restriction enzymes, either randomly or at very specific, non-essential sites within the viral part of the recombinant plasmid, e.g. within the gene that codes for the transferability of the virus by aphids, and the hybrid gene construction is cloned into that cleavage site.

A small oligonucleotide, a so-called linker, which has a single, specific restriction recognition site, may also be integrated. The recombinant plasmid so modified is cloned again and further modified by splicing the hybrid gene construction into a restriction site that occurs only once.

The modified viral portion of the recombinant plasmid can then be cut out of the bacterial parental plasmid and used for the inoculation of plant cells or of whole plants.

Another method of inserting the chimaeric gene construction into a cell makes use of the infection of the plant cell with *Agrobacteriun tumreaciens* and/or *Agrobacterium rhizogenes*, which has been transformed with the said gene construction. The transgenic plant cells are then cultured under suitable culture conditions known to the person skilled in the art, so that they form shoots and roots and whole plants are finally formed.

A further possible method of transforming plant material comprises mixed infection using both *Agrobacterium rhizogenes* and transformed *Agrobacterium tunefaciens*, as described by Petit et al (1986) for the transformation of carrots. The mixing ratio must be such that the rootlet colonies formed as a result of the *A. rhizogenes* transformation also comprise a high proportion of *A. tumefaciens* Ti-plasmids. This may be achieved, for example, by applying *A. rhizogenes* and *A. tumefaciens* together to the plant material in known manner in a mixing ratio of from 1:1 to 1:100, but preferably in a mixing ratio of 1:10. The transgenic plants are then cultured under suitable culture conditions known to the person skilled in the art, so that they form shoots and roots and whole plants are fully formed. Advantageously, the two Agrobacteriun species are not mixed until shortly before the actual inoculation of the plant material to be transformed.

The chimaeric gene construction according to the invention can therefore be transferred into suitable plant cells by means of, for example, the Ti-plasmid of *Agrobacterium tumefaciens* or the Ri-plasmid of *Agrobacterium rhizogenes*. The Ti-plasmid or Ri-plasmid is transferred to the plant in the course of infection by Agrobacterium and integrated in stable manner into the plant genome.

Both Ti-plasmids and Ri-plasmids have two regions that are essential for the production of transformed cells. One of those regions, the transfer-DNA (T-DNA) region, is transferred to the plant and leads to the induction of tumours. The other region, the virulence-imparting (vir) region, is essential only for the formation of the tumours, not for their maintenance.

The dimensions of the transfer-DNA region can be enlarged by incorporation of the chimaeric gene construction without the transferability being impaired. By removing the tumour-inducing genes and incorporating a selectable marker, the modified Ti- or Ri-plasmid can be used as a vector for the transfer of the gene construction according to the invention into a suitable plant cell.

The vir region brings about the transfer of the T-DNA region of Agrobacterium to the genome of the plant cell irrespective of whether the T-DNA region and the vir region are present on the same vector or on different vectors within the same Agrobacterium cell. A vir region on a chromosome also induces the transfer of the T-DNA from a vector into a plant cell.

Within the scope of this invention, therefore, there is preferably used a system for transferring a T-DNA region of Agrobacterium into plant cells, in which system the vir region and the T-DNA region are located on different vectors. Such a system is known as a "binary vector system", and the vector containing the T-DNA is accordingly designated a "binary vector".

Any T-DNA-containing vector that can be transferred into plant cells and permits selection of the transformed cells is suitable for use within the scope of this invention.

Especially preferred within the scope of this invention is a shuttle vector that comprises the chimaeric genetic construction according to the invention cloned in between the left border sequence (LB) and the right border sequence (RB) and that is capable of stable replication both in *E. coli* and in *A. tumefaciens*.

Using newly developed transformation techniques, it has also become possible in principle to transform in vitro plant species that are not natural host plants for Agrobacterium. For example, monocotyledonous plants, especially the cereal species and various grasses, are not natural hosts for Agrobacteriun.

It has become increasingly evident that monocotyledons can also be transformed using Agrobacteriun, so that, using new experimental formulations that are now becoming available, cereals and grass species are also amenable to transformation [Grimsley NH et al (1987)].

Preferred within the scope of this invention is so-called leaf disk transformation using Agrobacteriwn [Horsch et al (1985)]. Sterile leaf disks from a suitable target plant are incubated with Agrobacterium cells comprising one of the chimaeric gene constructions according to the invention, and are then transferred into or onto a suitable nutrient medium. Especially suitable, and therefore preferred within the scope of this invention, are LS media that have been solidified by the addition of agar and enriched with one or more of the plant growth regulators customarily used, especially those selected from the group of the auxins consisting of α-naphthylacetic acid, picloram, 2,4,5-trichlorophenoxyacetic acid, 2,4-dichlorophenoxyacetic acid, indole-3-butyric acid, indole-3-lactic acid, indole-3-succinic acid, indole-3-acetic acid and p-chlorophenoxyacetic acid, and from the group of the cytokinins consisting of kinetin, 6-benzyladenine, 2-isopentenyladenine and zeatin. The preferred concentration of auxins and cytokinins is in the range of from 0.1 mg/l to 10 mg/l.

After incubation for several days, but preferably after incubation for 2 to 3 days at a temperature of from 20° C. to 40° C., preferably from 23° C. to 35° C. and more especially at 25° C. and in diffuse light, the leaf disks are transferred to a suitable medium for the purpose of shoot induction. Especially preferred for the selection of the transformants is an LS medium that does not contain auxin but contains cytokinin instead, and to which a selective substance has been added. The cultures are kept in the light and are transferred to fresh medium at suitable intervals, but preferably at intervals of one week. Developing green shoots are cut out and cultured further in a medium that induces the shoots to form roots. Especially preferred within the scope of this invention is an LS medium that does not contain auxin or cytokinin but to which a selective substance has been added for the selection of the transformants.

In addition to Agrobacterium-mediated transformation, within the scope of this invention it is possible to use direct transformation methods for the insertion of the gene constructions according to the invention into plant material.

For example, the genetic material contained in a vector can be inserted directly into a plant cell, for example using purely physical procedures, for example by microinjection using finely drawn micropipettes [Neuhaus et al (1987)] or by bombarding the cells with microprojectiles that are coated with the transforming DNA ["Microprojectile Bombardment"; Wang Y-C et al (1988)].

Other possible methods for the direct transfer of genetic material into a plant cell comprise the treatment of protoplasts using procedures that modify the plasma membrane, for example polyethylene glycol treatment, heat shock treatment or electroporation, or a combination of those procedures [Shillito et al (1985)].

In the electroporation technique, plant protoplasts together with plasmids that comprise the hybrid gene construction are subjected to electrical pulses of high field strength. This results in a reversible increase in the permeability of biomembranes and thus allows the insertion of the plasmids. Electroporated plant protoplasts renew their cell wall, divide and form callus tissue. Selection of the transformed plant cells can take place with the aid of the above-described phenotypic markers.

A further method for the direct introduction of genetic material into plant cells, which is based on purely chemical procedures and which enables the transformation to be carried out very efficiently and rapidly, is described in Negrutiu I et al (1987) and in Goodall G et al.

Also suitable for the transformation of plant material is direct gene transfer using co-transformation (Schocher RJ et al 1986).

Co-transformation is a method that is based on the simultaneous taking up and integration of various DNA molecules (non-selectable and selectable genes) into the plant genome and that therefore allows the detection of cells that have been transformed with non-selectable genes.

The list of possible transformation methods given above by way of example does not claim to be complete and is not intended to limit the subject of the invention in any way.

Those cell clones which comprise the hybrid gene construction incorporated in their genome are selected using customary selection, screening and detection methods and are used for the regeneration of transgenic plants.

The regeneration of protoplasts kept in culture to form whole plants is described, for example, in Potrykus I and Shillito RD (1986).

The regeneration processes differ from one plant species to another. In general, however, the protoplasts, in one of the known culture media, are stimulated to divide and form cell walls. There are finally formed callus cultures which can be induced to form roots or shoots by treatment with specific active agents, for example auxins and cytokinins.

The plantlets so obtained can then be transferred to soil and cultivated further in the same manner as normal seedlings.

Efficient regeneration depends especially upon the medium, the genotype and the previous history of the culture. If these three variables are adequately controlled, the regeneration is completely reproducible and repeatable.

The regenerated transgenic plants, which comprise a structural gene, expressible in the plant cell, of the above-described hybrid gene construction as an integral component of the plant genome, can be propagated vegetatively, preferably in the form of sterile shoot cultures.

The stable integration of an operative expressible gene into the plant genome of the regenerated transgenic plants is verified by reference to the mitotic stability of the integrated gene and on the basis of its behaviour as Mendelian characteristic during meiosis and using Southern blot analysis (Southern EM, 1975).

The broad concept of this invention therefore also includes transgenic plant material, selected from the group consisting of protoplasts, cells, calli, tissues, organs, seeds, embryos, pollen, ovules, zygotes, etc. and, especially, whole, fertile plants, that has been transformed by means of the processes described above and comprises the recombinant DNA according to the invention in expressible form, and processes for the production of the said transgenic plant material.

The process for the production of transformed plant material comprising a gene product that is directed specifically into the plant vacuole essentially comprises:

(a) first of all isolating from a suitable source or synthesising by means of known processes the DNA sequence responsible for specifically directing into the vacuole;

(b) inserting the said DNA sequence in operable manner into the 3'-terminal end of any desired expressible DNA sequence;

(c) cloning the finished construct into a plant expression vector under the control of expression signals active in plants; and (d) transforming the said expression vector into plant material by means of known processes and expressing it therein.

If the DNA to be expressed is not a structural gene that naturally codes for an N-terminal signal peptide, it is advantageous operably to insert into the 5'-terminal region of the DNA to be expressed additionally a DNA sequence that does code for such a signal peptide.

Also included in the present invention is a process for the production of transformed plant material comprising a gene product that is secreted specifically into the extracellular space, which process essentially comprises:

(a) isolating a DNA sequence coding for such a gene product;

(b) removing from the C-terminal end the targeting sequence responsible for directing into the particular cellular compartment;

(c) splicing the said deleted DNA sequence into a suitable plant expression vector, and (d) transforming the finished construct into plant material.

Within the scope of this invention, preference is given to transgenic plants, including their sexual and asexual progeny, that can be regenerated from plant material selected from the group consisting of protoplasts, cells, calli, tissues, organs, seeds, embryos, pollen, ovules, zygotes, etc. and comprise one of the recombinant DNA molecules according to the invention.

Preference is also given to transgenic plants, including their sexual and asexual progeny, that have a significantly increased protein content in the plant vacuole and/or in the extracellular space in comparison with the wild type.

Special preference is given to transgenic plants, including their sexual and asexual progeny, that have a significantly increased chitinase content in the plant vacuole in comparison with the wild type.

Special preference is given also to transgenic plants, including their sexual and asexual progeny, that have a significantly increased chitinase content in the extracellular space of the plant in comparison with the wild type.

The expression "asexual and/or sexual progeny of transgenic plants", as defined within the scope of this invention, therefore also includes all mutants and variants that can be obtained by means of known processes, for example by cell fusion or mutant selection, and that still have the characteristic properties of the transformed starting plant, and all hybridisation and fusion products obtained using the transformed plant material.

This invention relates also to the propagation material of transgenic plants.

Within the scope of this invention, propagation material of transgenic plants is to be understood as being any plant material that can be propagated sexually or asexually and in vivo or in vitro. Propagation material that is to be regarded as especially preferred within the scope of this invention is especially protoplasts, cells, calli, tissue, organs, seeds, embryos, pollen, ovules and zygotes, as well as any other propagation material that can be obtained from transgenic plants.

This invention relates also to parts of plants, for example blossoms, stems, fruits, leaves and roots, that originate from transgenic plants or their progeny that have been previously transformed by means of the process according to the invention and are therefore made up at least partially of transgenic cells.

The process according to the invention is suitable for the transformation of all plants, especially those of the systematic groups Angiospermae and Gymnospermae.

Of the Gymnospermae, the plants of the Coniferae class are of special interest.

Of special interest among the Angiospermae are, in addition to deciduous trees and shrubs, plants of the families Solanaceae, Cruciferae, Compositae, Liliaceae, Vitaceae, Chenopodiaceae, Rutaceae, Alliaceae, Amaryllidaceae, Asparagaceae, Orchidaceae, Palmae, Bromeliaceae, Rubiaceae, Theaceae, Musaceae, Malvaceae or Gramnineae and of the order Leguminosae and, of these, especially the Papilionaceae family. Representatives of the Solanaceae, Cruciferae and Gramineae families are preferred Target crops within the scope of the present invention also include, for example, those selected from the series: Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicun, Datura, Hyoscywnus, Lycopersion, Nicotiana, Solanum, Petunia, Digitalis, Majorana, Cichorium, Helianthus, Lactuca, Bromus, Gossypium, Asparagus, Antirrhinun, Hemerocallis, Nemesia, Pelargonium, Panicum, Pennisetum, Ranunculus, Senecio, Salpiglossis, Cucumis, Browallia, Glycine, Lolium, Zea, Triticum, Sorghun, Ipomoea, Passiflora, Cyclamen, Malus, Prunus, Rosa, Rubus, Populus, Santalum, Allium, Lilium, Narcissus, Ananas, Arachis, Phaseolus and Pisum.

Owing to new developments in the field of the in vitro culture of plants, especially in the field of plant regeneration, it has now become possible, even with representatives of the Gramineae family, to regenerate whole plants starting from plant protoplasts. Examples of successful regeneration experiments with Gramineae are described, inter alia, in Yamada Y et al (1986) for rice protoplasts, in Rhodes et al (1988) and Shillito RD et al (1989) for maize protoplasts, and in Horn et al (1988) for *Dacrylis glomerata* protoplasts.

Within the scope of the present invention it is therefore possible to use also the following plants: Lolium, Zea, Triticum, Sorghum, Saccharum, Bromus, Oryzae, Avena, Hordeum, Secale and Setaria.

Accordingly, this invention relates preferably also to transgenic plants from the group of the Graminaceae, including their sexual and asexual progeny, that can be regenerated from plant material selected from the group consisting of protoplasts, cells, calli, tissues, organs, seeds, embryos, pollen, ovules, zygotes, etc. and that comprise one of the recombinant DNA molecules according to the invention.

The mature plants that have been raised from transformed plant cells are crossed with themselves to produce seed. Some of the seeds contain the genes that code for a useful and desirable property in a ratio that obeys exactly the established laws of heredity. These seeds can be used for the production of transgenic plants.

Homozygotic lines can be obtained by repeated self-pollination and the production of inbred lines. These inbred lines can then be used in turn for the development of hybrids. In this process an inbred line that comprises the said foreign gene is crossed with another inbred line for the purpose of production.

After the general description of the present invention, for the purpose of better understanding reference will now be made to specific Examples which are incorporated into the description for illustrative purposes and are not of a limiting nature unless there is a specific indication to the contrary.

In the specific embodiment of the present invention described in detail below, a basic chitinase and an unrelated class III chitinase [cucumber chitinase], which is naturally secreted into the extracellular space and has no homology with class I or II chitinases, with and without the targeting sequence according to the invention are expressed in *Nicotiana sylvestris* plants, and their localisation within the plant cell is determined.

The necessity of the C-terminal extension of the proteins present naturally in the vacuole for target-oriented localisation into the vacuole and for the possibility in principle of discharging the said proteins specifically into the extracellular space can be demonstrated by means of a basic chitinase and a basic glucanase from tobacco. To that end, the 7 or 22 C-terminal amino acids forming the C-terminal extension of these proteins present naturally in the vacuole are removed or inactivated by placing a suitable stop codon at the appropriate site within the coding sequence by means of oligonucleotide-mediated mutagenesis. This subsequently results in the mutated chitinase or glucanase being discharged into the extracellular space.

In order to demonstrate, on the other hand, that the said targeting sequence according to the invention is also capable of directing an associated protein molecule specifically into the vacuole, the C-terminal sequence of a basic chitinase from tobacco is linked to an acidic chitinase from cucumber leaves. The procedure is as follows: first of all the 5' non-coding sequence from a basic tobacco chitinase and the sequence, likewise located in that region, coding for a signal peptide are linked to the sequence coding for the mature cucumber chitinase. The 3' end of that construct is then added via a linker fragment to a sequence coding for 9 amino acids from the C-terminal extension of the tobacco chitinase gene.

The above-described constructs are then brought under the control of a strong CaMV 35S promoter and inserted into *Nicotiana sylvestris* plants by means of Agrobacterium transformation.

When the transformation has been carried out, transgenic plants that exhibit a strong chitinase expression are selected and used for analysing the localisation of the chitinase. Protoplasts are produced and the specific activities of the chitinase in the homogenates and the protoplasts are compared.

For the purpose of determining the subcellular localisation of the intracellular chitinase, vacuoles are isolated from protoplasts.

NON-LIMITING EXAMPLES

General Recombinant DNA Techniques

Since many of the recombinant DNA techniques employed in this invention are a matter of routine for the person skilled in the art, it is better to give a short description of these generally used techniques here rather than to describe them every time they occur. Except where there is a specific indication to the contrary, all these procedures are described in the Maniatis et al (1982) reference.

A. Cleaving with Restriction Endonucleases

A reaction batch typically contains about 50 to 500 $\mu$g/ml of DNA in the buffer solution recommended by the manufacturer, New England Biolabs, Beverly, Mass. 2 to 5 units of restriction endonucleases are added for each $\mu$g of DNA and the reaction batch is incubated for from one to three hours at the temperature recommended by the manufacturer. The reaction is terminated by heating at 65° C. for 10 minutes or by extraction with phenol, followed by precipitation of the DNA with ethanol. This technique is also described on pages 104 to 106 of the Maniatis et al (1982) reference.

B. Treatment of DNA with Polymerase in Order to Produce Blunt Ends 50 to 500 $\mu$g/ml of DNA fragments are added to a reaction batch in the buffer recommended by the manufacturer, New England Biolabs. The reaction batch contains all four deoxynucleotide triphosphates in concentrations of 0.2 mM. The reaction takes place over a period of 30 minutes at 15° C. and is then terminated by heating at 65° C. for 10 minutes. For fragments obtained by cleaving with restriction endonucleases that produce 5'-projecting ends, such as EcoRI and BamHI, the large fragment, or Klenow fragment, of DNA polymerase is used. For fragments obtained by means of endonucleases that produce 3'-projecting ends, such as PstI and SacI, the T4 DNA polymerase is used. The use of these two enzymes is described on pages 113 to 121 of the Maniatis et al (1982) reference.

C. Agarose Gel Electrophoresis and Purification of DNA Fragments from Gels

Agarose gel electrophoresis is carried out in a horizontal apparatus, as described on pages 150 to 163 of the Maniatis et al reference. The buffer used is the tris-borate buffer described therein. The DNA fragments are stained using 0.5 $\mu$g/ml of ethidium bromide which is either present in the gel or tank buffer during electrophoresis or is added after electrophoresis. The DNA is made visible by illumination with long-wave ultraviolet light. If the fragments are to be separated from the gel, an agarose is used that gels at low temperature and is obtainable from Sigma Chemical, St. Louis, Mo. After the electrophoresis, the desired fragment is cut out, placed in a plastics test tube, heated at 65° C. for about 15 minutes, extracted three times with phenol and precipitated twice with ethanol. This procedure is slightly different from that described by Maniatis et al (1982) on page 170.

As an alternative, the DNA can be isolated from the agarose with the aid of the Geneclean kit (Bio 101 Inc., La Jolla, Calif., USA).

D. Addition of Synthetic Linker Fragments to DNA Ends

If it is desired to add a new endonuclease cleavage site to the end of a DNA molecule, the molecule is optionally first treated with DNA-polymerase in order to produce blunt ends, as described in the section above. About 0.1 to 1.0 $\mu$g of this fragment is added to about 10 ng of phosphorylated linker DNA, obtained from New England Biolabs, in a volume of 20 to 30 $\mu$l with 2 $\mu$l of T4 DNA ligase from New England Biolabs, and 1 mM ATP in the buffer recommended by the manufacturer. After incubation overnight at 15° C., the reaction is terminated by heating at 65° C. for 10 minutes.

The reaction batch is diluted to about 100 $\mu$l in a buffer appropriate for the restriction endonuclease that cleaves the synthetic linker sequence. About 50 to 200 units of this endonuclease are added. The mixture is incubated for 2 to 6 hours at the appropriate temperature, then the fragment is subjected to agarose gel electrophoresis and purified as described above. The resulting fragment will then have ends with endings that were produced by cleaving with the restriction endonuclease. These ends are usually cohesive, so that the resulting fragment can then readily be linked to other fragments having the same cohesive ends.

E. Removal of 5'-terminal Phosphates from DNA Fragments

During the plasmid cloning steps, treatment of the vector plasmid with phosphatase reduces the recircularisation of the vector (discussed on page 13 of the Maniatis et al reference). After cleavage of the DNA with the correct restriction endonuclease, one unit of calf intestinal alkaline phosphatase obtained from Boehringer-Mannheim, Mannheim, is added. The DNA is incubated at 37° C. for one hour and then extracted twice with phenol and precipitated with ethanol.

F. Linking of DNA Fragments

If fragments having complementary cohesive ends are to be linked to one another, about 100 ng of each fragment are incubated in a reaction mixture of 20 to 40 $\mu$l containing about 0.2 unit of T4 DNA ligase from New England Biolabs in the buffer recommended by the manufacturer. Incubation is carried out for 1 to 20 hours at 15° C. If DNA fragments having blunt ends are to be linked, they are incubated as above except that the amount of T4 DNA ligase is increased to 2 to 4 units.

G. Transformation of DNA into *E. coli*

*E. coli* strain HB101 is used for most of the experiments. DNA is introduced into *E. coli* using the calcium chloride method, as described by Maniatis et al (1982), pages 250 and 251.

H. Screening of *E. coli* for Plasmids

After transformation, the resulting colonies of *E. coli* are tested for the presence of the desired plasmid by means of a rapid plasmid isolation process. Two customary processes are described on pages 366 to 369 of the Maniatis et al (1982) reference.

I. Large-scale Isolation of Plasmid DNA

Processes for the isolation of plasmids from *E. coli* on a large scale are described on pages 88 to 94 of the Maniatis et al (1982) reference.

J. Cloning in M13 Phage Vectors

In the following description it is to be understood that the double-stranded replicative form of the phage M13 derivatives is used for routine processes, such as cleaving with restriction endonuclease, linking etc.

Unless there is a specific indication to the contrary, enzymes can be obtained from Boehringer, Biolabs (BRL). They are used in accordance with the manufacturer's instructions unless otherwise indicated.

K. Southern Blot Analysis

The extracted DNA is first treated with restriction enzymes, then subjected to electrophoresis in a 0.8% to 1% agarose gel, transferred to a nitrocellulose membrane [Southern EM (1975)] and hybridised with the DNA to be detected which has previously been subjected to nick-translation (DNA-specific activities of $5 \times 10^8$ to $10 \times 10^8$ c.p.m./$\mu$g). The filters are washed three times for 1 hour each time with an aqueous solution of 0.03M sodium citrate and 0.3M sodium chloride at 65° C. The hybridised DNA is made visible by blackening an X-ray film over a period of 24 to 48 hours.

L. Western Blot Analysis

After SDS-polyacrylamide gel electrophoresis, the proteins are transferred electrophoretically to a nitrocellulose or nylon filter. This filter is then first pre-treated with a blocking agent (for example 5% skim milk powder in PBS: milk/PBS). The filter is then incubated for several hours with an antiserum that reacts with the compound to be detected (in the present case: chitinase). The filter pre-treated in this manner is washed several times with milk/PBS and then incubated with a commercially available secondary antibody that is coupled to an enzyme [for example peroxidase-coupled goat anti-rabbit antibody (BIORAD), 1:2000 diluted in milk/PBS]. The filter is again washed in PBS and then stained with chloronaphthol and hydrogen peroxide in accordance with the manufacturer's [BIORAD] instructions. Further details are given in Sambrook et al (1989).

M. General Techniques for the Generation, Purification and Automatic Sequencing of Peptides.

Reduction and alkylation: Purified, lyophilised protein is dissolved in 6M guanidine hydrochloride containing 1M tris-HCl (pH 8.6) and 10 mM EDTA. Dithiothreitol (DDT) is added to a final concentration of 20 mM, and 4-vinylpyridine is added to a final concentration of 50 mM. This batch is then incubated under nitrogen for 1.5 hours. The pyridylethylated material is then freed of salt by means of HPLC [Aquapore phenyl column (2.1×10 cm, Brownlee)]. The column is eluted with a linear gradient, extending from 5% to 80%, of an acetonitrile:isopropanol mixture (1:1) in 0.1% trifluoroacetic acid (TFA).

Cyanogen bromide cleavage and digestion with pyroglutamate aminopeptidase: Cyanogen bromide cleavage is carried out in situ according to Simpson and Nice (1984). Digestion with pyroglutamate aminopeptidase [Boehringer Mannheim] can be carried out according to Allen (1981).

LysC digestion: Protein is digested with endoproteinase Lys-C [Boehringer Mannheim] in 0.1M tris-HCl (pH 8.5) over a period of 24 hours at room temperature, using an enzyme:substrate ratio of 1:10. The resulting peptides are isolated by means of HPLC [Aquapore C-8 column (1×22 cm, Brownlee)]. A linear acetonitrile:isopropanol (1:1) gradient (0% to 60%) in 0.1% TFA is used as eluant.

Trypsin digestion: Digestion of protein with trypsin [Cooper] is carried out in 0.1M ammonium bicarbonate (pH 8.2) containing 0.1M calcium chloride at a temperature of 37° C. and an enzyme:substrate ratio of 1:100. The duration of incubation is 5 hours. The resulting peptides are separated by means of HPLC [see Section C above].

As an alternative to the above, the digestion may be carried out using an enzyme:substrate ratio of 1:50 in 0.1M tris-HCl (pH 8.5) at a temperature of 37° C. In that case, the duration of incubation is 24 hours. The resulting peptides are separated by means of HPLC [Vydac C-18 column (2.1×150 mm)] using a linear (0% to 60%) acetonitrile: isopropanol (1:1) gradient in 0.1% TFA.

Seguencing: Automated Edman degradation is carried out with the aid of an Applied Biosystems 470A gas phase sequencer. Identification of the phenylthiohydantoin (PTH) amino acids is carried out using an Applied Biosystems 129A PTH analyser.

For the purpose of illustrating the rather general description and for better understanding of the present invention, reference will now be made to specific Examples which are not of a limiting nature unless there is a specific indication to the contrary. The same applies also to all lists given by way of example in the above description.

I. Production of cDNA and Genomic Gene Libraries from Tobacco

Example 1 Plant Material

*Nicotiana tabuacum* L. c.v. Havana 425 plants are raised either in a greenhouse or starting from surface-sterilised seed. Surface-sterilisation of the seeds is carried out as follows: 20 to 30 seeds are put into a sieve having a pore size of about 200 $\mu$m and incubated in 10 ml of a 10% commercially available bleach solution (NaOCl). The seeds are then rinsed repeatedly with sterile distilled water.

In the following Examples there is preferably used a cloned line of parenchymatous pith tissue (N) which can be isolated from *Nicotiana tabuacum* L. c.v. Havana 425 plants in accordance with Eichholz et al (1983).

Example 2 Tissue Culture

Tobacco tissue is cultured on a basic medium that has a salt and thiamine hydrochloride concentration according to Linsmeier and Skoog (1965) (LS) and that has been solidified by the addition of 10 g/l of agar. As a further additive, this basic medium comprises a pH indicator, for example 5 mg/l of chlorophenol red. Other media that are based on this LS basic medium and that are used in subsequent Examples comprise as further additives, for example, kinetin (1.4 $\mu$M) [cytokinin medium] or a-naphthylacetic acid (10.7 $\mu$M) [auxin medium] or a mixture of kinetin and a-naphthylacetic acid [auxin/cytokinin medium (medium A)].

The selective media B and C do not contain a-naphthylacetic acid, but instead contain a selective substance by means of which the transformants can be selected from the large number of untransformed cells and tissue. The precise composition of these selective media is given in Section VII (media).

The strain line (275N) isolated from *Nicotiana tabuacum* L. c.v. Havana 425 plants is subcultured at 21-day intervals on an auxin/cytokinin medium (10 ml), that is to say it is each time inoculated onto new medium (10 ml) and cultured at 25° C. in the light.

For the induction of high levels of chitinase in the cultured tissues, the tissues are inoculated from the auxin/cytokinin medium onto a hormone-free basic medium. Further details relating to the culturing of plant tissues and the induction of chitinase are described in Felix and Meins (1985).

Example 3 Production of Tobacco Protoplasts 100 ml of a 2-day-old tobacco cell suspension according to Example 1 are mixed with an equal volume of a double-concentrated enzyme solution. The enzyme solution comprises the following constituents:

| | |
|---|---|
| cellulase R.10 Onozuka/ (Yakult Honsha, Tokyo, Japan) | 10.0 g/l |
| macerase (pectinase from Rhizopus sp., Behring Diagnostics, La Jolla, CA) | 2.5 g/l |
| pectolyase Y-23/ (Seishin Pharm. Co., Tokyo, Japan) | 1.0 g/l |
| $CaNO_3.4H_2O$ | 1.45 g/l |
| $MgSO_4.7H_2O$ | 0.5 g/l |
| $NH_4H_2PO_4$ | 0.23 g/l |
| $KNO_3$ | 1.2 g/l |
| D-mannitol (pH 5.70) | 73.0 g/l |

The above enzyme solution is centrifuged and sterilised through a 0.2 mm filter. The batch consisting of the tobacco suspension culture and the enzyme solution is agitated carefully on a rotary shaker (40 rpm) for 5 hours at room temperature. At specific time intervals samples are taken from this batch and analysed microscopically. The enzymatic digestion is continued until about 80% of the cells have changed into spherical protoplasts. The incubation vessels are then removed from the shaker. The cell/protoplast suspension is allowed to settle and the upper half of the medium, which does not contain cells or protoplasts, is removed by suction with a pipette and discarded. The remainder is transferred to 50 ml centrifuge tubes and centrifuged for 10 minutes at 500 rpm in a clinical centrifuge (model HN-SII, IEC). The protoplast-containing pellets are resuspended in rinse I solution [see Section VII] and then centrifuged again for 10 minutes at 1000 rpm.

The band containing the protoplasts is located at the upper rim of the centrifuge tube. The protoplast fraction is collected and then washed again in rinse I solution. The protoplasts are returned to a centrifuge tube and stored in ice until required for further use.

Example 4 Construction of a cDNA Gene Library

A cDNA gene library is produced starting from poly(A)+ RNA, which can be obtained from a cloned line of parenchymatous pith tissue of *Nicotiana tabuacum* L. c.v. Havana 425 plants (see Example 1). The tobacco tissue is first stimulated to produce high levels of chitinase in accordance with Example 2 by culturing the tissue on a hormone-free LS basic medium.

4.1. Isolation of Total RNA

The preparation of total RNA is effected substantially in accordance with the method described in Lagrimini LM et al (1987).

Tobacco tissue deep-frozen in liquid nitrogen is first pounded coarsely in a mortar and then placed in a suitable homogenisation buffer [(1) 7.56M guanidine hydrochloride, 0.73M mercaptoethanol, 18.9 mM sodium acetate pH 5.0; or (2) 4% (w/v) SDS, 0.1M tris-HCl pH 7.8 (1 part by volume) +80% phenol (v/v), 0.1% (w/v) hydroxyquinoline, 0.1M tris-HCl pH 7.8 (1 part by volume); or (3) according to Lagrimini LM et al (1987)] (2.5 ml of buffer per gram of tissue). After the addition of an equal part by volume of phenol, the batch is homogenised, for example in a Polytron homogeniser. A half volume of chloroform is then added and the emulsion is mixed carefully for about 15 minutes. The various phases are then separated from one another by centrifugation (10 400 g for 10 minutes); the aqueous phase is discarded. At this point it is possible, if desired, to add further extraction steps, for example in the form of an additional phenolchloroform extraction or extraction twice with a mixture of phenol:chloroform:isoamyl alcohol (25:24:1). The extraction is followed by the precipitation step. This step is effected by the addition of 0.3M sodium acetate and 2.5 parts by volume of ethanol. The precipitate is collected by centrifugation (10 400 g for about 15 minutes) and resuspended in 2 ml of sterile water. After the addition of lithium chloride in a final concentration of 3M, the entire batch is incubated overnight at 4° C. The precipitate is then again collected by centrifugation and the pellet formed is washed with ice-cooled ethanol. The pellet is then dried and resuspended in 500 μl of sterile water. The concentration of total RNA in this preparation is determined by spectrophotometry.

As an alternative to the process described above, the total RNA can also be isolated from callus tissue. In this case too, the above-described process steps are used, but the starting material used is callus tissue cut into cubes (about 3 mm), which prior to the homogenisation step is first deep-frozen in liquid nitrogen and then pounded to a fine powder in a precooled mortar.

4.2. Isolation of Polyadenylated RNA

Poly(A)+ RNA is isolated by means of oligo-d(T) cellulose chromatography (Collaborative Research, Lexington, Mass., USA) in accordance with methods known per se [see, for example, Mohnen (1979)].

Oligo-d(T) cellulose is first washed for 15 minutes in 20 parts by volume of 2.0M NaCl, then suspended in sterile water and packed into a column (1.5 cm in diameter and 20 cm in length). The column is washed with a buffer solution (440 mM NaCl, 0.9 mM EDTA, 9 mM tris-HCl, pH 7.5; or 0.5M NaCl, 10 mM tris-HCl, pH 7.5) until the eluate has a pH value of from 7.0 to 7.6. RNA solutions having an RNA content of from 0.6 mg to 6.0 mg of RNA in a volume of 4.0 ml are then adjusted to a final concentration of 1 mM EDTA and 10 mM piperazine-1,4-bis(2-ethanesulfonic acid), pH 7.5. The RNA is denatured by heating for 5 minutes at 70° C. and then cooling on ice. The entire solution is then adjusted to a value of 0.36M NaCl with 0.1 part by volume of 4M NaCl. The RNA solution is applied to the column and the non-polyadenylated RNA[poly(A)− RNA] is eluted with the above-mentioned buffer solution. The absorption of the eluates is determined by means of a spectrophotometer (Hitachi model 100-40, Hitachi, Tokyo, Japan) and a W+W recorder (Scientific Instruments, Basle, Switzerland) connected thereto. As soon as the absorption has reached the base line, the poly(A)+ RNA that is bound to the column is eluted with 1 mM EDTA, 10 mM tris-HCl pH 7.5. The eluates are introduced into a solution of 0.5 mM EDTA and 0.3M sodium acetate pH 5.0 and precipitated by the addition of 2.5 parts by volume of ethanol. The RNA is then collected by centrifugation at 83 000×g (30 to 45 minutes), dried under nitrogen and resuspended in 1 mM EDTA, 10 mM tris, pH 7.5 or in water.

4.3. Construction and Selection of cDNA Clones

Poly(A)+ RNA is separated into individual fractions by means of preparative ultracentrifugation (17 hours at 57 000 g) over a 5–25% (w/v) sucrose gradient (1 mM EDTA; 10 mM tris-HCl, pH 7.5). The fractions that comprise the information for chitinase can be identified by means of in vitro translation using anti-chitinase antibodies. These fractions are then combined and used for further working up.

The procedure for the production of anti-chitinase antibodies is known to the person skilled in the art and can be carried out, for example, in accordance with the method described in Shinshi et al (1985) and Mohnen (1985). In that method, essentially emulsions comprising purified chitinase preparations in complete Freund's adjuvant are injected into three-month-old female rabbits (New Zealand white rabbit). Further injections follow after one and two weeks and then at monthly intervals. Blood is taken 7 to 10 days after each injection, the serum samples being stored at −20° C. Immunoglobulin G is purified by means of affinity chromatography on a protein A-Sepharose C 1 4B column (Pharmacia), then lyophilised and stored at −20° C.

Synthesis of double-stranded DNA starting from the poly (A)+ RNA matrix, cloning of that double-stranded DNA in pBR322, differential colony hybridisation and plasmid isolation are carried out substantially in accordance with the instructions and description in Maniatis et al (1982).

For the synthesis of about 0.8 μg of double-stranded DNA, 3 μg of the poly(A)+ RNA previously isolated and enriched with chitinase mRNA are incubated with reverse transcriptase (Life Sciences, St. Petersburg, Fla.) and DNA polymerase I (New England Biolabs, Beverly, Mass.). The resulting cDNA is spliced into the PstI cleavage site of pBR322 by means of the homopolymeric dC-dG tailing method, which enables the cDNA and the vector DNA to be provided with complementary cohesive ends and which is described in detail in Maniatis et al (1982) [pages 217–219]. The PstI-linearised vector pBR322 provided with oligo-dC ends is available commercially.

The resulting recombinant plasmid is then used for the transformation of competent *E. coli* DH1 cells. The cloning in plasmids is described in detail in Maniatis et al (1982) on pages 242–246 and 391.

The cDNA library constructed in this manner, which is in the form of bacterial colonies on agar plates, is then first screened by means of differential colony hybridisation using radioactively labelled cDNA.

In the differential colony hybridisation, duplicates of the bacterial colonies are made on nitrocellulose filters by placing the filters on the agar plate and then carefully removing them again. The original agar plate is stored for later identification of positive colonies. Filters with adhering bacterial colonies are then placed on a nutrient medium and left there until the colonies have grown into clones approximately 2 mm in size. The filters are then treated with sodium hydroxide solution, which results in lysis of the bacterial cells and in denaturing and fixing of the bacterial DNA on the filter. After pH neutralisation, the filters are repeatedly washed, dried and finally "baked" at a temperature of 80° C. in vacua, so that the DNA is covalently bonded to the filters.

The filters are hybridised twice in succession with radioactively labelled (non-cloned) cDNA probes. These cDNA probes are poly(A)+ RNA from tobacco tissue which has previously been induced to produce chitinase (incubation for 7 days on a basal medium without hormone additives) and poly(A)+ RNA from non-induced tobacco tissue (incubation for 7 days on auxin/cytokinin medium). Promising cDNA clones that react more strongly with the cDNA from induced tissue than they do with the control DNA from non-induced tissue, are then subjected to further analysis using the "hybrid select" translation method in accordance with the method described in Mohnen et al (1985) and Mohnen (1985). The plasmid DNA is denatured by boiling for 1 minute in 0.2M–0.3M NaOH, 3M NaCl and then cooled on ice. The hybridisation reaction is carried out on square BA/85 nitrocellulose filters (Schleicher and Schuill, Dassel, FRG) using 200 μg to 250 μg of total RNA per filter. The RNA hybridised on the filters is eluted, precipitated with ethanol and dissolved in 10 μl of water and analysed with the aid of in vitro translation (using a commercially available wheatgerm extract). The radioactively labelled products are precipitated with antibodies to the desired protein and analysed by SDS-polyacrylamide gel electrophoresis.

4.4. cDNA Clone pCHN48

The cDNA gene library is screened in accordance with Maniatis et al (1982) using colony or plaque hybridisation. As DNA probe there is used the cDNA clone pCHN50 described in Shinshi et al (1987), which comprises the entire DNA sequence coding for the mature protein but lacks the complete N-terminal signal peptide sequence. In this manner, various clones of different lengths are obtained. The longest of these clones is selected and subjected to nucleotide sequence analysis. This clone, designated pCHN48, has a 1.14 kb insert having 7 adenosines at the poly(A) end, a single large reading frame (open reading frame) 987 nucleotides in length, corresponding to a polypeptide of 329 amino acids, and a nucleotide from the 5' untranslated region. The amino acid sequence derivable from the DNA sequence of the coding region tallies with the sequence for the first 20 N-terminal amino acids of known chitinases from tobacco.

Example 5 Construction of a Genomic Gene Library 5.1. Isolation of Chromosomal Tobacco DNA For the purpose of lysing the protoplasts, 100 ml of ice-cooled protoplast suspension are mixed with 400 ml of an ice-cooled TENP buffer (see Section VII). The nuclei are separated from this lysate by means of centrifugation for 10 minutes in an IEC clinical centrifuge at 2000 rpm. The pellet so obtainable is resuspended in 500 ml of ice-cooled TENP buffer and pelleted again as described above. Then 8 CsCl gradient test tubes are prepared; in each test tube a cell pellet comprising approximately 12.5 ml of protoplast suspension is added to 26 ml of tenfold concentrated TE buffer (see Section VII). For the purpose of lysing the cell nuclei, 5 ml of a 20% (w/v) sodium lauryl sarcosine solution and 32.2 g of CsCl and 2.89 ml of ethidium bromide solution (EtBr, 10 mg/ml) are added to the batch. The entire batch is stirred gently to dissolve the CsCl.

The lysates so obtained are transferred to polyallomer tubes (Beckman VTi50, 39 ml tubes) and centrifuged at 45 000 rpm and a temperature of 20° C. for 16 hours in a VTi50 rotor (Beckman). Bands that are fluorescent in UV light are removed from the gradient by means of 3 ml syringes with 16 gauge needles and collected. Further working up of the DNA is effected by repetition of the above-described CsCl/EtBr equilibrium centrifugation. The fluorescent bands are again collected and adhering EtBr is removed in six successive extraction steps using isopropanol saturated with 20×SSC (see Section VII) (equal volume). The DNA is precipitated from this gradient solution, purified in the manner described above, by adding in succession 2 parts by volume of distilled water, 0.1 part by volume of 3.0M sodium acetate, pH 5.4, and 2 parts by volume of ethanol. The filamentous DNA is wound up out of the solution using a Pasteur pipette, washed in 70% ethanol and further extracted with an equal part by volume of chloroform. The DNA is precipitated by the addition of 0.1 part by volume of 3M sodium acetate, pH 5.4, and 2.0 parts by volume of ethanol. The DNA filament is again wound up, washed in 70% ethanol and dried in the air for 5 minutes. It is then dissolved in a total volume of 7 ml of TE buffer (see Section VII) and stored at 4° C. until required for further use.

5.2. Construction of a Genomic 1 Gene Library

The previously isolated tobacco DNA is digested with the restriction enzyme Sau3A and separated for 20 hours by means of a 10%–40% sucrose gradient in an SW41 rotor (Beckman) at 20 000 rpm. The fractions obtainable from that gradient are analysed by means of gel electrophoresis (0.5% agarose gel in TBE buffer). Those fractions which contain fragments of the correct size are pooled. The DNA is precipitated using 1/10 part by volume of 3M sodium acetate (pH 4.8) and 2 parts by volume of ethanol, and ligated with BamHI-digested phosphatase-treated 1 EMBL3 DNA (Stratagen; La Jolla, Calif.). The linkage reaction is carried out in accordance with the manufacturer's instructions, there being used reaction batches of 5 μl that comprise 1 μg of 1-vector DNA and 0.1 μg of the tobacco DNA to be incorporated. The incorporation of the DNA resulting from this linkage reaction into the heads of 1-phages is carried out using the Gigapack Plus kit by Stratagen in accordance with the manufacturer's instructions. The phage yield after infection of E. coli CES201 (Glover DM) is approximately $2 \times 10^6$ phages per μg of inserted DNA.

5.3. Screening of the Gene Libraries and Isolation of Genomic Clones

The genomic gene library is screened in accordance with Maniatis et al (1982) using colony or plaque hybridisation. The cDNA clone pCHN50 described in Shinshi et al (1987) and the clone pCHN48 isolated in Section 4.4. are used as DNA probe.

The recombinants obtainable in this manner are purified and partially characterised using Southern blot analysis. One of these clones, which has a very strong hybridisation signal with the cDNA probe molecules pCHN50 and pCHN48 and, according to Southern blot analysis, comprises the complete chitinase gene, is selected for further tests and is designated 1CHN17.

Example 6 The Genomic Tobacco Chitinase Clone 1CHN17

6.1 DNA Sequencing and Sequence Analysis

After digestion with the restriction enzyme HindIII there is obtained a 5.4 kb DNA fragment which comprises the complete chitinase gene and correlates with a fragment of the same size from tobacco DNA. A portion of this fragment, which comprises 3850 bp and contains the entire coding sequence, is then sequenced.

Restriction fragments are cloned in suitable cloning vectors, for example M13mp18 or M13mp19 [Yanisch-Perron et al (1985)], and sequenced in both directions by means of the dideoxynucleotide method ["Dideoxynucleotide chain-termination method"; Sanger et al (1977)]. The nucleotide and amino acid sequences determined are analysed further by computer using Genetics Computer Group software [Devereux et al (1984)].

The complete DNA sequence of the basic chitinase gene from tobacco, which is designated gene 48, is shown in SEQ ID NO: 10. A comparison of that sequence with the cDNA clones pCHN48 and pCHN50 makes it clear that within the coding region of gene 48 there are two intervening sections of sequence (introns). The first of these introns comprises 274 bp and is located between the first and second nucleotides of codon 148, which codes for glycine. The second intron is 269 bp in length and is located between the second and third nucleotides of codon 199, which codes for histidine. Both introns, in line with other known plant and animal introns, have consensus splicing sites which have a donor and an acceptor sequence (<u>GT</u>AAGTC and AC<u>AG</u>). Furthermore, both introns have the sequence CT(G/A)A (CT), 33 nucleotides from the 3' border, having similarities with animal consensus sequences (PyTPuAPy). These consensus sequences participate in the formation of looped intermediate products in the excision.

The nucleotide sequence of the exon of gene 48 is identical with the DNA sequence of the coding region of clone pCHN48.

Example 7 Production of a cDNA Gene Library from Cucumber Leaves 7.1 Purification and Protein Sequence of Cucumber Chitinase A chitinase protein inducible by pathogens is isolated from infected cucumber leaves in accordance with the method described in Métraux (1988). Peptide fragments are then generated from this homogeneous protein preparation by means of generally known processes. The amino acid sequences of these peptide fragments are summarised below:

```
Amino terminus        Ala Gly Ile Ala Ile Tyr Trp Gly Gln Asn Gly  SEQ ID NO.41
                      Asn Glu Gly Ser Leu Ala Ser Thr Cys Ala Thr
                      Gly Asn Tyr Glu Phe Val Asn Ile Ala Phe Leu LysC peptides   (Lys)     Asn Phe Gly Gln Val Ile Leu Ser Ala Ala  SEQ ID NO.42
                      Pro Gln Cys Pro Ile Pro Asp Ala His Leu Asp
                      Ala Ala Ile Lys
                (Lys)     Thr Gly Leu Phe Asp Ser Val Trp Val Gln  SEQ ID NO.43
                      Phe Tyr Asn Asn Pro Pro Cys Met Phe Ala Asp
                      Asn Ala Asp Asn Leu Leu Ser
                (Lys)     Leu Tyr Met Gly Leu Pro Ala Ala Arg Glu  SEQ ID NO.44
                      Ala Ala Pro Ser Gly Gly Phe Ile Pro Ala Asp
                (Lys)     Ala Ser Ser Asn Tyr Gly Gly Val Met Leu  SEQ ID NO.45
                      Trp Ser Lys CNBR peptides   (Met)     Phe Ala Asp Asn Ala Asp Asn Leu Leu Ser  SEQ ID NO.46
                (Met)     Gly Leu Pro Ala Ala Arg Glu Ala Ala Pro
                      Ser Gly Gly Phe Ile Pro Ala Asp Val Leu Ile  SEQ ID NO.47
                      Ser Gln Val Leu Pro Thr Ile Tryptic peptides      Val Leu Leu Ser Ile Gly Gly Gly Ala          SEQ ID NO.48
                      Thr Gly Leu Phe Asp  ?  Val                  SEQ ID NO.49
                      Leu Tyr Met Gly Leu Pro Ala Ala              SEQ ID NO.50
                      Ala Ser Ser Asn Tyr Gly Gly Val              SEQ ID NO.51
                      Ala Phe Asp Asn Gly Tyr                      SEQ ID NO.52
```

7.2 Production of a cDNA Library from TNV-Infected Cucumber Leaves

Cucumber leaves are infected with tobacco necrosis virus (TNV). 5 days after the infection, the RNA is isolated in accordance with the above description [see Example 4.1].

Polyadenylated RNA [poly(A)+ RNA] is isolated by means of standard processes [see Section 4.2] and used for the production of a cDNA gene library. This is produced substantially in accordance with the process described in Gubler and Hoffman (1983) in a λ Zap cloning vector [STRATAGEN].

7.3 Isolation of cDNA Clones Coding for a Cucumber Chitinase

Two regions from the protein sequences determined above are selected for the production of oligonucleotide probes. The synthesised oligonucleotide probes cover all possible combinations of mRNA capable of coding for the selected peptides:

```
              G  T      A
Probe 1: 5'-CCATTCTGNCCCCAGTA-3'          SEQ ID
                                          NO.53

G  G   G  G    C
Probe 2: 5'-FFATTATTATAAAATTGNACCCA-3'    SEQ ID
                                          NO.54
```

Approximately 300 000 plaques are plated out from the previously constructed cDNA library. Duplicate copies of these plaques are tested with a $^{32}$P-labelled oligonucleotide mixture 1 (probe 1) or 2 (probe 2). Plaques that yield positive results with both probes are isolated. The isolation of the plaques and the automatic excision are carried out in accordance with the manufacturer's instructions [Stratagene Lambda Zap Laboratory Manual, Stratagen, San Diego, USA].

A suitable positive clone is spliced into the "Bluescript" plasmid and is designated pBSCucCht5. The sequence of this cDNA clone can be determined by dideoxy sequencing [see SEQ ID NO 11.]

II. Construction of Chitinase and Glucanase Mutants

II.1. Chitinase Mutants

Example 8 Introduction of New Restriction Cleavage Sites

In the construction of the chitinase mutants, various parts of the chitinase clones used are linked with one another. In order to be able to achieve this aim, the parts must be compatible, that is to say suitable restriction cleavage sites must be introduced into the various sequences. Hereinafter there are used the restriction cleavage sites listed below, all of which lead to the same cohesive ends:

BamHI [G/GATCC]

BclI [T/GATCA]

BglII [A/GATCT]

The reading frame is in each case so selected that GAT functions as the codon for aspartate.

Example 9 Construction of Mutants of the Tobacco Chitinase Gene

By splicing the EcoRI/HindIII insert from pCHN87, a subcloned fragment of the genomic chitinase clone CHN17 [for the production thereof see Section 12.2], into plasmid pTZ18R, pTRCH1 is obtained. Plasmid pTZ18R is commercially available from PHARMACIA.

The insert of the cDNA clone pCHN48 [see Section 4.4] that comprises the entire cDNA sequence is isolated by partial digestion with PstI and cloned into plasmid pUC8. The clone so formed is designated pCHN6.

The large PstI fragment from pCHN6 is cloned into plasmid pUC18, forming two different clones [pUCH2 and pUCH3] which differ in the orientation of the insert spliced into the polylinker.

The EcoRI/HindIII fragment from pUCH2 is then isolated and spliced into plasmid pTZ18U. Plasmid pTUCH2 is obtained in this manner. Plasmid pTZ18U is likewise commercially available from PHARMACIA.

The EcoRI/HindIII fragment from pUCH3 is likewise isolated and cloned into plasmid pTZ18R. The clone so formed is designated pTRCH3.

Example 10 Oligonucleotide-mediated Mutagenesis

For oligonucleotide-mediated mutagenesis, the following oligonucleotides are synthesised by means of customary methods known to the person skilled in the art:

```
No. 1   CTGCCTCGGCTGATCAATGTGG      SEQ ID NO.56
No. 2   TTTGGAAATTGACTCTTAGTCG      SEQ ID NO.56
No. 3   CCAGAGATCTTTTGGGAAATGG      SEQ ID NO.57
No. 4   GACTTTTAGTCAATACTATGTAA     SEQ ID NO.58
No. 5   GACTTTTAGTCCGTACTATGTAA     SEQ ID NO.59
No. 6   CTTTTGGAAAAGATCTTTTAGTCG    SEQ ID NO.60
No. 7   CCGCTCTTCGGATCCGGCTGG       SEQ ID NO.61
No. 8   CAGCATCGGATGATCAGGAAGCTC    SEQ ID NO.62
No. 9   CATCTTCTAGATTTAGTCTC        SEQ ID NO.63
```

The nucleotides that are changed in comparison with the wild type are shown underlined and in boldface.

The restriction cleavage sites are indicated by a blank space.

The deletion in oligonucleotide No. 8 is shown by Δ.

The insertion in oligonucleotides No. 3 and No. 8 is shown in italics.

10.1 Mutagenesis of the Tobacco Chitinase Clones

In order to produce single-stranded plasmids, the starting plasmids are introduced into a dam$^-$ strain of E. coli by infecting an overnight culture of those bacteria with the helper phage M13KO7 [PHARMACIA]. These plasmids can then very easily be precipitated from the culture supernatant by means of ammonium acetate and polyethylene glycol (PEG 6000) and extracted with phenol/chloroform and chloroform. After precipitation again with ethanol, the isolated DNA is used for the actual mutagenesis [DNA from approximately 5 ml of culture per mutagenesis].

200 pmol of each oligonucleotide are phosphorylated for a period of 45 minutes at a temperature of 37° C. in 30 μl of 0.1M tris-HCl (pH 7.5), 10 mM MgCl$_2$, 6 mM dinitrothreitol (DTT), 2 mM ATP and 5 units of T4 polynucleotide kinase. The reaction is stopped by subsequent incubation for 10 minutes at 60° C.

The single-stranded DNA is mixed with 2.5 μl of phosphorylated oligonucleotide and 1 μl of solution A [0.2M tris-HCl (pH 7.5), 0.1M MgCl$_2$, 0.5M NaCl, 10 mM DTT] in a final volume of 30 μl and incubated first for 5 minutes at 80° C. and then for 20 minutes at room temperature.

13 μl of the following mixture are then added to each test tube:

| | |
|---|---|
| 18.5 μl | of H$_2$O |
| 2.0 μl | of solution B [0.2 M tris-HCl (pH 7.5), 0.1 M MgCl$_2$, 0.1 DTT] |
| 2.0 μl | of 10 mM ATP |
| 2.0 μl | of dNTP mixture (10 mM each dATP, dCTP, dGTP, dTTP) |
| 1.0 μl | of Klenow fragment |
| 0.5 μl | of T4 DNA ligase |

This mixture is incubated for 30 minutes at a temperature of 32° C. and then for a further 2 to 16 hours at room temperature.

A quarter of this batch is transformed into competent *E. coli* mutS cells (repair-deficient strain). These cells are shaken for 3 to 6 hours in 2×L or 2×TY medium at 37° C. The plasmid DNA is then isolated by means of a mini-preparative method known to the person skilled in this field. The isolated DNA is then transformed into competent *E. coli* DH5a cells which are plated out on an ampicillin-containing medium. The mutants can then be identified very easily by colony hybridisation using the radioactively labelled mutagenic oligonucleotide. In addition, a restriction analysis can be carried out, since all the mutants have gained or lost a cleavage site as a result of the mutation.

10.1.2 pTRCH4

Plasmid pTRCH1 is mutated using oligonucleotide No. 1. The newly formed plasmid is designated pTRCH4. In this mutation, a BclI restriction cleavage site is introduced at the first codon of the DNA sequence coding for the mature chitinase, the amino acid coded for being changed from glutamic acid to aspartic acid [Glu1→Asp1].

10.1.3 pTRCH6

Plasmid pTRCH3 is mutated using oligonucleotide No. 2. The newly formed plasmid is designated pTRCH6. In this mutation, codon 300 of the DNA sequence coding for the mature chitinase is changed from glycine to a stop codon (Gly300→Stop300), and a HinfI restriction cleavage site is introduced at the same time.

10.1.4 pTUCH6

The HindIII/PvuII fragment of pTRCH3 and the PvuII/HindIII fragment of pTRCH6, which contain the above mutation, are spliced into vector pTZ18U which has previously been cleaved with HindIII/EcoRI. Plasmid pTUCH6 is obtained in this manner.

10.1.5 pTUCH7

Plasmid pTUCH2 is mutated using oligonucleotide No. 3. The newly formed plasmid is designated pTUCH7. In this mutation, a BglII restriction cleavage site is introduced in the region of codon 295/296 of the DNA sequence coding for the mature chitinase. Since this restriction cleavage site is located in a different reading frame than is the case with the other mutants described hitherto, a G is inserted at codon 297. A compatible reading frame is thus obtained again.

10.1.6 pTUCH8

Plasmid pTUCH2 is mutated using oligonucleotide No. 4. The newly formed plasmid is designated pTUCH8. In this mutation, codon 304 of the DNA sequence coding for the mature chitinase is changed from aspartic acid to asparagine [Asp304→Asn304]. This leads to the loss of a TaqI cleavage site.

10.1.7 pTUCH9

Plasmid pTUCH2 is mutated using oligonucleotide No. 5. The newly formed plasmid is designated pTUCH9. In this mutation, codon 304 is changed from aspartic acid to arginine [Asp304→Arg304], which likewise leads to the loss of a TaqI cleavage site.

10.1.8 pTUCH10

Plasmid pTUCH2 is mutated using oligonucleotide No. 6. The newly formed plasmid is designated pTUCH10. In this mutation, codon 299 is changed from asparagine to lysine [Asn299→Lys299] and codon 300 is changed from glycine to aspartic acid [Gly300→Asp300]. A BglII cleavage site is introduced at the same time.

10.2 Mutagenesis of the Cucumber Chitinase Clones

The mutagenesis of the cucumber chitinase clones is carried out analogously to the process described in Example 11.1.

The EcoRI insert from the cucumber chitinase cDNA clone pBSCucCht5 [see Section 7] is cloned into plasmid pTZ18U. The plasmid so constructed is designated pTUCU2.

10.2.1 pTUCU4

Plasmid pTUCU2 is mutated using oligonucleotide No. 7. The newly formed plasmid is designated pTUCU4. In this mutation, a BamHI restriction cleavage site is introduced at the last codon of the DNA sequence coding for the signal peptide, as a result of which the following codon is so changed that it codes for the amino acid proline instead of for alanine [Ala-1→Pro -1].

10.2.2 pTUCU5

Plasmid pTUCU2 is mutated using oligonucleotide No. 8. The newly formed plasmid is designated pTUCU5. In this mutation, a BclI restriction cleavage site is introduced in the region of the stop codon of the cucumber chitinase. As a result, the stop codon is converted into an aspartic acid codon [Stop268→Asp268].

10.2.3 pTUCU6

Plasmid pTUCU2 is mutated using oligonucleotide No. 9. The newly formed plasmid is designated pTUCU6. In this mutation, an XbaI restriction cleavage site is introduced in the region of the 3' non-coding sequence of the cDNA sequence [in the region of nucleotides 981–986 of clone pBSCucCht5], as a result of which cloning into the vector pGY1 is possible.

II.2. Glucanase Mutants

Example 11 PCR-Mediated Mutagenesis

The base triplet [GTC=valine] coding for the first amino acid of the C-terminal extension is converted into the stop codon TGA using the PCR method.

The methods of carrying out a PCR mutagenesis are very well known to the person skilled in this field. They are described, for example, in the following references: Wang et al (1989); Innis et al (1990) and Erlich (1989).

Moreover, a corresponding PCR kit is available commercially from PERKIN-ELMER CETUS [Norwalk, Conn., USA] or other manufacturers, and the process can be carried out in accordance with the instructions contained therein.

11.1: Construction of pCIB1005BΔVTP

This construct can be produced starting from plasmid pCIB1005B, which is deposited at the "American Type Culture Collection" [ATCC] in Rockville, Md., USA, under number ATCC 40770 and the construction of which is described in detail in EP-A 0,392,225.

Plasmid pCIB1005B codes for a complete chimaeric basic prepro-β-1,3-glucanase from tobacco with a complete N-terminal signal sequence and a C-terminal extension comprising 22 amino acids, in a CaMV 35S expression vector. Plasmid pCIB1005BΔVTR, the production of which is described below, codes for the same glucanase, but the C-terminal extension comprising 22 amino acids has been deleted functionally by the insertion of a stop codon at the end of the sequence coding for the mature protein.

The following oligonucleotides are used in the PCR amplification:

```
Oligo1: 5'-GGG ACA CAC GTG CAC CTT-3'                                    SEQ ID NO.64

Oligo2: 5'-CTG TCC CAA ACT CCA CCA GAT CAC CCA AAG TTG ATA TTA TAT T-3'  SEQ ID NO.65

Oligo3: 5'-AAT ATA ATA TCA ACT TTG GGT GAT CTG GTG GAG TTT GGG ACA G-3'  SEQ ID NO.66

Oligo4: 5'-GCC TCC CCT TCA TCG TCC-3'                                    SEQ ID NO.67
```

Oligonucleotide 1 [oligo1] corresponds to a sequence in the coding region of the glucanase DNA that is located upstream of the XhoI cleavage site located there.

Oligonucleotide 3 [oligo3] comprises the region in the region of the 3'-end of the sequence coding for the mature glucanase protein followed by the stop codon to be introduced and a part of the sequence coding for the C-terminal extension.

Oligonucleotide 2 [oligo2] has a sequence corresponding to oligo3, but in the anti-sense orientation.

Oligonucleotide 4 [oligo4] comprises a sequence that is located in the tml 3' region of pCIB 1005B, downstream of the SacI cleavage site located there.

Three PCR reactions are carried out:

(1) PCR1 with oligo1 and oligo2 as primers and pCIB 1005B as template;
(2) PCR2 with oligo2 and oligo4 as primers and pCIB1005B as template;
(3) PCR3 with oligo1 and oligo4 as primers and the products of the PCR1 and PCR2 reactions as templates. The first two cycles of the PCR3 reaction are carried out with only the templates; only then are the primers added.

The product of the PCR3 reaction is digested with SacI and XhoI and separated by means of agarose gel. The band corresponding to 725 bp is cut out of the gel and purified.

Plasmid pCIB1005B is then likewise digested with XhoI and SacI and linked overnight to the digested and purified PCR3 fragment in a ligase reaction. The ligation mixture is used to transform competent *E. coli* DH5a cells. The selection of the transformants is carried out using ampicillin. Plasmids pCIB1005B and pCIB1005BΔVTP can be isolated from overnight cultures of transformed cells and used for the subsequent transfection of *Nicotiana plumbaginifolia* protoplasts. The correctness of the constructs obtainable in this manner is confirmed by sequence analysis.

III. Incorporation of the Chitinase Mutants into a Plant Expression Plasmid

Example 12 Construction of Plasmid pSCH10

Plasmid pSCH10 contains the sequence coding for tobacco chitinase, comprising the genomic clone CHN17 as well as the cDNA clone CHN48, spliced in the vector plasmid pGY1. This sequence is flanked by the 35S promoter of the CaMV virus and by its termination sequences. This construct is therefore the wild-type chitinase construction. It is described in detail below.

12.1 Construction of Plasmid pGY1

Plasmid pGY1 is derived from the plant expression vector pDH51 described in Pietraak et al (1986). In plasmid pGY1, the NcoI cleavage site of the starting plasmid pDH51 has been replaced by an XhoI cleavage site.

Plasmid pDH51 is cleaved with NcoI and the projecting ends are filled up using Klenow polymerase. The ends, which are now blunt, are then ligated with an XhoI linker (CCTCGAGG).

12.2 Construction of Plasmid pSCH10

Plasmid pSCH10 comprises the sequence coding for chitinase, the 5'-transcribed non-coding sequence, 21 base pairs of the chitinase gene 48 located upstream of the transcription start site, and a 31 bp non-coding sequence, spliced into the BamHI/PstI cloning site of the CaMV 35S plant expression vector pGY1.

The process steps necessary for the production of pSCH10 are described in more detail below:

(1) The genomic clone 1CHN17, which comprises the chitinase gene 48, is cleaved with HindIII. The resulting 5.6 kb HindIII fragment is isolated and spliced into the HindIII cloning site of the plasmid pUC8, forming plasmid pCHN65.

(2) Plasmid pCHN65 is cleaved with EcoRI, and the resulting 2.5 kb fragment comprising the 5'-end of the region coding for chitinase is likewise cloned in pUC8. The resulting plasmid is designated pCHN68.

(3) Plasmid pCHN68 is digested with PstI and religated (linked to itself) with the loss of a 0.5 kb PstI/EcoRI fragment. The resulting plasmid is designated pCHN74.

(4) In order to clone the 5'-non-coding region of the transcript of gene 48 after a BamHI cleavage site, the plasmid pCHN74 is first digested with HphI, then provided with blunt ends by the action of T4 DNA polymerase and finally cleaved with PstI. The HphI/PstI fragment is isolated and spliced into the plasmid pUC8 digested with HindII/Pst [Vieira & Messing (1982)], forming pCHN87.

After sequencing, it can be seen by reference to the DNA sequence that during the last process step a base of the ½ HindII cleavage site has been lost.

(5) pCHN87 is digested with EcoRI and HindIII and spliced into the cloning vector pUC9 [Vieira & Messing (1982)]. The resulting plasmid is designated pCHN88.

(6) The 1 kb PstI fragment of the tobacco cDNA clone 48 (pCHN 48) is spliced into the PstI cloning site of plasmid pUC8, forming pCHN78.

(7) The PstI insert of plasmid pCHN78 is freed by cleaving the plasmid with the restriction enzyme PstI and spliced into the PstI site of pCHN88, so that the complete DNA sequence coding for chitinase is re-established. The resulting plasmid is designated pCHN89.

(8) The plasmid pCHN89 is then digested completely with BamHI and partially with PstI. The resulting 1.5 kb fragment is cloned into the plant expression vector pGY1, which has been cleaved beforehand likewise with BamHI and PstI, forming pSCH10. As a result of this cloning step, the DNA sequence coding for chitinase is placed between the CaMV promoter and the CaMV termination sequence.

Example 13 Incorporation of the Chitinase Mutants into the Plant Expression Plasmid pSCH10

13.1 Incorporation of the Tobacco Chitinase Mutants

The PstI fragment of plasmid pSCH10 is replaced by the following PstI fragments:

PstI fragment of pTUCH6 ⟶ pSCM3

PstI fragment of pTUCH7 ⟶ pSCM25

PstI fragment of pTUCH8 ⟶ pSCM22

PstI fragment of pTUCH9 ⟶ pSCM23

PstI fragment of pTUCH10 ⟶ pSCM24

These plasmids now comprise mutated 3'-terminal targeting sequences, which have the following nucleotide sequences:

```
pSCH10:  5'-GGA AAT GGA CTT TTA GTC GAT ACT AGT TAA-3'  SEQ ID NO.68 pSCM24:  5'-GGA AAA GAT CTT TTA GTC GAT ACT ATG TAA-3'  SEQ ID NO.69 pSCM22:  5'-GGA AAT GGA CTT TTA GTC AAT ACT ATG TAA-3'  SEQ ID NO.70 pSCM23:  5'-GGA AAT GGA CTT TTA GTC CGT ACT ATG TAA-3'  SEQ ID NO.71
```

The nucleotides that are changed (mutated) in comparison with the wild-type plasmid [pSCH10] are shown in boldface and underlined.

13.2 Incorporation of the Cucumber Chitinase Mutants 13.2.1 Plasmid pSCU1

The EcoRI/BclI fragment from plasmid pSCM1 and the BamHI/EcoRI fragment from pTUCU4 are cloned into plasmid pTZ18U, which has been cleaved beforehand with EcoRI. Plasmid pTUCU7 is formed.

The EcoRI/NsiI fragment from plasmid pTUCU7 and the NsiI/EcoRI fragment from pTUCU6 are cloned into plasmid pTZ18U, which has been cleaved beforehand with EcoRI. Plasmid pTUCU11 is formed.

Plasmid pTUCU11 is then digested with BamHI and XbaI, and the BamHI/XbaI fragment is isolated. It is then spliced into plasmid pGY1, which has been cleaved beforehand with BamHI/XbaI, plasmid pSCU1 being formed.

13.2.2 Plasmid pSCU3

The EcoRI/NsiI fragment from plasmid pTUCU7 and the NsiI/EcoRI fragment from pTUCU5 are then cloned into plasmid pTZ18U, which has been cleaved beforehand with EcoRI. Plasmid pTUCU10 is obtained in this manner. Plasmid pSCU3 is formed by cloning the XhoI/BclI fragment of plasmid pTUCU10 and the BglII/PstI fragment of plasmid pTUCU7 into plasmid pGY1, which has been cleaved beforehand with XhoI/PstI.

13.2.3 Plasmid pSCU6

Plasmid pSCU6 is obtained by cloning the XhoI/BclI fragment from pTUCU10 and the BglII/PstI fragment from pTUCH10 into plasmid pGY1, which has been cleaved beforehand with XhoI/PstI.

Plasmids pSCU3 and pSCU6 now comprise, in contrast to the control plasmid pSCU1, 3'-terminal targeting sequences which have the following nucleotide sequences

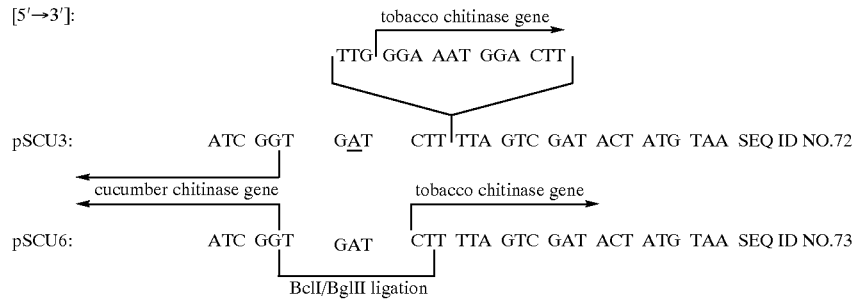

The nucleotides that are changed (mutated) in comparison with the wild type are shown in boldface and underlined.

The nucleotides that have been newly introduced by insertion are shown in italics.

Example 14 Splicing of the pSCM and pSCU Constructs into a Binary Plant Vector

14.1 Construction of Plasmid pCIB200

The construction of this binary vector is based on plasmid pTJS75 described in Schmidhauser and Helinski (1985), which is a derivative of RK2 (An G et al, 1985) and covers a wide host range and has a tetracycline resistance gene. This plasmid is cleaved with the restriction enzyme NarI and then linked to the AccI fragment of pUC4K [Vierra and Messing (1982)], which carries the NptI gene. Plasmid pTJS75kan formed in this manner, which now comprises, in addition to the tetracycline resistance gene, also the NptI gene, is then digested with the restriction enzyme SalI.

At the same time, plasmid pCIB7, which is described in Rothstein SJ et al (1987), is cleaved with EcoRV and the resulting EcoRV fragment, which comprises the left and right T-DNA border sequence from the Ti-plasmid of *Agrobacterium tumefaciens* as well as a chimaeric Nos/NptII gene and the pUC polylinker region, is linked to XhoI linkers.

The resulting construct is then digested with XhoI and cloned into the SalI cleavage site of the plasmid pTJS75kan. The resulting plasmid, the gene map of which is shown in FIG. 1, is designated pCIB200.

14.2 Cloning of the EcoRI Fragments into pCIB200

Plasmid pCIB200 is first cleaved with EcoRI. Then the following EcoRI fragments are cloned into the cleaved pCIB200:

EcoRI fragment from plasmid pSCH10 ⟶ pSCH12
EcoRI fragment from plasmid pSCM3 ⟶ pSCM13
EcoRI fragment from plasmid pSCU1 ⟶ pSCU11
EcoRI fragment from plasmid pSCU3 ⟶ pSCU13

IV. Transformation in Tobacco Protoplasts

The above-described plasmids are tested in vitro in *Nicotiana plumbaginifolia* protoplasts using a "transient expression system".

Example 15 Production and Culturing of *Nicotiana plumbaginifolia* Protoplasts The production and culturing of *Nicotiana plumbaginifolia* protoplasts is carried out by means of known processes, analogously to the procedure described for tobacco [see Section 3]. A detailed description will be found in Shillito and Potrykus (1987) or in Negrutiu et al, 1987.

Example 16 Transformation of the Protoplasts

The transformation of the *Nicotiana plumbaginifolia* protoplasts is carried out in accordance with the process described in Negrutiu et al (1987).

The protoplasts produced according to the above process are suspended after the last purification step in a solution having the following composition:

| | |
|---|---|
| mannitol | 0.4 M |
| $CaCl_2$ | 15–30 mM |
| MES | 0.1% (w/v) |

The protoplast density is $1.6–2 \times 10^6$/ml.

3 ml of this protoplast suspension are first mixed in 15 ml centrifuge tubes with 5 μg of plasmid DNA in the form of a sterile aqueous suspension [Paszkowski et al (1984)]. A few minutes later, 0.3 ml of a polyethylene glycol solution [40% (w/v) PEG 6000 in 0.4M mannitol, 0.1M $Ca(NO_3)_2$, pH 7.0] is added to the mixture, and the batch is mixed carefully. Several minutes later, 4 ml of K3 medium [Z Pflanzenphysiol, 78: 453–455 (1976); Shillito et al (1981)] are added, and the tubes are incubated for 24 hours in the dark at a temperature of from 25° C. to 27° C.

In order to improve the pelleting properties of the protoplasts, a W5 salt solution [Negrutiu et al, 1987] [5.4 ml] may then be added. The protoplasts are then centrifuged at low speed [approximately 60–100×g]. An aliquot of the supernatant is removed for subsequent analysis of the chitinase activity, and the remainder is discarded. The protoplasts which have been separated off are resuspended in the remainder of the medium and transferred to Eppendorf tubes, where the volume is determined approximately. Aliquots of this suspension are used for analysis of the chitinase activity and for Western blotting.

The transformation of the *Nicotiana plumbaginifolia* protoplasts with plasmid pCIB1005B and pCIB1005BΔVTP can also be carried out in accordance with the "Negrutiu" process modified by Goodall et al (1990).

V. TRANSFORMATION AND PRODUCTION OF TRANSGENIC PLANTS

Example 17.1 Transformation of *Agrobacterium tumefaciens* with Binary Vectors The binary vectors described above in Example 14 are transformed into *Agrobacterium tumefaciens* strain LB4404 using the following process. *A. tumefaciens* LBA 4404 contains a deleted Ti-plasmid that lacks the T-DNA region but still has an intact vir region [Hoekema et al (1983)].

*Agrobacterium tumefaciens* strain LB4404 is cultured at a temperature of 30° C. in an overnight culture in 5 ml of MG/L medium [see Section VIII]. 250 ml of MG/L medium are then added to that 5 ml overnight culture, and the whole batch is mixed thoroughly until an optical density of OD=0.6 (at 600 nm) has been obtained. The cells are then collected by means of centrifugation at 8000 g and resuspended in 5 ml of MG/L medium. 200 μl of this cell suspension are incubated with 0.2 μg to 1 μg of binary plasmid DNA in MG/L medium, and after gentle mixing the batch is immediately deep-frozen in a dry ice/ethanol bath. After 5 minutes, the tube is placed in a 37° C. water bath and left there for 5 minutes. 2 ml of MG/L medium are then added. This suspension is then incubated for 2 to 3 hours in a 30° C. water bath. The cells are then collected by means of centrifugation. The cells are resuspended in a small amount of MG/L medium and then plated out on selective media (MG/L plates with 100 μg/ml of gentamycin). The first colonies appear after 2 to 3 days at 30° C.

Example 17.2 Transformation of *Agrobacterium tumefaciens* with Binary Vectors In an alternative form, the binary vectors described above in Example 14 are transferred by means of triparental hybridisation [Rogers SG et al (1986)], using an *E. coli* helper strain that has a plasmid with a tra function, into *Agrobacterium tumefaciens* strain LBA4404. The *E. coli* helper strain used can be, for example, *E. coli* BHB1011 that comprises the plasmid pRK2013 having the tra functions necessary for the transfer of the binary vectors.

*A. tumefaciens* LBA4404 is cultured overnight at 28° C. in LB medium with 20 mg/l of rifampicin and 500 mg/l of streptomycin.

E. coli BHB1011 and the E. coli strains having the binary vectors are cultured overnight at 37° C. in LB medium with 25 mg/l of kanamycin.

1 ml of each of those cultures is centrifuged off at 8000 g, washed in 1 ml of sterile water or 10 mM MgSO$_4$, again centrifuged off, and resuspended in 100 μl of water or of an MgSO$_4$ solution. A plate containing an LB solid medium is divided into four sectors. Drops of the three bacterial cultures are applied one over another in these sectors in such a manner that in three of the four sectors the three possible combinations of two cultures are mixed. These act as controls. In the fourth sector, however, all three cultures are mixed together. After the drops have dried, the plates are incubated overnight at 28° C. Then a sample is taken from each sector and suspended in water or MgSO$_4$ solution. Dilutions of those suspensions are prepared and plated out on LB plates containing 20 mg/l of rifampicin, 500 mg/l of streptomycin and 25 mg/l of kanamycin, and incubated for two to three days at about 28° C. Colonies that grow at a high dilution of the triparental hybrid [nothing is able to grow at a similar dilution of the control hybrids] are freed of any parent bacteria which may still be present by repeated plating-out of individual colonies.

Example 18 Leaf Disk Transformation of N. sylvestris and N. tabacum

The leaf disk transformation is carried out substantially in accordance with the method described in Horsch et al (1985).

A. tumefaciens LBA 4404 (pCIB200; pSCH12; pSCM13; pSCU11; pSCU13) is cultured overnight at a temperature of 28° C. in a glutamate salt medium enriched with 20 mg/l of rifampicin, 500 mg/l of streptomycin and 25 mg/l of kanamycin and adjusted to a pH value of 5.6. In this overnight culture, which contains approximately 3.3×10$^8$ cells, sterile leaf disks (5 mm to 10 mm diameter) of N. sylvestris or N. tabacum c.v. Havana 425 are incubated for 5 minutes. The disks are then removed from the culture and dabbed dry on sterile paper towels before being transferred to 100 mm diameter Petri dishes containing a nutrient culture.

This nutrient culture consists of a basic medium (30 ml), according to Linsmeier and Skoog (1965), solidified with 1% agar (DIFCO) and containing as further additives a pH indicator (chlorophenol red; 5 mg/l) and the plant growth substances kinetin (0.3 mg/l) and a-naphthylacetic acid (2 mg/l). This agar medium (medium A) is covered with a layer of from 1 ml to 2 ml of a 2-week-old suspension culture of S275N cells derived from pith tissue of N. tabacum c.v. Havana 425 (Eichholz et al, 1983) and covered with a filter paper (No. 1 Whatman filter paper). The leaf disks are then placed on the filter paper.

After 48 hours, for the purpose of shoot induction the explantates are placed on a selective medium having the same composition but also containing 350 mg/l of cefotaxim and 100 mg/l of kanamycin (medium B) and are incubated at 25° C. and in diffuse light (80 to 100 μEinstein). Co-cultivated control tissue is inoculated onto the same medium without kanamycin. The explantates are transferred to fresh medium B at weekly intervals.

4 to 8 weeks after the co-cultivation, the green shoots developing from the explantates are harvested and transferred onto 25 ml of medium C (solid medium containing 0.6% Phytagar) in 50 ml containers. The entire tissue is cultured at a temperature of 24° C. to 28° C. with a light intensity of 80 to 100 μEinstein. The shoots form roots after 1 to 2 weeks.

VI. ANALYSIS OF THE TRANSGENIC PLANT MATERIAL (A) Indirect Demonstration of Vacuole Localisation

Example 19 Analysis of the Transformed Protoplasts

The analysis of the transformed protoplasts is carried out in accordance with the processes described in detail in Sections 17 and 20.3.

19.1: Chitinase Activity

As will be seen from the activity data in Table 1, although the control protoplasts have an endogenous chitinase activity, only slight activity can be demonstrated in the supernatant.

In contrast, all constructs of tobacco chitinase exhibit a markedly increased total activity both in the pellet and in the supernatant. The overall increase in chitinase activity in all tested supernatant samples is presumably due to an overloading of the cellular sorting system. However, marked differences can be seen:

In the case of constructs pSCH10, pSCM22, pSCM23 and pSCM24, the chitinase activity in the pellet is 3–4 times greater than that measured in the controls. In the case of the pSCM3 construct, however, the chitinase activity in the pellet is increased by only 35%.

In the case of the cucumber chitinase constructs pSCU1, pSCU3 and pSCU6, the chitinase activity in the pellet is increased by only 10–20%, while the activity in the supernatant is greater by a factor of 7 to 8 [or 4 in the case of pSCU3] in comparison with the controls.

The results shown in Table 1 are confirmed by the Western blot results. The Western blot data for the cucumber chitinase constructs, for example, clearly show that, in the case of pSCU1 (wild type), only very little chitinase is present in the transformed protoplasts, while the protoplasts transformed with pSCU3 and pSCU6 contain very high chitinase concentrations.

19.2: Glucanase Activity

The results obtained with the control protoplasts [see Table 10] show that the b-1,3-glucanase from Nicotiana tabaccum is retained in the cell.

A comparable result can be obtained using the intact construct [pCIB1005B], in this case there merely being observed a stronger signal in the protoplast extracts. This shows that the tobacco glucanase is also retained in the protoplasts and therefore is directed correctly into the cellular compartment.

When the construct having the deleted or inactivated C-terminal extension [pCIB1005B6VTP] is used, however, the b-1,3-glucanase is secreted into the culture medium.

Example 20 Analysis of the Transformed Plants

The plants transformed in accordance with Example 18 are analysed by means of the processes described below.

20.1 Extraction of the Intercellular Fluid (ICF)

The extraction of intercellular fluid from plant tissue can be carried out in accordance with the method described in Parent and Asselin (1984).

In that method leaves of regenerated, transgenic plants are first collected and cut into pieces of 4 to 5 cm$^2$ which are then infiltrated with a large excess of cold (about 4° C.) buffer, in vacuo for 30 seconds each, with gentle shaking.

The said buffer advantageously has the following composition:

| | |
|---|---|
| tris-HCl [pH 7.8] with 0.5M sucrose | 25.0 mM |
| $MgCl_2$ | 10.0 mM |
| $CaCl_2$ | 10.0 mM |
| phenylmethylsulfonyl fluoride (PMSF) | 0.5 mM |
| 2-mercaptoethanol | 5.0 mM |

Alternatively, it is also possible to use a 50 mM citrate buffer (pH 5.5). The operation can also be carried out at room temperature.

On removal of the vacuum, the buffer penetrates the leaves. The pieces of leaf are then carefully dried and transferred to a 20 ml syringe. The syringe is suspended in a centrifuge tube and centrifuged for 10 minutes at low speeds (about 1000×g) and at low temperature (4° C.).

20.2 Extraction of the Intracellular Protein Fraction

The pieces of leaf treated in accordance with Section 20.1 are then homogenised in the same buffer. The coarse particles are separated off by centrifugation.

20.3 Determination of Chitinase Activity

The protein concentration in the two extracts is determined by means of the BIORAD Protein Assay, which is based on the Bradford process. That process is based on the colour change of a dye in dependence upon the protein concentration.

The chitinase activity can be determined by means of a radiometric assay using radioactively labelled [tritiated] chitin [Boller et al (1983)]. The results for the tobacco chitinase transformants are shown in Table 2, and those for the cucumber chitinase transformants in Table 3.

In summary, therefore, the results of the transformation experiments carried out here with protoplasts and whole plants show that the peptide fragment according to the invention at the C-terminal end of basic chitinase from tobacco is responsible for directing chitinase specifically into the vacuole of the plant. Moreover, the results with pSCM22, pSCM23 and pSCM24 clearly demonstrate that a certain variation within the amino acid sequence at the C-terminal end is permitted without the targeting function of that sequence being lost as a result. If the 3'-terminal targeting sequence is missing [pSCM3; pSCM13], then a large part of the chitinase otherwise present in the vacuole is secreted into the extracellular space.

Furthermore, on the basis of these results it is also possible to show that the DNA sequence according to the invention acts as a targeting signal even when operably linked to a heterologous gene [cucumber chitinase gene; pSCU3; pSCU6; pSCU13] in that the chitinase protein that is naturally secreted is retained in the plant cell, most probably within the vacuole.

(B) Direct Demonstration of Vacuole Localisation

Example 21.1 Isolation of Protoplasts (adapted according to Muller et al, 1983)

Leaves of transgenic N. sylvestris plants are cut into pieces of 1–1.5 g and placed in Petri dishes in a K3M osmotically controlled medium. K3M contains half the concentration of the K3 macroelements (therefore to 1 liter 75 mg of $NaH_2PO_4.H_2O$, 450 mg of $CaCl_2.2H_2O$, 1250 mg of $KNO_3$, 125 mg of $NH_4NO_3$, 67 mg of $(NH_4)_2SO_4$, 125 mg of $MgSO_4.7H_2O$) and 84 g of mannitol, pH 5.6; the osmolarity is adjusted to 500 mOsm. The leaves are then cut into narrow strips and incubated in the same osmotically controlled medium for one hour. The leaf strips are then drained and placed in 10 ml/dish of digestion solution. The digestion solution comprises 0.4% macerozyme R10 (Serva) and 0.6% cellulysin (Calbiochem) in K3M (that comprises 75.6 g of mannitol, so that the osmolarity with the enzymes is again 500 mOsm). The Petri dishes are sealed with Parafilm and incubated overnight in the dark at 26° C. without shaking. In order to accelerate the digestion the leaf strips may also be vacuum-infiltrated with double the enzyme concentration and then incubated for 2–3 hours with slow shaking (30–40 rpm).

The protoplasts are filtered through a 100 µm filter, which is then rinsed with a half volume of 0.6M sucrose. The suspension is transferred to 15 ml centrifuge tubes, covered with a layer of 2 ml of K3M and centrifuged for 10 minutes at 1000 g. The protoplasts are removed from the interphase by suction, diluted with K3M and removed by centrifugation for 10 minutes at 700 g. The protoplasts removed by centrifugation are then resuspended in K3M medium.

Example 21.2 Isolation of Vacuoles (adapted according to Boudet and Alibert, 1987)

The protoplasts are resuspended in a K3M medium (pH 6.5) comprising 20% Ficoll. 2.5 ml thereof are transferred to centrifuge tubes and then covered with successive layers of the following solutions: 2 ml of 15% Ficoll, 7 mg of DEAE-dextran (pH 6.5); 2 ml of 10% Ficoll, 3 mg of dextran sulfate (pH 8.0); 2 ml of 6% Ficoll, 3 mg of dextran sulfate (pH 8.0); and approximately 4 ml of 0% Ficoll (pH 8.0) (brimfull). The tubes are centrifuged in a centrifuge rotor (SW 41.14, Kontron) first for 15 minutes at 3500 rpm and then for 105 minutes at 40 000 rpm. The vacuoles are removed from the 0–6% Ficoll interphase by suction.

Markers are measured according to Boller and Kende (1979). In order to measure the hexose phosphate isomerase, the dextran sulfate must first be precipitated with DEAE-dextran before the measurement is possible. A protein determination according to Bradford is not possible since both polybases interfere with that determination. The results in Table 5 were normalised with respect to the vacuole marker enzyme a-mannosidase as 100%.

A comparison of the specific chitinase activities shown in Table 4 confirms the results from Table 2:

In the case of the plants M13.4 and U11.4.2 transformed with plasmid pSCM13 or pSCU11, respectively, secretion of the chitinases is found, while in the case of the plants M10.4 and U13.15 transformed with plasmid pSCH12 and pSCU13, intracellular localisation can clearly be demonstrated. Western blot confirms that the endogenous N. sylvestris chitinase is present intracellularly and in the case of the protoplasts M13.4 is responsible for the majority of the residual activity.

It was possible to isolate protoplasts from plants M10.7.4 and U13.15. Measurement of various markers (Table 5) confirms the localisation in the vacuole of the chitinases carrying a C-terminal sequence. In this case too, Western blot confirms this localisation. The endogenous chitinase is likewise located in the vacuole.

Seeds of one or more self-pollinated plants could be obtained from all series. It was possible to demonstrate that the chitinase over-production and the localisation is passed on to the subsequent generations.

DEPOSIT

The following strains are deposited at the "American Type Culture Collection" in Rockville, Md., USA in accordance with the requirements of the Budapest Treaty:

| Plasmid | Deposit date | Deposit number [ATCC] |
|---|---|---|
| pBscucchi/chitinase (abb.: pBSCucCht5) | 29.12.1988 | 40528 |
| pBSGluc39.1 | 29.12.1988 | 40526 |
| pCIB1005B | 13.03.1990 | 40770 |

MEDIA AND BUFFER SOLUTIONS
Medium A

| | |
|---|---|
| $NH_4NO_3$ | 1650 mg/l |
| $KNO_3$ | 1900 mg/l |
| $CaCl_2.2H_2O$ | 440 mg/l |
| $MgSO_4.7H_2O$ | 370 mg/l |
| $KH_2PO_4$ | 170 mg/l |
| $Na_2EDTA$ | 37.3 mg/l |
| $FeSO_4.7H_2O$ | 27.8 mg/l |
| $H_3BO_3$ | 6.2 mg/l |
| $MnSO_4.4H_2O$ | 22.3 mg/l |
| $ZnSO_4.7H_2O$ | 8.6 mg/l |
| KI | 0.83 mg/l |
| $Na_2MoO_4.2H_2O$ | 0.25 mg/l |
| $CuSO_4.5H_2O$ | 0.025 mg/l |
| $CoCl_2.6H_2O$ | 0.025 mg/l |
| sucrose | 30.0 g/l |
| thiamine hydrochloride | 0.400 mg/l |
| myo-inositol | 100.0 mg/l |
| kinetin | 0.3 mg/l |
| α-naphthylacetic acid | 2.0 mg/l |
| chlorophenol red | 5.0 mg/l |
| agar | 10.0 g/l |

Medium B
same composition as medium A but without α-naphthylacetic acid and with the following additional constituents:

| | |
|---|---|
| cefotaxim | 500 mg/l |
| kanamycin | 75 mg/l |

Medium C
same composition as medium B but without kinetin
MG/L medium for Agrobacterium

| | |
|---|---|
| L-broth | 50% |
| mannitol-glutamate medium (Holsters et al 1978) | 50% |

K3M osmotically controlled medium [500 mOsm; pH 5.6]

| | |
|---|---|
| $NaH_2PO_4.H_2O$ | 75 mg/l |
| $CaCl_2.2H_2O$ | 450 mg/l |
| $KNO_3$ | 1250 mg/l |
| $NH_4NO_3$ | 125 mg/l |
| $(NH_4)_2SO_4$ | 67 mg/l |
| $MgSO_4.7H_2O$ | 125 mg/l |
| mannitol | 84 g/l |

W5 salt solution

| | |
|---|---|
| NaCl | 154 mM |
| $CaCl_2.2H_2O$ | 125 mM |
| KCl | 5 mM |
| glucose | 5 mM |
| pH 5.6–6.0 | |

Rinse I solution

| | |
|---|---|
| sucrose | 154.0 g/l |
| MES | 0.59 g/l |
| $KNO_3$ | 250.0 mg/l |
| $NH_4NO_3$ | 25.0 mg/l |
| $NaH_2PO_4.H_2O$ | 15.0 mg/l |
| $CaCl_2.2H_2O$ | 90.0 mg/l |
| $MgSO_4.7H_2O$ | 25.0 mg/l |
| $(NH_4)_2SO_4$ | 13.4 mg/l |

TENP buffer

| | |
|---|---|
| tris-HCl (pH 8.0) | 100 mM |
| EDTA | 10 mM |
| NP-40 (Sigma Chem.) | 1% (v/v) |

TBE buffer

| | |
|---|---|
| tris-borate | 89 mM |
| boric acid | 89 mM |
| EDTA | 2 mM |

TE buffer

| | |
|---|---|
| tris-HCl (pH 8.0) | 10 mM |
| EDTA | 1 mM |

SSC

| | |
|---|---|
| NaCl | 1.54 mM |
| sodium citrate | 0.154 mM |
| (pH 7.0) | |

TABLES

TABLE 1

Chitinase activity after transient expression in *Nicotiana plumbaginifolia* protoplasts

| Plasmid | Supernatant ncat/batch | ± SD | Protoplasts ncat/batch | ± SD |
|---|---|---|---|---|
| — | .07 | .01 | .81 | .04 |
| pGY1 | .10 | .00 | .81 | .02 |
| pSCH 10 | 2.05 | .05 | 2.95 | .08 |
| pSCM3 | 2.10 | .09 | 1.08 | .01 |
| pSCM22 | 1.64 | .10 | 2.59 | .04 |
| pSCM23 | 2.65 | .34 | 2.64 | .14 |

TABLE 1-continued

Chitinase activity after transient expression in
*Nicotiana plumbaginifolia* protoplasts

| Plasmid | Supernatant ncat/batch | ± SD | Protoplasts ncat/batch | ± SD |
|---|---|---|---|---|
| pSCM24 | 1.55 | .03 | 2.12 | .52 |
| pSCU 1 | .70 | .02 | .76 | .01 |
| pSCU 3 | .38 | .02 | .87 | .05 |
| pSCU 6 | .87 | .09 | .92 | .04 |

TABLE 2

Tobacco chitinase activity in transgenic plants

| Plasmid | Plant | homogenates | | | | intercellular fluid | | | | % in ICF |
|---|---|---|---|---|---|---|---|---|---|---|
| | | [protein] mg/ml | [chitinase] ncat/ml | spec. act. ncat/mg | ncat/gFW | [protein] mg/ml | [chitinase] ncat/ml | spec. act. ncat/mg | ncat/gFW | |
| pC1B200 | C10 | 4.00 | 8.9 | 2.2 | 44.3 | 0.28 | 3.0 | 10.5 | .6 | 1% |
| pC1B200 | C11 | 1.87 | 6.7 | 3.6 | 33.3 | 0.18 | 1.4 | 8.0 | .3 | 1% |
| pSCH12 | M10.2 | 0.30 | 72.6 | 245.1 | 363.1 | 0.38 | 127.7 | 340.0 | 25.5 | 7% |
| pSCH12 | M10.3 | 0.61 | 229.2 | 375.5 | 1146.1 | 0.39 | 41.3 | 104.6 | 8.3 | 1% |
| pSCH12 | M10.7 | 2.26 | 233.2 | 103.3 | 1166.2 | 0.19 | 39.2 | 207.3 | 7.8 | 1% |
| pSCH12 | M10.13 | 2.07 | 342.6 | 165.9 | 1713.1 | 0.21 | 108.9 | 516.1 | 21.8 | 1% |
| pSCH12 | M10.16 | 2.26 | 261.5 | 115.7 | 1307.7 | 0.17 | 43.4 | 249.7 | 8.7 | 1% |
| pSCH12 | M10.18 | 1.87 | 252.2 | 134.6 | 1260.8 | 0.46 | 46.3 | 101.3 | 9.3 | 1% |
| pSCM13 | M13.2 | 0.85 | 299.2 | 351.3 | 1496.2 | 2.55 | 2462.1 | 964.6 | 492.4 | 25% |
| pSCM13 | M13.4 | 0.89 | 196.6 | 221.9 | 983.2 | 2.31 | 1922.0 | 830.6 | 384.4 | 28% |
| pSCM13 | M13.5 | 0.64 | 133.4 | 209.2 | 666.8 | 2.18 | 1581.5 | 724.9 | 316.3 | 32% |
| pSCM13 | M13.6 | 0.60 | 160.9 | 270.4 | 804.6 | 1.81 | 1584.9 | 876.1 | 317.0 | 28% |
| pSCM13 | M13.10 | 0.44 | 1.8 | 4.1 | 9.1 | 0.42 | 42.2 | 100.5 | 8.4 | 48% |

TABLE 3

Cucumber chitinase activity in transgenic plants

| Construct | plant | HOMOGENATES | | | | ICF | | | | % in ICF |
|---|---|---|---|---|---|---|---|---|---|---|
| | | mg/ml | ncat/ml | ncat/mg | ncat/gFW | mg/ml | ncat/ml | ncat/mg | ncat/gFW | |
| pC1B200 | C10 | 4.0 | .8 | .2 | .10 | .28 | 3.1 | 11.2 | .28 | 74% |
| pC1B200 | C11 | 1.87 | .6 | .3 | .19 | .18 | .90 | 4.9 | .45 | 71% |
| pSCU11 | U11.1 | 3.77 | 3.4 | 0.9 | .84 | .19 | 39.6 | 207.4 | 18.06 | 96% |
| pSCU11 | U11.2 | 2.15 | 2.1 | 1.0 | 4.72 | .32 | 39.3 | 122.4 | 8.99 | 66% |
| pSCU11 | U11.3 | .83 | 1.70 | 2.06 | 2.59 | .20 | 12.86 | 63.63 | 7.50 | 74% |
| pSCU11 | U11.4 | | .11 | | .19 | | .86 | | .37 | 66% |
| pSCU11 | U11.5 | .37 | 1.06 | 2.89 | 1.57 | .21 | 11.68 | 56.41 | 4.92 | 76% |
| pSCU13 | U13.1 | 1.98 | 4.5 | 2.3 | 2.75 | .18 | 4.2 | 23.0 | .48 | 15% |
| pSCU13 | U13.2 | .49 | 2.19 | 4.50 | 3.71 | .29 | 4.94 | 17.01 | 2.01 | 35% |
| pSCU13 | U13.3 | .48 | 5.79 | 12.12 | 9.53 | .19 | 1.27 | 6.82 | .69 | 7% |
| pSCU13 | U13.5 | 3.85 | 17.8 | 4.6 | 2.64 | .20 | 2.5 | 12.0 | .43 | 14% |
| pSCU13 | U13.15 | 1.98 | .67 | .34 | 1.35 | .13 | 1.10 | 8.19 | .22 | 14% |

TABLE 4

Chitinase activity in protoplasts of transgenic plants

| Plasmid | Plant | Homogenate | | | Protoplasts | | | % in protoplasts |
|---|---|---|---|---|---|---|---|---|
| | | [prot.] mg/ml | [chitin.] ncat/ml | [spec. activ.] ncat/mg | [prot.] mg/ml | [chitin.] ncat/ml | [spec. activ.] ncat/mg | [%] % |
| pSCH12 | M10.4 | 0.98 | 153 | 157 | 0.13 | 22.6 | 173.7 | 111 |
| pSCM13 | M13.4 | 1.19 | 183 | 153 | 0.23 | 4.5 | 19.2 | 13 |

TABLE 4-continued

Chitinase activity in protoplasts of transgenic plants

| Plasmid | Plant | Homogenate | | | Protoplasts | | | % in protoplasts |
| --- | --- | --- | --- | --- | --- | --- | --- | --- |
| | | [prot.] mg/ml | [chitin.] ncat/ml | [spec. activ.] ncat/mg | [prot.] mg/ml | [chitin.] ncat/ml | [spec. activ.] ncat/mg | [%] % |
| pSCU11 | U11.4.2 | 2.40 | 10.2[a] | 4.25 | 2.13 | 0.23[a] | 0.11 | 2.6 |
| pSCU13 | U13.15 | 0.75 | 24–4[a] | 32.5 | 0.25 | 12.0[a] | 48.0 | 148 |

[a]These activities were measured in the presence of 2 μl of anti-tobacco-chitinase antibodies

TABLE 5

Localisation of intracellular markers in vacoule preparations from chitinase-over-producing plants

| Marker | Units[a]/10$^6$ protoplasts | Units/10$^6$ vacoules[b] | % total in vacoules |
| --- | --- | --- | --- |
| Experiment 1. Localisation of tobacco chitinase with its C-terminal sequence (plant M10.7.4.) | | | |
| α-mannosidase | 89 | 89 | 100% |
| tobacco chitinase | 66300 | 75100 | 113% |
| hexose 6-phosphate isomerase | 2640 | 170 | 6% |
| chlorophyll | 27 | <4.5 | <17% |
| Experiment 2. Localisation of cucumber chitinase with the C-terminal sequence of tobacco chitinase (plant U13.15) | | | |
| α-mannosidase | 59 | 59 | 100% |
| cucumber chitinase | 12000 | 12200 | 102% |
| hexose 6-phosphate isomerase | 490 | 90 | 18% |
| chlorophyll | 62 | <2.2 | <4% |

[a]pcat for enzymes, μg for chlorophyll
[b]figures normalised with respect to α-mannosidase 100%

TABLE 6

SEGREGATION OF KANAMYCIN RESISTANCE IN THE FIRST SUBSEQUENT GENERATION OF SELFED TRANSGENIC PLANTS (3 KanR: 1 KanS is expected)

| Plasmid | Parent plants | KanR | KanS |
| --- | --- | --- | --- |
| pC1B200 | C2 | — | — |
| | C4 | 39 | 11 |
| pSCH12 | M10.3 | 27 | 12 |
| | M10.7 | 36 | 14 |
| | M10.13 | 39 | 9 |
| pSCM13 | M13.2 | 37 | 11 |
| | M13.4 | 39 | 14 |
| | M13.7 | — | — |
| | M13.10 | 24 | 12 |
| pSCU11 | U11.3 | 33 | 13 |
| | U11.4 | 15 | 39 |
| | U11.5 | 36 | 11 |

TABLE 7

ANALYSIS OF THE PROGENY OF TRANSGENIC PLANTS
(only KanR plants were tested)
Concentration in homogenised leaves

| Plasmid | Parent plant | Plant | mg/ml | ncat/ml | ncat/mg |
| --- | --- | --- | --- | --- | --- |
| pC1B200 | C2 | C2.1 | 2.77 | 27.3 | 9.9 |
| | | C2.2 | 2.23 | 21.7 | 9.8 |
| | | C2.3 | 2.01 | 42.5 | 21.1 |
| | C4 | C4.1 | 2.88 | 8.3 | 2.9 |
| | | C4.2 | 2.82 | 9.6 | 3.4 |
| | | C4.3 | 2.15 | 6.1 | 2.8 |
| | | C4.4 | 2.66 | 7.2 | 2.7 |
| pSCH12 | M10.3 | M10.3.1 | 1.59 | 243.4 | 152.8 |
| | | M10.3.2 | 1.82 | 179.0 | 98.3 |
| | | M10.3.3 | 2.96 | 212.4 | 71.7 |
| | | M10.3.4 | 1.80 | 163.9 | 91.1 |
| | M10.7 | M10.7.1 | 1.92 | 196.5 | 102.1 |
| | | M10.7.3 | 1.72 | 148.2 | 86.3 |
| | | M10.7.4 | 2.23 | 112.5 | 50.5 |
| | M10.13 | M10.13.1 | 2.81 | 283.6 | 100.8 |
| | | M10.13.2 | 2.52 | 217.6 | 86.5 |
| pSCM13 | M13.2 | M13.2.1 | 1.43 | 330.1 | 231.4 |
| | | M13.2.2 | 1.03 | 8.5 | 8.2 |
| | | M13.2.3 | 2.15 | 65.9 | 30.7 |
| | | M13.2.4 | 1.15 | 1.1 | .9 |
| | M13.4 | M13.4.1 | 1.78 | 332.7 | 186.7 |
| | | M13.4.3 | 2.86 | 357.8 | 124.9 |
| | | M13.4.5 | 1.14 | 11.0 | 9.7 |
| | | M13.4.6 | 1.64 | 324.7 | 198.6 |
| | M13.7 | M13.7.3 | 2.60 | 259.3 | 99.9 |
| | M13.10 | M13.10.1 | 1.83 | 235.1 | 128.6 |
| | | M13.10.2 | 2.89 | 153.1 | 52.9 |
| | | M13.10.3 | 2.53 | 504.9 | 199.3 |

TABLE 8

ANALYSIS OF THE PROGENY OF TRANSGENIC PLANTS
(only KanR plants were tested)
Concentration in homogenised leaves

| Plasmid | Parent plant | Plant | mg/ml | ncat/ml | ncat/mg |
| --- | --- | --- | --- | --- | --- |
| pC1B200 | C2 | C2.1 | 2.77 | 4.40 | 1.59 |
| | | C2.2 | 2.23 | 4.06 | 1.82 |
| | | C2.3 | 2.01 | 4.95 | 2.46 |
| PSCU11 | U11.3 | U11.3.1 | 2.52 | 7.38 | 2.93 |
| | | U11.3.2 | 2.14 | 7.69 | 3.59 |
| | U11.4 | U11.4.1 | 1.87 | 35.58 | 19.05 |
| | | U11.4.2 | 1.81 | 46.75 | 25.77 |
| | U11.5 | U11.5.1 | 2.30 | 6.95 | 3.02 |
| | | U11.5.2 | 2.79 | 13.88 | 4.98 |

The chitinase activity was measured in the presence of immunoglobulins against the tobacco chitinase

TABLE 9

Cucumber chitinase activity in transgenic F1 plants

| Construct | Parent plant | Plant | HOMOGENATES | | | | ICF | | | | % in ICF |
| --- | --- | --- | --- | --- | --- | --- | --- | --- | --- | --- | --- |
| | | | mg/ml | ncat/ml | ncat/mg | ncat/gFW | mg/ml | ncat/ml | ncat/mg | ncat/gFW | |
| pC1B200 | C4 | C4.2 | 3.11 | 5.10 | 1.64 | 6.80 | .10 | .50 | 5.30 | .28 | 74% |
| pSCU11 | U11.3 | U11.3.2 | 1.49 | 1.10 | 74 | 2.90 | .24 | 26.67 | 111.12 | 18.06 | 96% |
| pSCU11 | U11.4 | U11.4.1 | 1.63 | 13.70 | 8.40 | 37.80 | .56 | 19.07 | 33.99 | 8.99 | 66% |
| pSCU11 | U11.4 | U11.4.2 | 1.58 | 11.60 | 7.34 | 37.10 | .31 | 12.86 | 41.76 | 7.50 | 74% |

TABLE 10

Activity of $^{35}$S-labelled, mature $\beta$-1,3-glucanase in *Nicotiana plumbaginifolia* protoplasts

| Plasmid | Protoplast extract | Incubation medium |
| --- | --- | --- |
| — | moderate | trace |
| pCIB1005B | strong | trace |
| pCIB1005BΔVTP | moderate | moderate |

BIBLIOGRAPHY

Allen G, "Sequencing of proteins and peptides", in: *Laboratory Techniques in Biochemistry and Molecular Biology*, Vol 8, eds. TS Work and RH Bordon, Elsevier, North-Holland Biomedical Press, Amsterdam (1981).
An G et al, *EMBO J.*, 4: 277–284 (1985).
Birk Y et al, *Biochim. Biophys. Acta*, 67: 326–328 (1963).
Bohlmann et al, *EMBO J* 7: 1559–1565 (1988)
Boller et al, *Planta*, 157: 22–31 (1983).
Boller T and Wiemken A, *Ann Rev Plant Physiol*, 37: 137–164 (1986)
Boller T and Kende H, *Plant. Physiol.* 63: 1123–1132 (1979)
Boudet A M and Alibert G, *Meth. Enzymol.* 148: 74–81 (1987)
Cashmore A, *Genetic Engineering of Plants, an Agricultural Perspective*, Plenum, New York 1983, pages 29–38.
Devereux et al, *Nucl. Acids Res.*, 12: 387–395 (1984).
Erlich et al, *PCR Technology Principles and Applications for DNA Amplification*, Stockton Press, New York (1989)
Eichholz R et al, *Planta*, 158: 410–415 (1983).
Facciotti and Pilet, *Plant Science Letters*, 15: 1–7 (1979).
Felix G and Meins F Jr, *Planta*, 164: 423–428 (1985).
Frank G et al, *Cell*, 21: 285–294 (1980).
Gardner R C et al, *Nucl. Acids Res.*, 9: 2871–2888 (1981).
Garfinkel and Nester, *J. Bact.*, 144: 732–743 (1980).
Glover D M, *DNA cloning, volume 1: a practical approach*; D M Glovered., IRL Press, Oxford and Washington D.C., p.33 (198)
Goodall G et al, *Methods in Enzymology*, 181: 148–161 (1990)
Grimsley N H et al, *Nature*, 325: 177–179 (1987).
Gubler U and Hoffman B J, *Gene*, 25: 263 (1983).
Haymes B T et al, *Nucleic Acid Hybridisation a Practical Approach*, IRL Press, Oxford, England (1985).
Hilder et al, *Nature*, 330: 160–163 (1987).
Hoekema et al, *Nature*, 303: 179–180 (1983).
Hohn T et al, in: "*Molecular Biology of Plant Tumors*", Academic Press, New York, pp. 549–560 (1982).
Hornetal, *Plant Cell Reports*, 7: 469–472 (1988).
Horsch et al, *Science*, 227: 1229 (1985).
Howard et al, *Planta*, 170: 535 (1987).
Innis et al, *PCR Protocols: A Guide to Methods and Applications*, Academic Press, Inc., New York, 1990
Lagrimini L M et al, *Proc. Natl. Acad. Sci., USA* 84: 7542, (1987).
Laurell and McKay, *Methods Enzymology*, 73: 339–361 (1981).
Lathe R et al, *J. Mol. Bio.*, 183: 1–12 (1985).
Linsmeier and Skoog, *Physiol. Plant.*, 18: 101–127 (1965).
Maniatis et al, *Molecular Cloning, A Laboratory Manual*, Cold Spring Harbor Laboratory, 1982.
Matsuoka K and Nakamura K, *Proc. Natl. Acad. Sci. USA*, 88: 834–838 (1991)
Maxam and Gilbert, '*Sequencing end-labelled DNA with base-specific chemical cleavage*', in: *Methods in Enzymology* 65: 499–560, Academic Press, New York, London, (1980)
Meins & Lutz, *Differentiation*, 15: 1–6 (1979).
Metraux J P et al, *Physiol Mol Plant Pathol*, 33: 1–9 (1988).
Mohnen, "*Regulation of Glucanohydrolases in Nicotiana tabacum on the messenger RNA level*", Dissertation University of Illinois at Urbana-Champaign, 1985.
Mohnen et al, *EMBO J.*, 4: 1631–1635 (1985).
Morelli et al, *Nature*, 315: 200 (1985).
Muller J F et al, *Physiol. Plant.* 57: 35–41 (1983)
Murashige and Skoog, *Physiol. Plant.*, 15: 473–497 (1962).
Negrutiu I et al, *Plant Mol. Biol.*, 8: 363–373 (1987).
Neuhaus et al, *Theor. Appl. Genet.*, 74: 30–36 (1987).
Parent and Asselin, Can J Bot, Vol 62: 564–569 (1984).
Paszkowski J et al, *EMBO J*, 3: 2717 (1984).
Petit et al, *Mol. Gen. Genet.*, 202: 388 (1986).
Pietrzak et al, *Nucl. Acids Res.*, 14: 5857–5868 (1986).
Potrykus I and Shillito R D, *Methods in Enzymology*, Vol 118, Plant Molecular Biology, eds. A and H Weissbach, Academic Press, Orlando, 1986.
Rhodes et al, Biotechnology, 6: 56–60 (1988).
Rogers S G et al, *Methods in Enzymology*, 118: 630–633 (1986).
Rothstein S J et al, *Gene*, 53: 153–161 (1987).
Sambrook et al, Molecular Cloning, A Laboratory Manual, Second Edition (1989)
Sanger et al, *Proc. Natl. Acad. Sci., USA* 74: 5463–5467 (1977).
Schmidhauser and Helinski, *J. Bacteriol.*, 164: 446–455 (1985).
Schocher R J et al, *Bio/Technology*, 4: 1093–1096(1986).
Selsted et al, *Infection and Immunity*, 55: 2281–2286 (1987)
Shillito et al, *Bio Technology*, 3: 1099–1103 (1985).
Shillito R D and Potrykus I, In: Methods in Enzymology, eds. Wu R and Grossman L, Academic Press, Orlando, Fla., Vol. 153: 313–306 (1987).
Shillito R D et al, Biotechnology, 7: 581–587 (1989).
Shinshi et al, *Proc. Natl. Acad. Sci., USA* 84: 89–93 (1987).
Shinshi et al, *Planta*, 164: 423–428 (1985).
Shinshi et al, *Proc. Natl. Acad. Sci., USA* 85: 5541–5545 (1988).
Simpson R J and Nice, *Biochem Intl*, 8: 787 (1984).

Southern E M, *J. Mol. Biol.* 98: 503–517 (1975).

Spena et al, *EMBO J.*, 4: 2736 (1985).

Tague B W and Chrispeels M V, *J Cell Biol*, 105: 1971–1979 (1987).

Terry et al, *J. Biol. Chem.* 263: 5745–5751 (1988).

Vierra and Messing, *Gene*, 19: 259–268 (1982).

Wang Y-C et al, *Plant Mol. Biol.*, 11: 433–439 (1988).

Wang et al, *Proc. Nattl. Acad. Sci. USA*, 86: 9717–9721 (1989)

Yamada Y et al, *Plant Cell Rep*, 5:85–88 (1986).

Yanisch-Perron et al, *Gene*, 33: 103–119 (1985).

| | |
|---|---|
| WO 89/1 1291 | EP-A 0,332,104 |
| WO 86/0 4356 | EP-A 0,392,225 |
| WO 88/0 5826 | |
| WO 89/0 4371 | |
| US-P 4,810,777 | |

What is claimed is:

1. A process to discharge into the extrallular space of a plant a protein that naturally has a vacuolar targeting sequence at its C-terminal end which is lost as the protein matures and that is normally directed into the plant vacuole, which process essentially comprises:
    (a) isolating a DNA sequence coding for said protein;
    (b) removing from the open reading frame the sequence coding for said vacuolar targeting sequence to form a DNA sequence encoding the mature protein devoid of said vacuolar targeting sequence;
    (c) splicing the DNA sequence from step (b) into a suitable plant expression vector;
    (d) transforming the product of step (c) into said plant; and
    (e) culturing said plant under conditions whereby the protein encoded by the DNA sequence from step (b) is expressed and secreted.

2. A process for the production of transformed plant material comprising a gene product that naturally has a vacuolar targeting sequence at its C-terminal end which is lost as the gene product matures that is secreted into the extracellular space, which process comprises:
    (a) isolating a DNA sequence coding for a protein that has a vacuolar targeting sequence at its C-terminal end and that is normally directed into the plant vacuole;
    (b) removing from said DNA sequence the sequence coding for said vacuolar targeting sequence to form a DNA sequence encoding the mature protein devoid of said vacuolar targeting sequence;
    (c) splicing the DNA sequence from step (b) into a suitable plant expression vector;
    (d) transforming the product of step (c) into a plant;
    (e) culturing said plant under conditions whereby the protein encoded by the DNA sequence from step (b) is expressed and secreted; and;
    (f) screening the plant material so treated and isolating positive transformants.

3. A recombinant DNA molecule that comprises a structural gene that is in operable linkage with expression signals active in plant cells and codes for a gene product present naturally in the vacuole and in which a 3'-terminal targeting sequence, which is naturally present in the gene, has been deleted or otherwise inactivated and that therefore, on transformation into a plant host, produces an expression product that does not contain a functional C-terminal signal sequence and is secreted into the extracellular space of the plant.

4. A recombinant DNA molecule according to claim 3, wherein the said structural gene is a basic chitinase gene.

5. A recombinant polynucleotide comprising in a 5' to 3' direction of transcription:
    a promoter that is functional in plants and which is operably joined to an open reading frame encoding a vacuolar tobacco basic chitinase that has been modified to target said vacuolar tobacco basic chitinase to the extracellular space by creating a translation stop codon in said open reading frame at the 3' end which results in deletion of the C-terminal amino acids of the vacuolar tobacco basic chitinase necessary for vacuolar targeting; and a transcription termination regulatory region operably joined to said modified open reading frame.

6. A plant comprising the recombinant polynucleotide of claim 5 which secretes vacuolar tobacco basic chitinase to the extracellular space.

7. A recombinant DNA molecule comprising:

an open reading frame encoding a protein which is naturally occurring in a plant vacuole wherein said open reading frame has been modified at the 3' end region necessary for vacuolar targeting to produce a modified open reading frame, wherein said modified open reading frame encodes a modified protein which is targeted to the extracellular space.

8. The recombinant DNA molecule according to claim 7, wherein said DNA molecule further comprises a promoter that is functional in plants operably linked to said modified open reading frame.

9. The recombinant DNA molecule according to claim 7, wherein said DNA molecule further comprises a terminator that is functional in plants operably linked to said modified open reading frame.

10. The recombinant DNA molecule according to claim 7, wherein said 3' end region is modified by inserting a translation stop codon which results in deletion of C-terminal amino acids necessary for vacuolar targeting of said protein.

11. A bacterial cell comprising the recombinant DNA molecule of claim 7, 8, 9, or 10.

12. The bacterial cell according to claim 11, wherein said bacterial cell is an *E. coli* cell.

13. The bacterial cell according to claim 11, wherein said bacterial cell is an *Agrobacterium tumefaciens* cell.

14. A plant cell comprising the recombinant DNA molecule of claim 7, 8, 9, or 10.

15. A plant tissue comprising the recombinant DNA molecule of claim 7, 8, 9, or 10.

16. A plant seed comprising the recombinant DNA molecule of claim 7, 8, 9, or 10.

17. A plant comprising the recombinant DNA molecule of claim 7, 8, 9, or 10.

18. A vector comprising the recombinant DNA molecule of claim 7, 8, 9, or 10.

* * * * *